US009789095B2

(12) United States Patent
Verkman et al.

(10) Patent No.: US 9,789,095 B2
(45) Date of Patent: Oct. 17, 2017

(54) INHIBITORS OF CALCIUM-ACTIVATED CHLORIDE CHANNELS

(71) Applicant: The Regents of the University of California, Oakland, CA (US)

(72) Inventors: Alan S. Verkman, San Francisco, CA (US); Ricardo De La Fuente Gonzalez, Madrid (ES)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/688,365

(22) Filed: Apr. 16, 2015

(65) Prior Publication Data
US 2015/0290175 A1 Oct. 15, 2015

Related U.S. Application Data

(63) Continuation of application No. 13/601,216, filed on Aug. 31, 2012, now abandoned, which is a continuation of application No. 12/747,468, filed as application No. PCT/US2008/086600 on Dec. 12, 2008, now abandoned.

(60) Provisional application No. 61/013,988, filed on Dec. 14, 2007.

(51) Int. Cl.
| A61K 31/381 | (2006.01) |
| C07D 333/50 | (2006.01) |
| A61K 31/426 | (2006.01) |
| C07D 277/42 | (2006.01) |
| C07D 277/46 | (2006.01) |
| C07D 333/68 | (2006.01) |
| C07D 333/80 | (2006.01) |
| C07D 409/12 | (2006.01) |
| G01N 33/50 | (2006.01) |
| G01N 33/84 | (2006.01) |

(52) U.S. Cl.
CPC .......... *A61K 31/426* (2013.01); *A61K 31/381* (2013.01); *C07D 277/42* (2013.01); *C07D 277/46* (2013.01); *C07D 333/68* (2013.01); *C07D 333/80* (2013.01); *C07D 409/12* (2013.01); *G01N 33/5035* (2013.01); *G01N 33/5044* (2013.01); *G01N 33/84* (2013.01); *G01N 2333/705* (2013.01)

(58) Field of Classification Search
CPC .......................... A61K 31/381; C07D 333/50
See application file for complete search history.

(56) References Cited

U.S. PATENT DOCUMENTS

| 5,751,629 A | 5/1998 | Nova et al. |
| 5,789,172 A | 8/1998 | Still et al. |
| 6,083,706 A * | 7/2000 | Florkiewicz ........... A61K 31/00 435/184 |
| 6,312,682 B1 | 11/2001 | Kingsman et al. |
| 6,576,434 B1 | 6/2003 | Holroyd et al. |
| 6,723,848 B2 * | 4/2004 | Wartenberg .......... C07D 333/68 544/333 |
| 6,798,035 B1 | 9/2004 | Low et al. |
| 7,235,573 B2 | 6/2007 | Verkman et al. |
| 7,414,037 B2 | 8/2008 | Verkman et al. |
| 7,638,543 B2 | 12/2009 | Verkman et al. |
| 7,696,244 B2 * | 4/2010 | Verkman ................ A61K 31/12 514/443 |
| 7,888,332 B2 | 2/2011 | Verkman et al. |
| 2003/0064946 A1 | 4/2003 | McSwiggen et al. |
| 2003/0194375 A1 | 10/2003 | Weaver et al. |
| 2004/0265859 A1 | 12/2004 | Pauli et al. |
| 2005/0239740 A1 | 10/2005 | Verkman et al. |
| 2010/0135071 A1 | 6/2010 | Kozicki |
| 2010/0209934 A1 | 8/2010 | Oh et al. |

FOREIGN PATENT DOCUMENTS

| EP | 0 774 464 | 5/1997 |
| WO | WO 92/00091 | 1/1992 |
| WO | WO 92/09300 | 6/1992 |
| WO | WO 95/16918 | 6/1995 |

OTHER PUBLICATIONS

Florkiewicz et al (2000): STN International HCAPLUS database, (Columbus, Ohio), Accession No. 2000:454238.*
Pato et al (2004): STN International HCAPLUS database, (Columbus, Ohio), Accession No. 2004: 722914.*
Ward et al (2006): STN International HCAPLUS database, (Columbus, Ohio), Accession No. 2006: 381034.*
Barnes, "Emerging Targets for COPD Therapy," *Current Drug Targets—Inflammation & Allergy* 4:675-683, 2005.
Barrett et al., "Chloride Secretion by the Intestinal Epithelium: Molecular Basis and Regulatory Aspects," *Annu. Rev. Physiol.* 62:535-572, 2000.
Bolton, "Calcium events in smooth muscles and their interstitial cells; physiological roles of sparks," *J. Physiol.* 570.1:5-11, 2006.
Braun et al., "A non-selective cation current activated via the multifunctional $Ca^{2+}$-calmodulin-dependent protein kinase in human epithelial cells," *Journal of Physiology* 448.1:37-55, 1995.
Caputo et al., "TMEM16A, A Membrane Protein Associated with Calcium-Dependent Chloride Channel Activity," *Science* 322:590-594, 2008.
Carmeliet, "Electrophysiology on the Molecular Way," *Koninklijke Academie Voor Geneeskunde Van België*, Verhandelingen, Leuven, Belgium, Jan. 30, 1993, pp. 5-26.

(Continued)

*Primary Examiner* — Golam M M Shameem
(74) *Attorney, Agent, or Firm* — Seed IP Law Group LLP

(57) ABSTRACT

Provided herein are methods for identifying compounds that are inhibitors of a calcium-activated chloride channel. Aminothiophene and aminothiazole compounds, and compositions comprising these compounds, described herein that inhibit efflux of chloride through a calcium-activated chloride channel are useful for treating diseases, disorders, and sequelae of diseases, disorders, and conditions that are associated with aberrantly increased chloride and fluid secretion, for example, secretory diarrhea.

17 Claims, 20 Drawing Sheets

(56) References Cited

OTHER PUBLICATIONS

Chan et al., "Annexin VI Inhibits Calmodulin-dependent Protein Kinase II-activated Chloride Conductance," *The Journal of Biological Chemistry* 269(51):32464-32468, 1994.

Chao et al., "Activation of intestinal CFTR Cl$^-$ channel by heat-stable enterotoxin and guanylin via cAMP-dependent protein kinase," *The EMBO Journal* 13(5):1065-1072, 1994.

Cuthbert, "The prospects of pharmacotherapy for cystic fibrosis," *Journal of the Royal Society of Medicine* 99(Supplemental No. 46):30-35, 2006.

De La Fuente et al., "Small-Molecule Screen Identifies Inhibitors of a Human Intestinal Calcium-Activated Chloride Channel," *Molecular Pharmacology* 73(3):758-768, 2008.

Eggermont, "Calcium-activated Chloride Channels," *Proc. Am. Thorac. Soc.* 1:22-27, 2004.

Elsliger et al., "Structural and Spectral Response of Green Fluorescent Protein Variants to Changes in pH," *Biochemistry* 38:5296-5301, 1999.

Evans et al., "Molecular and Functional Analyses of Two New Calcium-activated Chloride Channel Family Members from Mouse Eye and Intestine," *The Journal of Biological Chemistry* 279(40):41792-41800, 2004.

Farthing, "Antisecretory Drugs for Diarrheal Disease," *Digestive Diseases* 24:47-58, 2006.

Galietta et al., "Cell-based assay for high-throughput quantitative screening of CFTR chloride transport agonists," *Am. J. Physiol. Cell Physiol.* 281:C1734-C1742, 2001.

Galietta et al., "Green fluorescent protein-based halide indicators with improved chloride and iodide affinities," *FEBS Letters* 499:220-224, 2001.

Genbank Database Accession No. NM_018043.5, revised Jul. 18, 2008, 4 pages.

Ghartey-Tagoe et al., "Plasmid DNA and siRNA transfection of intestinal epithelial monolayers by electroporation," *International Journal of Pharmaceutics* 315:122-133, 2006.

Gyömörey et al., "Non-CFTR chloride channels likely contribute to secretion in the murine small intestine," *Pflügers Arch.—Eur. J. Physiol.* 443(Suppl. 1):S103-S106, 2001.

Hamill et al., "Improved Patch-Clamp Techniques for High-Resolution Current Recording from Cells and Cell-Free Membrane Patches," *Pflügers Arch.* 391:85-100, 1981.

Hartmann et al., "Calcium-dependent regulation of Cl secretion in tracheal epithelium," *Am. J. Physiol.* 262(2 Pt. 1):L163-L168, 1992.

Hartzell et al., "Calcium-Activated Chloride Channels," *Annu. Rev. Physiol.* 67:719-758, 2005.

Hartzell et al., "Looking Chloride Channels Straight in the Eye: Bestrophins, Lipofuscinosis, and Retinal Degeneration," *Physiology* 20:292-302, 2005.

Hegab et al., "Niflumic Acid and AG-1478 Reduce Cigarette Smoke-Induced Mucin Synthesis: The role of hCLCA1," *Chest* 131:1149-1156, 2007.

Jayaraman et al. "Mechanism and Cellular Applications of a Green Fluorescent Protein-based Halide Sensor," *The Journal of Biological Chemistry* 275(9):6047-6050, 2000.

Kidd et al., "Intracellular CA$^{2+}$ and CL$^-$ Channel Activation in Secretory Cells," *Annu. Rev. Physiol.* 62:493-513, 2000.

Loewen et al., "Structure and Function of CLCA Proteins," *Physiol. Rev.* 85:1061-1092, 2005.

Lohi et al., "Upregulation of CFTR expression but not SLC26A3 and SLC9A3 in ulcerative colitis," *Am. J. Physiol. Gastrointest. Liver Physiol.* 283:G567-G575, 2002.

Lorrot et al., "How do the rotavirus NSP4 and bacterial enterotoxins lead differently to diarrhea," *Virology Journal* 4:31, 2007.

Ma et al., "High-affinity Activators of Cystic Fibrosis Transmembrane Conductance Regulator (CFTR) Chloride Conductance Identified by High-throughput Screening," *The Journal of Biological Chemistry* 277(40):37235-37241, 2002.

Ma et al., "Thiazolidinone CFTR inhibitor identified by high-throughput screening blocks cholera toxin-induced intestinal fluid secretion," *The Journal of Clinical Investigation* 110(11):1651-1658, 2002.

Morris et al., "Ca$^{2+}$-dependent Cl$^-$ channels in undifferentiated human colonic cells (HT-29). II. Regulation and rundown," *Am. J. Physiol.* 264:C977-C985, 1993.

Morris et al., "NSP4 elicits age-dependent diarrhea and Ca$^{2+}$-mediated I$^-$ influx into intestinal crypts of CF mice," *Am. J. Physiol.* 277:G431-G444, 1999.

Muanprasat et al., "Discovery of Glycine Hydrazide Pore-occluding CFTR Inhibitors: Mechanism, Structure-Activity Analysis, and In Vivo Efficacy," *J. Gen Physiol.* 124:125-137, 2004.

Namkung et al., "Inhibition of Ca$^{2+}$-activated Cl$^-$ channels by gallotannins as a possible molecular basis for health benefits of red wine and green tea," *The FASEB Journal* 24:4178-4186, 2010.

Namkung et al., "TMEM16A Inhibitors Reveal TMEM16A as a Minor Component of Calcium-activated Chloride Channel Conductance in Airway and Intestinal Epithelial Cells," *The Journal of Biological Chemistry* 286(3):2365-2374, 2011.

Ormö et al., "Crystal Structure of the *Aequorea victoria* Green Fluorescent Protein," *Science* 273:1392-1395, 1996.

Pedemonte et al., "Small-molecule correctors of defective ΔF508-CFTR cellular processing identified by high-throughput screening," *The Journal of Clinical Investigation* 115(9):2564-2571, 2005.

Rufo et al., "Diarrhea-associated HIV-1 APIs potentiate muscarinic activation of Cl$^-$ secretion by T84 cells via prolongation of cytosolic Ca$^{2+}$ signaling," *Am. J. Physiol. Cell Physiol.* 286:C998-C1008, 2004.

Schmiedlin-Ren et al., "Increased Transduction of Human Intestinal Epithelial Cells by Adenoviral Vectors in Inflammatory Bowel Disease," *Inflamm. Bowel Dis.* 11(5):464-472, 2005.

Schroeder et al., "Expression cloning of TMEM16A as a calcium-activated chloride channel subunit," *Cell* 134(6):1019-1029, 2008.

Schultheiss et al., "Histamine-induced ion secretion across rat distal colon: Involvement of histamine $H_1$ and $H_2$ receptors," *European Journal of Pharmacology* 546:161-170, 2006.

Schultheiss et al., "Muscarinic Receptor Stimulation Activates a Ca$^{2+}$-dependent Cl$^-$ Conductance in Rat Distal Colon," *J. Membrane Biol.* 204:117-127, 2005.

Shale et al., "Mucus hypersecretion: a common symptom, a common mechanism?," *Eur. Respir. J.* 23:797-798, 2004.

Suzuki, "The Drosophila tweety family: molecular candidates for large-conductance Ca$^{2+}$-activated Cl$^-$ channels," *Exp. Physiol.* 91.1:141-147, 2006.

Takahashi et al., "Mechanisms of chloride secretion induced by thermostable direct haemolysin of *Vibrio parahaemolyticus* in human colonic tissue and a human intestinal epithelial cell line," *J. Med. Microbiol.* 49:801-810, 2000.

Takeda et al., "Detection of Cholera Enterotoxin Activity in Suckling Hamsters," *Infection and Immunity* 19(2):752-754, 1978.

Tarran et al., "Regulation of Murine Airway Surface Liquid Volume by CFTR and Ca$^{2+}$-activated Cl$^-$ Conductances," *J. Gen. Physiol.* 120:407-418, 2002.

Thiagarajah et al, "New drug targets for cholera therapy," *Trends in Pharmacological Sciences* 26(4):172-175, 2005.

Tradtrantip et al., "Crofelemer, an Antisecretory Antidiarrheal Proanthocyanidin Oligomer Extracted from *Croton lechleri*, Targets Two Distinct Intestinal Chloride Channels," *Molecular Pharmacology* 77(1):69-78, 2010.

Verkman et al., "Fluorescent Indicator Methods to Assay Functional CFTR Expression in Cells," *Methods in Molecular Medicine* 70:187-196, 2002.

Wachter et al., "Sensitivity of the yellow variant of green fluorescent protein to halides and nitrate," *Current Biology* 9(17):R628-R629, 1999.

Wachter et al., "Structural basis of spectral shifts in the yellow-emission variants of green fluorescent protein," *Structure* 6:1267-1277, 1998.

Wang et al., "Increased expression of human calcium-activated chloride channel 1 gene is correlated with mucus overproduction in Chinese asthmatic airway," *Cell Biology International* 31:1388-1395, 2007.

Wang et al., "Increased expression of human calcium-activated chloride channel 1 is correlated with mucus overproduction in the

(56) References Cited

OTHER PUBLICATIONS airways of Chinese patients with chronic obstructive pulmonary disease," *Chinese Medicinal Journal* 120(12):1051-1057, 2007.

Worrell et al., "CaMKII mediates stimulation of chloride conductance by calcium in T84 cells," *Am. J. Physiol.* 260:C877-C882, 1991.

Yang et al., "Nanomolar Affinity Small Molecule Correctors of Defective ΔF508-CFTR Chloride Channel Gating," *The Journal of Biological Chemistry* 278(37):35079-35085, 2003.

Yang et al., "TMEM16A confers receptor-activated calcium-dependent chloride conductance," *Nature* 455:1210-1215, 2008.

Yangthara et al., "Small-Molecule Vasopressin-2 Receptor Antagonist Identified by a G-Protein Coupled Receptor "Pathway" Screen," *Molecular Pharmacology* 72(1):86-94, 2007.

Yasuo et al., "Relationship between Calcium-Activated Chloride Channel 1 and Mucsac in Goblet Cell Hyperplasia Induced by Interleukin-13 in Human Bronchial Epithelial Cells," *Respiration* 73:347-359, 2006.

Yoon et al., "Cloning and heterologous expression of a Ca2+-activated chloride channel isoform rat brain," *Biological and Pharmaceutical Bulletin* 29(11):2168-2173, 2006.

\* cited by examiner

INHIBITORS OF CALCIUM-ACTIVATED CHLORIDE CHANNELS

CROSS-REFERENCE TO RELATED APPLICATIONS

This application is continuation of U.S. application Ser. No. 13/601,216, filed Aug. 31, 2012; which is a continuation of U.S. application Ser. No. 12/747,468, filed Sep. 15, 2010, now abandoned; which is a national stage application filed under 35 U.S.C. §371 of International Patent Application No. PCT/US2008/086600 accorded an international filing date of Dec. 12, 2008; which claims the benefit under 35 U.S.C. §119(e) of U.S. Provisional Application No. 61/013,988, filed Dec. 14, 2007, all of which applications are incorporated herein by reference in their entirety.

STATEMENT OF GOVERNMENT INTEREST

This invention was made with government support under grant numbers DK72517, HL73854, EB00415, EY13574, DK35124, and DK43840 awarded by the National Institutes of Health. The government has certain rights in the invention.

BACKGROUND

Field

Agents are needed for treating diseases and disorders related to aberrant function of calcium-activated chloride channels, including, for example, increased intestinal fluid secretion, secretory diarrhea, asthma, and cystic fibrosis. Small molecule compounds that are potent inhibitors of chloride conductance via calcium-activated chloride channels and methods for identifying such compounds are described herein.

Description of the Related Art

Diarrheal disease in children is a global health concern: approximately four billion cases among children occur annually, resulting in two million deaths. Antibiotics are routinely used to treat diarrhea; however, the antibiotics are ineffective for treating many pathogens, and the use of these drugs contributes to development of antibiotic resistance in other pathogens.

Calcium-activated chloride channels (CaCCs) are believed to provide an important route for chloride (Cl$^-$) and fluid secretion in secretory diarrheas. Excess transepithelial salt and water transport by one or more CaCCs may be caused by certain drugs (e.g., antiretrovirals, chemotherapeutics) and viruses (see, e.g., Lorrot et al., *Virol. J.* 4:31 (2007); Morris et al., *Am. J. Physiol.* 277:G431-44 (1999); Rufo et al., *Am. J. Physiol.* 264:C998-1008 (2004); Schultheiss et al., *Eur. J. Pharmacol.* 546:161-70 (2006); Takahashi et al., *J. Med. Microbiol.* 49:801-10 (2000); Schultheiss et al., *J. Membr. Biol.* 204:117-27 (2005); Gyömörey et al., *Pflugers Arch.* 443 Suppl 1:S103-6 (2001); Kidd et al., *Annu. Rev. Physiol.* 62:493-513 (2000); Barrett et al., *Annu. Rev. Physiol.* 62:535-72 (2000)). The morbidity and mortality associated with secretory diarrhea indicate an imperative need for potent inhibitors of CaCCs.

In addition, CaCCs are believed to provide an important route for chloride (Cl$^-$) and fluid secretion in pulmonary diseases and disorders. For example, smooth muscle CaCCs have been implicated in the pathophysiology of asthma (see, e.g., Bolton et al., *J. Physiol.* 570:5-11 (2006); Farthing, *Dig. Dis.* 24:47-58 (2006); Thiagarajah et al., *Trends Pharmacol. Sci.* 26, 172-75 (2005))). Airway CaCCs have been identified in some model systems to be upregulated in cystic fibrosis (Tarran et al., *J. Gen. Physiol.* 120:407-18 (2002)), providing alternative chloride conductance to compensate for missing or defective CFTR. However, CaCC activity may contribute to excess mucus secretion by epithelial cells in the lungs of patients with pulmonary diseases and disorders, such as asthma, chronic obstructive pulmonary disease (COPD), bronchiectasis, and cystic fibrosis. Excess mucus production and concomitant change in the lung environment lead to colonization by bacteria that exacerbate the pathophysiology of the diseased lung. Thus, inhibitors of CaCCs are needed treating pulmonary diseases and disorders that exhibit mucus hypersecretion.

BRIEF SUMMARY

Briefly stated, provided herein are compounds, compositions, and methods that are useful for treating diseases and disorders related to or associated with aberrantly increased CaCC chloride secretion from cells. Also provided herein are methods for identifying and characterizing agents, including compounds, that inhibit calcium-activated chloride channels.

In one embodiment, compounds, and compositions comprising these compounds, of the aminothiophene class are provided. In one embodiment, the composition comprises a physiologically acceptable excipient and a compound having the following structure (I):

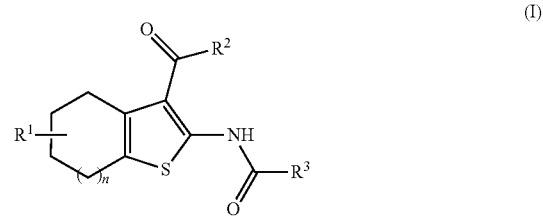

or a pharmaceutically acceptable salt, prodrug or stereoisomer thereof, wherein R$^1$ is hydrogen or optionally substituted alkyl; R$^2$ is hydroxy, optionally substituted alkoxy, or optionally substituted phenylamino; R$^3$ is optionally substituted alkyl, optionally substituted alkenyl, optionally substituted cycloalkyl, optionally substituted phenyl, or optionally substituted heterocyclyl; and n is 0, 1, or 2, and wherein the compound of structure I comprises at least one —COOH. Also provided herein in certain embodiments (described in greater detail herein), are aminothiophene compounds and compositions comprising these compounds wherein the aminothiophene compounds have a substructure of formulae (IA) and (Ia)-(Ii).

In another embodiment, compounds and compositions comprising these compounds, of the aminothiazole class are provided. In one embodiment, the composition comprises a physiologically acceptable excipient and a compound having the following structure (II):

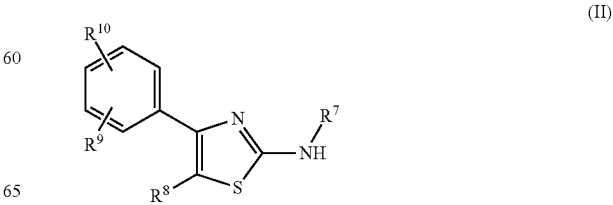

or a pharmaceutically acceptable salt, prodrug or stereoisomer thereof, wherein $R^7$ is optionally substituted $C_{1-6}$ alkyl, optionally substituted phenyl, or optionally substituted phenylacyl; $R^8$ is hydrogen, optionally substituted $C_{1-6}$ alkyl, or optionally substituted phenyl; $R^9$ and $R^{10}$ are the same or different and independently hydrogen, optionally substituted alkyl, optionally substituted alkoxy, or optionally substituted phenoxy. Also provided herein in certain embodiments (described in greater detail herein), are aminothiazole compounds and compositions comprising these compounds wherein the aminothiazole compounds have a substructure of formulae (IIa)-(IIh).

Also provided herein is a method of inhibiting a calcium-activated chloride channel comprising: contacting (a) a cell that comprises the calcium-activated chloride channel and (b) a compound or a composition comprising the compound wherein the compound is (i) an aminothiophene compound of structure (I), including substructures (IA) and (Ia)-(Ii) described above and herein and/or (ii) an aminothiazole compound of structure (II), including substructures (IIa)-(IIh) as described above and herein, in an amount effective and under conditions and for a time sufficient to inhibit activation of the channel. In a specific embodiment, the cell is an epithelial cell. In a particular embodiment, the epithelial cell is an intestinal epithelial cell or a lung epithelial cell. In a specific embodiment, the calcium-activated chloride channel is TMEM16A, and in other specific embodiments, the TMEM16A calcium-activated chloride channel is a human TMEM16A calcium-activated chloride channel.

In one embodiment, provided herein is a method of inhibiting fluid secretion from a cell comprising administering to a subject of the composition comprising physiologically acceptable excipient and (i) an aminothiophene compound of structure (I), including substructures (IA) and (Ia)-(Ii) described above and herein and/or (ii) an aminothiazole compound of structure (II), including substructures (IIa)-(IIh), in an amount effective to inhibit conductance of chloride through a calcium-activated chloride channel, thereby inhibiting fluid secretion from the cell, wherein the subject has a condition, disease or disorder that is treatable by inhibiting conductance of chloride through a calcium-activated chloride channel. In certain embodiments, the disease or disorder is selected from abnormally increased intestinal fluid secretion, secretory diarrhea, asthma, chronic obstructive pulmonary disease, bronchiectasis, or cystic fibrosis. In other embodiments, a condition that is treatable by inhibiting conductance of chloride through a calcium-activated chloride channel includes abnormally increased mucus secretion, which in certain embodiments is a condition of a disease or disorder that is a pulmonary disorder (e.g., asthma, chronic obstructive pulmonary disease, bronchiectasis, or cystic fibrosis).

In another embodiment, a method of treating a condition, disease, or disorder associated with abnormally increased chloride ion secretion is provided, wherein the method comprises administering to a subject a composition comprising a physiologically acceptable excipient and (i) an aminothiophene compound of structure (I), including substructures (IA) and (Ia)-(Ii) described above and herein and/or (ii) an aminothiazole compound of structure (II), including substructures (IIa)-(IIh) described above and herein, in an amount effective to inhibit a calcium-activated chloride channel, thereby inhibiting chloride ion secretion. In one certain embodiment, the disease or disorder is abnormally (i.e., aberrantly) increased intestinal fluid secretion. In a particular embodiment, the disease or disorder is secretory diarrhea. In another particular embodiment, the condition, which may be a condition of the disease or disorder described herein is abnormally increased mucus secretion. In certain embodiments, a disease or disorder that comprises the condition of abnormally increased mucus secretion is asthma, chronic obstructive pulmonary disease, bronchiectasis, or cystic fibrosis. In certain embodiments, the method of treating a disease or disorder further comprising administering to the subject an agent that inhibits ion transport by a cystic fibrosis transmembrane conductance regulator (CFTR). In a specific embodiment, the agent is a thiazolidinone compound. In a more specific embodiment, the thiazolidinone compound is 3-[(3-trifluoromethyl)phenyl]-5-[(4-carboxyphenyl)methylene]-2-thioxo-4-thiazolidinone.

Also provided herein is a use of a composition comprising (i) an aminothiophene compound of structure (I), including substructures (IA), (Ia)-(Ii) described above and herein and/or (ii) an aminothiazole compound of structure (II), including substructures (IIa)-(IIh) described above and herein, for treating a condition, disease, or disorder associated with abnormally increased chloride ion secretion from a cell. In specific embodiments, the disease or disorder is secretory diarrhea, asthma, chronic obstructive pulmonary disease, bronchiectasis, or cystic fibrosis. In other certain embodiments, a use is provided that is a use of a composition comprising a physiologically acceptable excipient (i) an aminothiophene compound of structure (I), including substructures (IA), (Ia)-(Ii) described above and herein and/or (ii) an aminothiazole compound of structure (II), including substructures (IIa)-(IIh) described above and herein, and a composition comprising an agent that inhibits ion transport by a cystic fibrosis transmembrane conductance regulator (CFTR). In a specific embodiment, the agent is a thiazolidinone compound. In a more specific embodiment, the thiazolidinone compound is 3-[(3-trifluoromethyl)phenyl]-5-[(4-carboxyphenyl)methylene]-2-thioxo-4-thiazolidinone.

In another embodiment, use of a composition is provided wherein the use comprises (i) an aminothiophene compound of structure (I), including substructures (IA), (Ia)-(Ii) described above and herein and/or (ii) an aminothiazole compound of structure (II), including substructures (IIa)-(IIh) described above and herein, for the manufacture of a medicament for treating a condition, disease, or disorder associated with abnormally increased chloride ion secretion from a cell. In a certain embodiment, the cell is an epithelial cell. In a particular embodiment, the epithelial cell is an intestinal or lung epithelial cell. In specific embodiments, the disease or disorder is secretory diarrhea, asthma, chronic obstructive pulmonary disease, bronchiectasis, or cystic fibrosis. In other certain embodiments, a use is provided that is a use of a composition comprising (i) an aminothiophene compound of structure (I), including substructures (IA), (Ia)-(Ii) described above and herein and/or (ii) an aminothiazole compound of structure (II), including substructures (IIa)-(IIh) described above and herein, and a composition comprising an agent that inhibits ion transport by a cystic fibrosis transmembrane conductance regulator (CFTR) for the manufacture of the medicament. In a specific embodiment, the agent is a thiazolidinone compound. In a more specific embodiment, the thiazolidinone compound is 3-[(3-trifluoromethyl)phenyl]-5-[(4-carboxyphenyl)methylene]-2-thioxo-4-thiazolidinone.

Also provided herein is a method of identifying an agent that is an inhibitor of a calcium-activated chloride channel comprising: (a) contacting a cell and a candidate agent in a test sample, (under conditions and for a time sufficient) to permit interaction between the candidate agent and the cell, wherein the cell comprises (i) a calcium-activated chloride channel and (ii) a cytoplasmic indicator protein that binds halide; (b) adding to the test sample (i) at least one calcium-elevating agonist and (ii) iodide, under conditions and for a time sufficient for the calcium-elevating agonist to bind to the cell (i.e., to permit binding of the calcium-elevating agonist to the cell), wherein binding of the calcium-elevating agonist to the cell increases the level of calcium ion ($Ca^{2+}$) in the cell; and (c) determining the level of iodide influx in the presence of the candidate agent and comparing the level of iodide influx in the presence of the candidate agent with the level of iodide influx in the absence of the candidate agent, wherein a decrease in the level of iodide influx in the presence of the candidate agent compared with the level of iodide influx in the absence of the candidate agent, indicates that the candidate agent is an inhibitor of the calcium-activated chloride channel. In a certain embodiment, the cell is an epithelial cell. In a particular embodiment, the epithelial cell is an intestinal epithelial cell or a pulmonary epithelial cell. In a more particular embodiment, the intestinal epithelial cell is an HT-29 cell. In certain embodiment, the steps of the method are performed in each of a plurality of reaction vessels in a high throughput screening array. In other particular embodiments, the calcium-elevating agonist is selected from histamine, calcimycin, ATP, carbachol, and forskolin. In a more specific embodiment, the test sample of step (b) is contacted with at least two, at least three, or at least four calcium-elevating agonists. In yet another specific embodiment, the test sample of step (b) is contacted with at least two calcium-elevating agonists, wherein the at least two calcium-elevating agonists are ATP and carbachol. In certain embodiments the calcium-activated chloride channel is TMEM16A; in specific embodiments, the TMEM16A is a mammalian TMEM16A; in other certain embodiments the mammalian TMEM16A is a human TMEM16A. In certain embodiments, the cytoplasmic indicator protein is a yellow fluorescent protein (YFP) variant (also called herein YFP mutant). In a particular embodiment, the YFP variant (also called herein YFP mutant) is YFP-H148Q/I152L. In still another embodiment, the epithelial cell comprising the cytoplasmic indicator protein is obtained by transforming, transfecting, or transducing the epithelial cell with a recombinant expression vector that comprises a polynucleotide that encodes the cytoplasmic indicator protein. In one specific embodiment, the cell transiently expresses the cytoplasmic indicator protein. In another specific embodiment, the cell stably expresses the cytoplasmic indicator protein. In still other embodiments, the recombinant expression vector is a plasmid or a viral vector. In a specific embodiment, the viral vector is a retroviral vector. In another specific embodiment, the retroviral vector is a lentiviral vector. In still another embodiment, step (c) comprises determining the level of iodide influx in the presence and absence of the candidate agent at multiple time points.

In another embodiment, a method is provided for determining influx of an anion in a cell that comprises or is suspected of comprising a calcium-activated chloride channel, wherein the anion is halide or $NO_3^-$, said method comprising: (a) contacting the cell with the anion in the presence of a calcium-elevating agonist and in the absence of the calcium-elevating agonist, under conditions and for a time sufficient that permit interaction between the calcium-elevating agonist and the epithelial cell, wherein the cell comprises a cytoplasmic indicator protein that binds the anion, and wherein binding of the calcium-elevating agonist to the cell increases the level of calcium ion ($Ca^{2+}$) in the cell; and (b) determining the level of anion influx in the presence of the calcium-elevating agonist and determining the level of anion influx in the absence of the calcium-elevating agonist and then comparing the level of anion influx in the presence of the calcium-elevating agonist to the level of anion influx in the absence of the calcium-elevating agonist, thereby determining influx of the anion in the cell. In a specific embodiment, the cell comprising the cytoplasmic indicator protein is obtained by transforming, transfecting, or transducing the epithelial cell with a recombinant expression vector that comprises a polynucleotide that encodes the cytoplasmic indicator protein. In a certain embodiment, the cell is an epithelial cell. In a particular embodiment, the epithelial cell is an intestinal epithelial cell or a pulmonary epithelial cell. In a more particular embodiment, the intestinal epithelial cell is an HT-29 cell. In certain embodiments the calcium-activated chloride channel is TMEM16A; in specific embodiments, the TMEM16A is a mammalian TMEM16A; in other certain embodiments the mammalian TMEM16A is a human TMEM16A. In one specific embodiment, the recombinant expression vector is a plasmid or viral vector. In another specific embodiment, the viral vector is a retroviral vector. In a certain embodiment, the retroviral vector is a lentiviral vector.

In another embodiment, a method is provided for determining influx of an anion in a cell that comprises or is suspected of comprising a calcium-activated chloride channel, wherein the anion is halide or $NO_3^-$, said method comprising: (a) culturing the cell to provide a plurality of cells; (b) transforming, transfecting, or transducing the plurality of cells a expression vector that comprises a polynucleotide encoding an indicator protein that is capable of binding the anion; (c) culturing the plurality of cells of step (b) under conditions and for a time sufficient that permit expression of the indicator protein in the cytoplasm of the cells; (d) contacting the plurality of cells with the anion in the presence and absence of a calcium-elevating agonist, under conditions and for a time sufficient to permit interaction between the calcium-elevating agonist and the plurality of cells, wherein binding of the calcium-elevating agonist to the plurality of cells increases the level of calcium ion ($Ca^{2+}$) in the plurality of cells; and (e) determining the level of anion influx in the presence of the calcium-elevating agonist and determining the level of anion influx in the absence of the calcium-elevating agonist, and then comparing the level of anion influx in the presence of the calcium-elevating agonist to the level of anion influx in the absence of the calcium-elevating agonist, thereby determining influx of anion in the cell. In a certain embodiment, the cell is an epithelial cell. In a particular embodiment, the epithelial cell is an intestinal epithelial cell or a pulmonary epithelial cell. In a more particular embodiment, the intestinal epithelial cell is an HT-29 cell. In certain embodiments the calcium-activated chloride channel is TMEM16A; in specific embodiments, the TMEM16A is a mammalian TMEM16A; in other certain embodiments the mammalian TMEM16A is a human TMEM16A. In one specific embodiment, the recombinant expression vector is a plasmid or viral vector. In another specific embodiment, the viral vector is a retroviral vector. In a certain embodiment, the retroviral vector is a lentiviral vector. In other specific embodiments, the indicator protein is a yellow fluorescent protein (YFP) mutant (also called herein YFP variant). In still another specific embodiment, the YFP mutant is YFP-H148Q/I152L. In certain embodiments, the step of determining the level of influx of the anion in the presence of the calcium-activated chloride channel agonist and determining the level of influx of the anion in the absence of the calcium-activated chloride channel agonist are determined at multiple time points (i.e., the step of determining comprises determining the level of influx of the anion in the presence of the calcium-activated chloride channel agonist and determining the level of influx of the anion in the absence of the calcium-activated chloride channel agonist at multiple time points over a time course). In still other embodiments, the calcium-elevating agonist is a first calcium-elevating agonist and is selected from histamine, calcimycin, ATP, carbachol, and forskolin. In a particular embodiment, the method further comprises a second calcium-elevating agonist. In certain particular embodiments, the first calcium-elevating agonist is ATP and the second calcium-elevating agonist is carbachol. Also, in specific embodiments of the method, the anion is iodide.

As used herein and in the appended claims, the singular forms "a," "and," and "the" include plural referents unless the context clearly dictates otherwise. Thus, for example, reference to "an agent" includes a plurality of such agents, and reference to "a cell" or "the cell" includes reference to one or more cells and equivalents thereof (e.g., plurality of cells) known to those skilled in the art, and so forth. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude in other certain embodiments, for example, that an embodiment of any composition of matter, composition, method, or process, or the like, described herein, may "consist of" or "consist essentially of" the described features.

BRIEF DESCRIPTION OF THE DRAWINGS

FIG. 1A illustrates a schematic of a cell-based, fluorescence high-throughput screening assay. In this example, calcium-activated chloride channel (CaCC)-facilitated iodide influx is measured from the kinetics of decreasing YFP-H148Q/I152L fluorescence in response to iodide addition to the extracellular solution. CaCC may be activated by a mixture of calcium-elevating agonists, including carbachol (Cch); carbachol receptor ($m_3$AChR); purinergic receptor ($P_{2Y2}$); and calcium-calmodulin protein kinase 2 (CaMKII). FIG. 1B is a fluorescence micrograph of lentivirus-infected HT-29 cells stably expressing the YFP iodide sensor.

FIG. 2C represents a carbachol concentration-response study. FIG. 2D demonstrates the initial negative fluorescence curve slope (following extracellular iodide addition) as a function of time after carbachol/ATP (each 100 µM) addition and extracellular iodide addition.

FIG. 3A (left) shows a time course of YFP fluorescence in HT-29 cells following iodide addition in the absence or presence of carbachol (100 µM) and ATP (100 µM). FIG. 3A (right) is a histogram distribution of initial iodide influx rates ($d[I^-]/dt$) determined from initial fluorescence slopes. FIG. 3B (left) provides examples of fluorescence data for individual compounds in the primary screen. FIG. 3B (right) is a histogram distribution of percentage inhibition from primary compound screening. Dashed vertical line denotes selection criteria for further evaluation. FIG. 3C describes structures of compounds of classes A-F identified from the primary compound screen.

FIG. 4A shows one example of the synthesis of $CaCC_{inh}$-A01: 6-t-butyl-2-(furan-2-carboxamido)-4,5,6,7-tetrahydrobenzo[b]thiophene-3-carboxylic acid. FIG. 4B shows one example of the synthesis of $CaCC_{inh}$-B01: 2-hydroxy-4-(4-p-tolylthiazol-2-ylamino)benzoic acid. FIG. 4C illustrates concentration-inhibition data for $CaCC_{inh}$-A01 and $CaCC_{inh}$-B01 determined by plate reader fluorescence assay.

FIG. 5A is a time course of YFP fluorescence in HT-29 cells following iodide addition in the absence or presence of thapsigargin in cells pre-treated with 30 µM of indicated compounds. FIG. 5B shows YFP fluorescence in FRT cells expressing human wildtype CFTR following iodide addition in cells pre-treated with 30 µM of indicated compounds. $CFTR_{inh}$-172 (20 µM) was present where indicated. FIG. 5C shows calcium signaling measured by fura-2 fluorescence in response to indicated agonists and test compounds. A=$CaCC_{inh}$-A01; B=$CaCC_{inh}$-B01. Representative data shown on the left, with averaged data on the right (SE, n=3-4). FIG. 5D shows ATP/carbachol-induced CaM-KII phosphorylation determined by immunoblot analysis (representative of 3 separate experiments).

FIG. 6A illustrates ionomycin-induced currents in the absence or presence of $CaCC_{inh}$-A01 or $CaCC_{inh}$-B01 recorded at a holding potential at 0 mV, and pulsing to voltages between ±120 mV in steps of 20 mV. FIG. 6B is a current/voltage (IN) plot of mean currents at the end of each voltage pulse as in A. FIG. 6C is a summary of current density data measured at Vm of +100 mV (S.E., n=6-8). FIG. 6D (top) illustrates ionomycin-induced chloride currents in the whole-cell configuration with symmetrical NMDG-Cl solutions. FIG. 6D (bottom) shows the current/voltage plot of mean currents at the end of each voltage pulse.

In FIG. 7A, after carbachol stimulation, ATP-induced $I_{sc}$ was measured in the absence or presence of inhibitors (representative of 3 or more separate experiments). FIG. 7B represents a summary of carbachol and ATP-induced short-circuit current in the absence or presence of $CaCC_{inh}$-A01 or $CaCC_{inh}$-B01 (S.E., n=3-4). *$P<0.05$ vs. control.

DETAILED DESCRIPTION

Figure 1A:
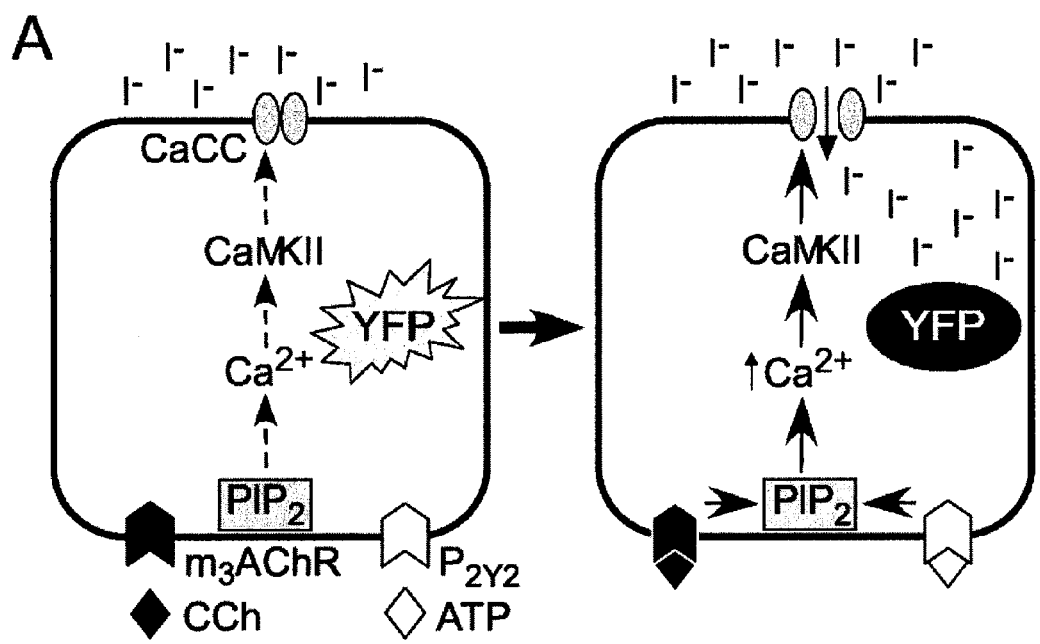
FIG. 1A-1B.

The disclosure herein relates to identification of specific and potent compounds that inhibit (i.e., block) calcium-activated chloride channels (CaCCs) such that chloride movement through these channels in inhibited. These compounds, and compositions comprising these compounds may be useful for treating secretory diarrheas and for treating pulmonary diseases and disorders that exhibit and are exacerbated by excess mucus production (i.e., mucus hypersecretion), such as asthma, cystic fibrosis, chronic obstructive pulmonary disease (COPD), and bronchiectasis. Also described herein are methods that were developed for identifying such compounds that inhibit or block calcium-activated chloride channels.

Calcium-activated chloride channels (CaCCs) are widely expressed in mammalian tissues, including intestinal and lung epithelia, where they facilitate fluid secretion. Fluid secretion is an important mechanism for maintaining normal function of the lungs, and intestinal tract, as well as other body organs, and is regulated, in part, by chloride ($Cl^-$) movement across the cell membrane.

Aberrantly increased secretion of chloride ion and water from a lung cell or intestinal cell, for example, may be facilitated by increased conductance of chloride ion through one or more CaCC(s). Excess chloride and water secretion from intestinal epithelial cells occurs in secretory diarrheas that may be caused by administration of particular drugs (e.g., antiretroviral drugs or chemotherapeutic drugs) and by various viruses, bacteria, and toxins. Aberrantly increased (or abnormally increased) secretion of chloride ion and water from a cell, such as a lung cell or intestinal cell, therefore refers to increased secretion of chloride ion and water from a cell compared with the amount or level of chloride ion and water secreted from a cell that exhibits normal function, such as in a subject who does not have or exhibit symptoms of conditions, diseases, and disorders discussed herein, such as secretory diarrhea and certain chronic lung diseases (e.g., cystic fibrosis, COPD, bronchiectasis, asthma).

Available compounds that inhibit CaCCs, including fenamates, anthracene-9-carboxylic acid, indoleacetic acid, ethacrynic acid, and tamoxifen, have low potency and inhibit multiple types of $Cl^-$ channels and transporters, and in some cases cause activation of $BK_{Ca}$ $K^+$ channels (see, e.g., Hartzell et al., *Annu. Rev. Physiol.* 67:719-58 (2005)). Despite the need for potent, selective CaCC inhibitors, none has yet been available (see, e.g., reviews by Kidd et al., supra; Hartzell et al., supra).

At least five distinct classes of mammalian $Cl^-$ channels, including the cystic fibrosis transmembrane conductance regulator (CFTR), CLC-type voltage-sensitive $Cl^-$ channels, ligand-gated (GABA and glycine) $Cl^-$ channels, volume-sensitive $Cl^-$ channels, and calcium-activated $Cl^-$ channels (CaCCs) have been identified (Hartzell et al., supra; Eggermont, *Proc. Am. Thorac. Soc.* 1:22-7 (2004)). The molecular identities of epithelial cell CaCCs remain unclear. Recently, a member of a group of plasma membrane proteins with previously unknown function, referred to as TMEM16A, has been identified as associated with calcium-dependent chloride current (see, e.g., Schroeder et al., *Cell* 134:1019-29 (2008); Caputo et al., *Science* 322:590-94 (2008); Yang et al., *Nature* 455:1210-15 (2008)). Potential candidates include bestrophins (Best1-Best4), CLCs of the CKCA family, and products of the recently described tweety gene (Suzuki, *Exp. Physiol.* 91:141-7 (2006); Hartzell et al., *Physiol. (Bethesda)* 20:292-302 (2005); Loewen et al., *Physiol. Rev.* 85:1061-92 (2005); Evans et al. J. Biol. Chem. 279:41792-800 (2004)). Agents that inhibit at least one CaCCs would therefore also be useful for characterizing and identifying CaCCs. Specific compounds, such as the compounds described herein, may be useful for identifying CaCCs physiologically and may be used to isolate specific currents from a mixture of currents. Such compounds may also be useful for characterizing the pore (e.g., resolving the structure of the pore), analyzing tissue and cell type distribution of CaCCs, and for biochemical analysis and manipulation.

Methods for Identifying Calcium-Activated Chloride Channel Inhibitors

Methods are provided herein for identifying agents that are inhibitors (i.e., agents that inhibit, block, prevent, interfere with, abrogate, or decrease activity or activation in a statistically or biologically significant manner) of at least one (i.e., one or more) CaCCs, thereby inhibiting movement of an anion, particularly chloride, from a cell (i.e., efflux or secretion from the cell). Thus, agents identified in the methods described herein (including the aminothiophene and aminothiazole compounds described herein) inhibit chloride conductance (or current) through a CaCC. The methods also include high throughput formats that are useful for screening large numbers of candidate agents to identify agents that are CaCC inhibitors.

Provided herein are methods to identify inhibitors (e.g., small molecule inhibitors) of one or more mammalian (particularly human) CaCCs and that thereby inhibit chloride and/or water secretion from a cell. The methods may be used to identify inhibitors that inhibit the channel itself (i.e., bind to or block the CaCC) or that inhibit by targeting a site or sites distal to calcium elevation. In a certain specific embodiment, a cell-based assay is provided that determines iodide influx in a monolayer of yellow fluorescent protein (YFP)-expressing cells (such as mammalian epithelial cells) in response to one or more calcium-elevating agonists. In certain embodiments, the methods described herein may also include agonists that prevent or minimize identification of compounds that inhibit at a target site or sites proximal to cell calcium elevation.

In certain embodiments, methods described herein for identifying an agent that inhibits a CaCC (i.e., that inhibits activation of a CaCC) and methods for determining anion influx include iodide as the anion. Iodide is useful in the methods described herein, particularly in initial screening of large numbers of agents because iodide is transported by channels, as opposed to being transported by either exchangers or cotransporters, such as AE1 ($Cl^-/HCO_3^-$) and NKCC ($Na^+/K^+/2Cl^-$). In addition, compared to chloride, iodide demonstrates greater quenching compared with presently available molecular and chemical halide sensors (see, e.g., Verkman et al., *Methods Mol. Med.* 70:187-96 (2002); Hartzell et al., *Annu. Rev. Physiol.* 67:719-58 (2005); Eggermont, *Proc. Am. Thorac. Soc.* 1:22-7 (2004); each of these references are hereby incorporated by reference in their entirety). Accordingly, as additional chemical and macromolecular halide sensors become available, additional halides may be used in these methods to determine anion flux.

In one embodiment, methods for identifying an agent that is an inhibitor of a calcium-activated chloride channel comprise contacting (i.e., combining in some manner that permits interaction between components in the method) a cell, particularly such as an epithelial cell, and a candidate agent to provide a test sample (i.e., mixture, combination), under conditions and for a time sufficient to permit interaction between the candidate agent and the cell, wherein the cell comprises a calcium-activated chloride channel and also comprises a cytoplasmic indicator protein that binds halide. To the test sample of the cells and the candidate agent is added at least one calcium-elevating agonist and a halide (e.g., $Cl^-$, $I^-$, $Br^-$, or $F^-$) or $NO_3^-$ (i.e., a source of halide or $NO_3^-$) other than chloride, such as iodide. In certain embodiments, the candidate agent is added prior to contacting the cells with the at least one calcium-elevating agent and a halide or $NO_3^-$. In other embodiments, the candidate agent is added contemporaneously with or subsequently to the at least one calcium-elevating agonist and a halide or $NO_3^-$. The halide or $NO_3^-$ is in a solution that lacks chloride (e.g., a phosphate buffered iodide solution). The at least one calcium-elevating agonist is added in an amount sufficient that upon binding to or interacting with the cell, the level of intracellular calcium ion ($Ca^{2+}$) increases in the cell, and results in activation (i.e., opening) of a calcium-activated chloride channel. In the absence of an inhibitor of the CaCC, activation of the channel results in increased influx of the anion (e.g., iodide). The capability of the candidate agent to inhibit influx of the anion is determined by determining and then comparing the level of anion influx in the presence and the level of anion influx in the absence of the candidate agent. A decrease in the level of anion influx in the presence of the candidate agent compared with the level of anion influx in the absence of the candidate agent indicates that the candidate agent inhibits the movement of the anion (i.e., inhibits anion current or conductance of the anion through the channel). As described in greater detail herein, the level of anion influx may be determined by determining the level of binding of the anion (e.g., iodide) to the cytoplasmic indicator protein. An exemplary cytoplasmic indicator protein is a halide sensor chromophore such as yellow fluorescent protein, or a mutant (i.e., variant) thereof, that upon binding to or interacting with the anion, the fluorescent signal is quenched (i.e., decreased). The change in the fluorescent signal may be determined at multiple time points over a time course (i.e., length of time) to provide time course data for determining anion influx. In a certain embodiment, the cells are epithelial cells, and in certain specific embodiments, the epithelial cells endogenously express at least one CaCC. In other embodiments of any one of the methods described herein, a cell (such as an epithelial cell) may be transfected, transformed, or transduced with a recombinant expression vector that comprises a polynucleotide that encodes a CaCC as discussed in further detail herein.

As discussed in greater detail herein, a test sample may be contained within any one of a variety of vessels that can include cells, buffer, and/or media, and components of the assay. By way of example, the cells may be adherent cells that are attached to (or adhered to) a well of a cell culture plate. The differing components (e.g., candidate agent(s), calcium-elevating agonist(s), halide, $NO_3^-$, etc.) used in the methods described herein may be contacted with the cells by addition of a component to a solution, or as a solution, in which the cells are bathed (i.e., supernatant). Each of the steps of the methods described herein are performed under conditions and for a time sufficient appropriate for each step. Such conditions and time are discussed herein and in the exemplary methods provided in the examples, and which may be readily determined by persons skilled in the art.

As described in greater detail below, the cell (e.g., an epithelial cell) comprising the cytoplasmic indicator protein is obtained by transforming, transfecting, or transducing the epithelial cell with a recombinant expression vector that comprises a polynucleotide that encodes the cytoplasmic indicator protein.

In a more specific embodiment, a method for identifying an agent that is an inhibitor of a calcium-activated chloride channel (CaCC) comprises contacting (i.e., combining in some manner that permits interaction between components in the method) an epithelial cell, and a candidate agent to provide a test sample (or combination or mixture), under conditions and for a time sufficient to permit interaction between the candidate agent and the epithelial cell, wherein the epithelial cell comprises a calcium-activated chloride channel and also comprises a cytoplasmic indicator protein that binds a halide, such as iodide. Subsequent to a time sufficient for the epithelial cells and agent to interact, the test sample (or combination or mixture) of the epithelial cells and the candidate agent are then contacted with at least one calcium-elevating agonist and iodide under conditions and for a time sufficient for the calcium-elevating agonist and epithelial cell to interact. Iodide is added to the test sample containing epithelial cells in the absence of a source of chloride (e.g., for example, sodium chloride is not included in buffers, media, or other reagents). An exemplary source of iodide is a phosphate buffer comprising iodide. Iodide may be added at concentrations between 10 mM and 200 mM depending upon the combination of cells, calcium-elevating agonist(s), agents, CaCC(s) expressed by the cells, and other components and conditions (such as media) that are used in the method. The at least one calcium-elevating agonist is added in an amount sufficient that upon binding or interacting to the cell, the level of intracellular calcium ion ($Ca^{2+}$) increases in the cell, causing activation (i.e., opening) of a calcium-activated chloride channel. In the absence of an inhibitor of the CaCC, activation of the channel results in increased influx of iodide. The capability of the candidate agent to inhibit influx of iodide is determined by determining and then comparing the level of iodide influx in the presence of the candidate agent and the level of iodide influx in the absence of the candidate agent. A decrease in the level of iodide influx in the presence of the candidate agent compared with the level of iodide influx in the absence of the candidate agent indicates that the candidate agent inhibits the movement of the iodide (i.e., inhibits anion current or conductance of the anion through the channel).

As described above, the level of anion (e.g., iodide) influx may be determined by determining (i.e., in some manner measuring) the level of binding of iodide to the cytoplasmic indicator protein. An exemplary cytoplasmic indicator protein is a halide sensor chromophore such as yellow fluorescent protein, or a mutant or variant thereof, that upon binding or interaction of iodide, the fluorescent signal is quenched (i.e., decreased). The change in the fluorescent signal may be determined at multiple time points to provide time course data for determining iodide influx. The fluorescent signal can be detected by any one of numerous commercially available apparatus.

Calcium-activated chloride channels are activated by cytosolic calcium ion ($Ca^{2+}$). The $Ca^{2+}$ that activates a CaCC may come from either $Ca^{2+}$ influx or from $Ca^{2+}$ release from intracellular stores. Without wishing to be bound by any particular theory, a CaCC may be activated by direct $Ca^{2+}$ binding or may act indirectly on the CaCC by binding to $Ca^{2+}$ binding proteins or $Ca^{2+}$ dependent enzymes. Certain CaCCs may be stimulated by protein phosphorylation that involves calcium-calmodulin-dependent kinase II. Experimentally, cytosolic $Ca^{2+}$ may be induced by stimulating cells with $Ca^{2+}$ elevating agonists and by $Ca^{2+}$ ionophores, such as ionomycin (see, e.g., Eggermont, supra; Kidd et al., supra). Exemplary calcium-elevating agonists that may be used in the methods described herein include but are not limited to histamine, calcimycin, ATP, carbachol, and forskolin. Without wishing to be bound by any particular theory, the calcium elevating agonist binds to a cognate receptor on the cell, which triggers phosphoinositide signaling, which in turn activates calcium-calmodulin-dependent kinase II. The cognate receptor of the calcium-elevating agonist, carbachol, is a muscarinic cholinergic receptor ($m_3AchR$). ATP, acting as a calcium-elevating agonist binds to purinergic receptor ($P_{2Y2}$). In certain embodiments, one calcium-elevating agonist is contacted with the cells (e.g., epithelial cells). In a specific embodiment, the calcium-elevating agonist is carbachol or ATP. In other certain embodiments, at least two calcium-elevating agonists are contacted with the cells. In certain other embodiments, at least three or at least four calcium-elevating agonists are included in the methods described herein. In a specific embodiment, at least two calcium-elevating agonists, for example, carbachol and ATP, are contacted with the cells in a manner that permits interaction between the cells and each of the agonists.

Whether a single agonist or multiple agonists (i.e., at least two, three, or four agonists) are used in a screening assay for identifying CaCC inhibitors may depend on the particular cell (including the particular epithelial cell or cell line) that is used in the screening method. Selection of one or more appropriate calcium-elevating agonists can be determined by using the methods described herein for determining anion influx in a cell (e.g., an epithelial cell) in the presence and absence of the agonist. The concentration of the one or more calcium-elevating agonists that are contacted with cells to elevate cytosolic $Ca^{2+}$ can be determined according to methods routinely practiced by a skilled artisan when optimizing assay methods; typically a calcium-elevated agonist is added to cells (e.g., epithelial cells) at a concentration between 10-100 µM.

A person skilled in the art also readily appreciates that appropriate controls can be designed and included when performing the in vitro methods described herein. For example, a method for identifying an agent that inhibits a CaCC and that inhibits influx of an anion (e.g., iodide) includes a sample or samples that comprise a plurality of cells (e.g., epithelial cells) and one or more candidate agents and includes one or more control samples. Controls may include samples that are used to determine the basal iodide conductance (or the basal level of another halide or nitrate conductance for which influx is determined), which is the conductance observed in the absence of a calcium-elevated agonist, which is the calcium-chloride channel-independent conductance. Additional controls that may be included in the methods for identifying an agent are samples that comprise the vehicle (i.e., solvent, buffer, or solution) in which the agent is prepared but lacks the agent (negative control). Instead of or in addition to the aforementioned negative control, a sample may include an agent or compound that is known not to inhibit CaCC and not to alter anion flux. Accordingly, determining anion (e.g., iodide) flux in the presence and absence of an agent is understood to mean that a first sample comprises all assay components (including the agent) and at least one additional sample (i.e., a second, third, fourth, and/or fifth sample etc.) comprises all components except the agent, respectively. The composition of control samples (i.e., including (in the presence of) or excluding (in the absence of) certain components) and the time at which the control samples are prepared and evaluated are described herein and can also be readily determined by a person skilled in the assay method art. Conditions for a particular assay include temperature, buffers (including salts, cations, media), and other components that maintain the integrity of the cell, the agent, the calcium-elevating agonist, with which a person skilled in the art will be familiar and/or which can be readily determined. Analysis of positive and negative controls may be included in any method prior to, concurrently with, or subsequent to determining the ability of an agent to inhibit CaCC(s).

Reference to "an agent" or "a candidate agent" includes a plurality of such agents. Accordingly, as described herein a sample comprising cells (e.g., epithelial cells) and an agent may comprise one, two, three, four, or any number of agents between 1 and 10 or 1 and 50. As routinely practiced in the art for screening libraries of agents, multiple agents may be included in a single sample, the method performed, positive "hits" selected, and a subsequent assay performed in which a lesser number of agents are included per sample. The methods are repeated until the method is performed with a single agent per sample.

With respect to the methods discussed above and herein, reference to "a cell" is not necessarily limited to a single cell but is intended to include at least one cell (i.e., one or more cells) or a plurality of cells. Reference to "contacting" in the steps of the methods described herein includes incubating, immersing, exposing, bathing, combining, mixing, adding together, or otherwise introducing one component (e.g., a cell, candidate agent, halide (e.g., iodide) or $NO_3^-$, agonist such as a calcium-elevating agonist, or any other component described herein) of the method with another component. The steps of the methods described herein are performed under conditions and for a time sufficient As used herein, movement of a halide, such as chloride or iodide or other anion, across and through the outer cell membrane from the extracellular space or environment into the cell refers to influx of the halide. Movement of a halide, such as chloride or iodide or other anion, out of the cell into the extracellular space refers to efflux of the halide.

As described herein, the cells (e.g., epithelial cells) comprise at least one CaCC. Other chloride channels (e.g., cystic fibrosis transmembrane conductance regulator protein (CFTR); CLC-type voltage-sensitive chloride channels; ligand gated (GABA and glycine) chloride channels; and volume-sensitive channels) may be expressed in the cell in addition to one or more CaCCs. The methods described herein, may therefore, further comprise contacting the cells (e.g., epithelial cells) with one or more bioactive agents that inhibit one or more chloride channels but that do not inhibit CaCCs. For example, certain cells, including epithelial cells and epithelial cell lines, may express cystic fibrosis transmembrane conductance regulator protein (CFTR) in addition to at least one CaCC. Accordingly, an inhibitor of CFTR may be contacted with the cells to block or inhibit transport of chloride or other halide through CFTR. Exemplary inhibitors of CFTR include, but are not limited to thiazolidinone compounds (e.g., 3-[(3-trifluoromethyl)phenyl]-5-[(4-carboxyphenyl)methylene]-2-thioxo-4-thiazolidinone (referred to herein as $CFTR_{inh}$-172) and hydrazide compounds (see, e.g., U.S. Pat. No. 7,235,573; U.S. Patent Application Publication No. 2005-0239740; Muanprasat et al., *J. Gen. Physiol.* 124:125-37 (2004); Ma et al., *J. Clin. Invest.* 110:1651-58 (2002)).

The methods described herein have value in high throughput screening, that is, in automated screening of a large number of candidate agents that inhibit calcium-activated chloride channels and that are thus useful for inhibiting chloride secretion from a cell. The method may be used to screen synthetic or natural product libraries for bioactive agents and compounds. The methods described herein are therefore amenable to automated, cost-effective high throughput drug screening and have immediate application in a broad range of pharmaceutical drug development programs. In one embodiment, the agents to be screened are organized in a high throughput screening format such as using microfluidics-based devices, or a 96-well plate format, or other regular two dimensional array, such as a 384-well, 48-well or 24-well plate format, or an array of test tubes. The format is therefore amenable to automation. An automated apparatus that is under the control of a computer or other programmable controller may be used for one or more steps of the methods described herein. A controller can monitor the results of each step of the process and can automatically alter the testing paradigm in response to those results.

For high-throughput screening, the cells, such as epithelial cells, comprising at least one CaCC may be cultured and used in the methods described herein in any of a variety of containers or sample vessels, including test tubes, multi-well plates such as 48-well, 72-well, 96-well plates, 384-well plates or other such vessels, including those useful for high throughput screening formats wherein, for example, detection of fluorescence of the cytoplasmic indicator protein in a plurality or reaction vessels, may be automated. Epithelial cells are typically adherent cells in culture, and the surface to which the cells are adhered may be solid, such as a tissue culture plate (e.g., 24-well, 48-well, 72-well, 96-well plates, 384-well plate), or the cells may be adhered to microcarrier beads. Alternatively, the surface on which the cells adhere may be porous such that the apical cell surface and basolateral cell surface may be exposed to or bathed in the solutions described herein.

The number of samples to be assayed may influence the degree of automation that can be implemented. For example, when high throughput screening, (i.e., assaying a large number of samples in a relatively brief time period) is desired, robotic or semi-robotic instruments may be used. In certain instances, microfluidics multiplexing technologies may be employed (see, e.g., Thorsen et al., Science 298: 580-84 (2002); Manz and Becker, eds. *Microsystem Technology in Chemistry and Life Sciences* (Springer 1999); Zhang et al, *Microelectrofluidic Systems: Modeling and Simulation* (CRC Press 2002); Tabeling, *Introduction to Microfluidics* (Oxford University Press 2006); U.S. Pat. Nos. 6,969,850; 6,878,755; 6,454,924; 6,681,788; 6,284, 113). Alternatively, samples may be processed manually, even for formats that accommodate large sample numbers (e.g., 96-well microplates).

In a specific embodiment, a high throughput method is provided for identifying an agent that is an inhibitor of a calcium-activated chloride channel. In one embodiment, the method comprises culturing, in each of a plurality of reaction vessels in a high throughput screening array, a plurality of cells (e.g., epithelial cells), wherein the plurality of cells comprise (a) a calcium-activated chloride channel and (b) a cytoplasmic indicator protein that binds halide (and may also bind $NO_3^-$). As described above and herein, the plurality of cells in each of the plurality of reaction vessels, are contacted (i.e., combined with or in some manner permitted to interact with) a candidate agent under conditions and for a time sufficient to permit interaction between the candidate agent and the plurality of the cells, to form a test sample (or combination or mixture) in each of the plurality of reaction vessels. Subsequently added to each test sample in each reaction vessel is at least one calcium-elevating agonist and a halide or $NO_3^-$, under conditions and for a time sufficient for the calcium-elevating agonist to bind to the plurality of cells in each of the plurality of reaction vessels. In certain particular embodiments, the halide is iodide. Any one, two, or more of the calcium-elevating agonists described herein interacts with the plurality of cells for a time sufficient to increase the level of calcium ion ($Ca^{2+}$) in the plurality of cells. The level of halide (e.g., iodide) or $NO_3^-$ influx in the plurality of epithelial cells in each of the plurality of reaction vessels in the presence of the candidate agent is compared with the level of halide (e.g., iodide) or $NO_3^-$ influx in the absence of the candidate agent. A decrease in the level of halide (e.g., iodide) or $NO_3^-$ influx in the presence of the candidate agent compared with the level of halide (e.g., iodide) or $NO_3^-$ influx in the absence of the candidate agent, indicates that the candidate agent is an inhibitor of the calcium-activated chloride channel. In a certain embodiment, the cells are epithelial cells, and in certain specific embodiments, the epithelial cells endogenously express at least one CaCC.

Also provided herein are methods for determining anion (i.e., halide and nitrate ($NO_3^-$)) transmembrane movement (i.e., conductance or current) through calcium-activated chloride channels (CaCCs). These methods may be used to determine if a particular cell comprises a CaCC or to quantify the level of a CaCC expressed by the cell. The methods may also be useful for identifying and characterizing a CaCC that is endogenously or exogenously expressed by a cell. For example, for exogenous expression, a recombinant expression vector that comprises a polynucleotide (which polynucleotide is operatively linked to at least one expression control region, such as a promoter) that encodes a polypeptide believed to be or known to be a CaCC may be introduced into a cell by transformation, transfection, or transduction of a cell, such as an epithelial cell or other cell type, according to molecular biology and protein expression methods routinely practiced by person skilled in the art and described in detail herein (see, e.g., Ausubel et al. (*Current Protocols in Molecular Biology* (Greene Publ. Assoc. Inc. & John Wiley & Sons, Inc., 1993)); Sambrook et al. (*Molecular Cloning: A Laboratory Manual,* 3rd Ed., (Cold Spring Harbor Laboratory 2001)); Maniatis et al. (*Molecular Cloning,* (Cold Spring Harbor Laboratory 1982); see also discussion below with respect to cells that may be used in the methods described herein). The methods may also be useful for identifying and characterizing calcium-elevating agonists, singly or in combination, that effectively increase the level of calcium ion in the cell such that the calcium-activated CaCC(s) is activated and opens, permitting movement of anions through the channel.

In one embodiment, influx of an anion (such as a halide ($Cl^-$, $I^-$, $Br^-$, or $F^-$) or $NO_3^-$) in a cell, for example, an epithelial cell, that comprises or is suspected of comprising at least one CaCC (i.e., one or more CaCCs), may be determined by contacting (i.e., combining in some manner that permits interaction) the anion, the cell, and a calcium-elevating agonist under conditions and for a time sufficient that permit the calcium-elevating agonist to interact with the cell. Anion influx in the presence and absence of the calcium-elevating agonist is then determined. The cell comprises a cytoplasmic indicator protein that is capable of interacting with an anion (such as a halide ($Cl^-$, $I^-$, $Br^-$, or $F^-$) or $NO_3^-$) and thus acts as an anion sensor. As described above and herein, in particular embodiments, the anion is iodide ($I^-$).

In a more specific embodiment, a method is provided for determining (i.e., measuring or quantifying) influx of an anion, which is a halide ($Cl^-$, $I^-$, $Br^-$, or $F^-$) or $NO_3^-$, in epithelial cells that comprise or are suspected of comprising at least one CaCC (i.e., one or more CaCCs). The epithelial cells, which comprise a cytoplasmic indicator protein that binds to halides and $NO_3^-$ described in greater detail herein, are contacted with the anion and with a calcium-elevating agonist under conditions and for a time sufficient to permit the agonist to interact with the epithelial cell. Anion influx in the presence and absence of a calcium-elevating agonist is then compared. As described above and herein, in particular embodiments, the anion is iodide ($I^-$).

As described in greater detail below, the cell (e.g., an epithelial cell) comprising the cytoplasmic indicator protein is obtained by transforming, transfecting, or transducing the epithelial cell with a recombinant expression vector that comprises a polynucleotide that encodes the cytoplasmic indicator protein.

Cells. As described herein, methods are provided for determining influx of an anion through a CaCC that traverses the outer cell membrane of the cell, such as an epithelial cell, and for determining the capability of an agent to inhibit influx of the anion through the activated CaCC into the cell. As described in detail herein, epithelial cells may be used as the cells that comprise at least one CaCC and that comprise a cytoplasmic indicator protein in the methods for determining anion influx in the presence of a calcium-elevating agonist and in the methods for identifying an agent that inhibits anion influx in a cell. Desirable characteristics of the cells include the capability of the cells to grow efficiently on a solid support (particularly a plastic support) (e.g., cell culture plates and flasks routinely used for cell culture methods and reaction vessels that are used in high throughput screening methods); capability to remain adhered to the support during repeated changes of media and washing; efficient expression of the cytoplasmic indicator protein to provide a measurable difference in the signal (e.g., fluorescence) detected prior to anion influx and the signal detected after anion influx (e.g., influx of iodide) that can be precisely and accurately determined; efficient and strong CaCC chloride conductance (i.e., chloride current or movement through a CaCC); and low basal (i.e., CaCC-independent) conductance of the anion (e.g., iodide). Exemplary epithelial cells as described herein include HT-29 intestinal epithelial cells that, after infection with a lentiviral vector that encoded the cytoplasmic indicator protein YFP-H148Q/I152L, were brightly fluorescent and able to grow in confluent monolayers in culture.

Cells, such as epithelial cells, that may be used in the methods described herein may endogenously or exogenously express at least one CaCC. Cells that exogenously express a CaCC may be prepared according to molecular biology and protein expression methods routinely practiced in the art. For example, for exogenous expression, a recombinant expression vector that comprises a polynucleotide (which polynucleotide is operatively linked to at least one expression control region, such as a promoter) that encodes a polypeptide believed to be or known to be a CaCC may be introduced into a cell by transformation, transfection, or transduction of a cell, such as an epithelial cell or other cell type, according to molecular biology and protein expression methods routinely practiced by person skilled in the art and described in detail herein. Cell lines may be established that stably express the exogenously introduced CaCC, or cells may be used in the methods described herein that transiently express the CaCC.

By way of example, such an expression vector that includes a polynucleotide comprising a nucleotide sequence that encodes a CaCC referred to in the art as TMEM16A may be introduced into a cell, by molecular biology methods routinely practiced in the molecular biology art (see, e.g., Ausubel et al. (*Current Protocols in Molecular Biology* (Greene Publ. Assoc. Inc. & John Wiley & Sons, Inc., 1993)); Sambrook et al. (*Molecular Cloning: A Laboratory Manual*, 3rd Ed., (Cold Spring Harbor Laboratory 2001)); Maniatis et al. (*Molecular Cloning*, (Cold Spring Harbor Laboratory 1982)). The TMEM16A CaCC may be of mammalian origin (such as mouse, human, rat) or may be from a non-mammalian species or may be from algae. Polynucleotide sequences and the encoded polypeptide sequences for TMEM16A of different animals and plants are readily available from public databases. In certain embodiments, a polynucleotide encoding human TMEM16A (see, e.g., GenBankNM_018043.5) may be included in a recombinant expression vector wherein the encoding polynucleotide is operatively linked to at least one expression control sequence (e.g., a promoter). See also, for example, Schroeder et al., *Cell* 134:1019-29 (2008); Caputo et al., *Science* 322:590-94 (2008); Yang et al., *Nature* 455:1210-15 (2008)) (all of which are incorporated herein by reference in their entirety).

For maintaining viability of cells, including epithelial cells, the cells are cultured in media and under conditions practiced in the art for proper maintenance of cells in culture, including media (with or without antibiotics) that contains buffers and nutrients (e.g., glucose, amino acids (e.g., glutamine), salts, minerals (e.g., selenium)) and also may contain other additives or supplements (e.g., fetal bovine serum or an alternative formulation that does not require a serum supplement; transferrin; insulin; putrescine; progesterone) that are required or are beneficial for in vitro culture of cells and that are well known to a person skilled in the art (see, for example, GIBCO media, INVITROGEN Life Technologies, Carlsbad, Calif.). Similar to standard cell culture methods and practices, the cell cultures described herein are maintained in tissue culture incubators designed for such use so that the levels of carbon dioxide (typically 5%), humidity, and temperature can be controlled. The cell culture system may also comprise addition of exogenous (i.e., not produced by the cultured cells themselves) cell growth factors, which may be provided, for example, in the media or in a substrate or surface coating. Growth characteristics of the cells for use in the methods described herein, may be optimized by altering the composition or type of media, adjusting the amount of one or more nutrients and/or serum, which are procedure with which a skilled artisan is familiar. Persons skilled in the tissue culture art also recognize that conditions employed for routine maintenance of a cell culture (i.e., media, additives, nutrients) may need to be adjusted appropriately for certain manipulations of the cells (for example, successful introduction of a recombinant expression vector (plasmid or viral vector, including a retroviral vector); ensuring appropriate confluency and growth properties of cells for high throughput screening). By way of example, HT-29 cells are typically cultured in McCoy's 5a medium (see ATCC recommendation). After transduction with a lentiviral vector that comprises a polynucleotide that encodes the cytoplasmic indicator protein, the cells divide more rapidly and robustly in a different media, such as Dulbecco's Modified Eagle's Medium (DMEM).

In certain embodiments, the cell is epithelial cell, which is an intestinal epithelial cell; in other certain embodiments, the epithelial cell is a lung epithelial cell. Epithelial cells and other cell types may be obtained or derived from any one of a number of animals, including mammals. Mammalian cells may be obtained from humans; non-human primates; rodents such as mice, rats, or rabbits; cats (feline); dogs (canine); cattle (bovine); sheep (ovine); pigs (porcine); llamas; and camels, for example. The cells may be derived from a primary cell culture (e.g., lung epithelial cells or intestinal epithelial cells or other cells that endogenously express a CaCC), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like. Exemplary intestinal epithelial cells that may be used in the methods described herein are HT-29 cells (American Type Culture Collection, Manassas, Va.).

Cytoplasmic Indicator Protein. The cells that are used in the methods described herein, including epithelial cells such as HT-29 intestinal epithelial cells, comprise at least one CaCC that traverses the outer cell membrane of the cell. The cells further comprise a cytoplasmic indicator protein that is a halide sensor. In a specific embodiment, the cytoplasmic indicator protein is a chromophore, such as the green fluorescent protein variant (i.e., a mutant), called yellow fluorescent protein (e.g., YFP-H148Q) (see, e.g., Jayaraman et al. *J. Biol. Chem.* 275:6047-50 (2000); Galietta et al., *Am. J. Physiol. Cell Physiol.* 281:C1734-42 (2001); Ma et al., *J. Clin. Invest.* 110:1651-58 (2002); Muanprasat et al., *J. Gen. Physiol.* 124:125-37 (2004); Ma et al. *J. Biol. Chem.* 277: 37235-41 (2002); Yang et al., *J. Biol. Chem.* 278:35079-85 (2003); Ormo et al., *Science* 273:1392-95 (1996); Elsliger et al., *Biochemistry* 38:5296-301 (1999); Wachter et al., *Structure (Lond.* 6:1267-77 (1998); Wachter et al., *Curr. Biol.* 9:R628-29 (1999); Pedemonte et al., *J. Clin. Invest.* 115: 2564-71 (2005)). In certain specific embodiments, the cytoplasmic indicator protein is a yellow fluorescent protein mutant (i.e., variant) in which one or more additional amino acid have been substituted that confer particular desirable properties (for example, altering the level of fluorescence and/or altering the binding affinity of the yellow fluorescent protein for one or more halides). In a particular embodiment, a YFP mutant (i.e., variant), YFP-H148Q/I152Q, may be used for the methods described herein to identify an agent that inhibits CaCC(s) or for the methods to determine anion flux in a cell (see, e.g., Galietta et al., *FEBS Lett.* 499:220-24 (2001); Yangthara et al., *Mol. Pharmacol.* 72:86-94 (2007)). The YFP-H148Q/I152Q indicator protein has iodide and nitrate ($NO3^-$) sensitivities, which permit measurement of cellular halide movement by chloride/nitrate exchange or by chloride/iodide exchange using low iodide concentrations.

Epithelial cells, such as HT-29 cells, expressing a cytoplasmic indicator protein that is a yellow fluorescent protein (YFP), or mutant (i.e., variant) thereof (e.g., YFP-H148Q/I152Q) are brightly fluorescent (see FIG. 1). When an extracellular halide, such as iodide, is contacted with or added to cells that express a CaCC and a cytoplasmic indicator protein such as the yellow fluorescent protein, or mutant (i.e., variant) thereof, in the presence of at least one calcium-elevating agonist, influx of an extracellular halide is facilitated by a CaCC. Influx of the halide, such as iodide, is detected by fluorescent quenching of the YFP halide sensor (see the schematic in FIG. 1A). Thus in certain embodiments, iodide influx is determined by measuring fluorescence quenching of a cytoplasmic YFP-based halide sensor (YFP-H148Q/I152L).

Fluorescence may be quantified using any one of a number of fluorescence detection systems, including "plate readers" that detect the signal in individual wells of a multi-well plate, available from commercial vendors. The YFP indicator protein (YFP-H148Q/I152L) is approximately 50% quenched by approximately 3 mM iodide. As discussed herein, iodide may be added at concentrations between 10 mM and 200 mM depending upon the combination of cells, calcium-elevating agonist(s), agents, CaCC(s) expressed by the cells, and other components and conditions (such as media) that are used in the method.

For transient or stable expression of a cytoplasmic indicator protein (e.g., the YFP mutants (i.e., variants) thereof described herein, for example, YFP-H148Q/I152Q), cells that comprise at least one CaCC (endogenously or exogenously) may be transformed, transfected, or transduced with a recombinant expression vector that comprises a polynucleotide that encodes the cytoplasmic indicator protein. Plasmids that encode YFP mutants (i.e., variants) may be obtained from commercial sources (e.g., CLONTECH, Mountain View, Calif.) (for example, EYFP=GFP-S65G/V68L/S72A/T203Y). Additional substitutions of amino acids, such as substitution of histidine at position 148 with glutamine (H148Q) and substitution of isoleucine at position 152 with glutamine (I152Q) may be performed by site-directed mutagenesis methods routinely and commonly practiced by persons skilled in the art (see, e.g., Galietta et al. *FEBS Lett.* 499:220-24 (2001); Ausubel et al. (*Current Protocols in Molecular Biology* (Greene Publ. Assoc. Inc. & John Wiley & Sons, Inc., 1993)); Sambrook et al. (*Molecular Cloning: A Laboratory Manual*, 3rd Ed., (Cold Spring Harbor Laboratory 2001)).

In a specific embodiment of the methods described herein, cells, such as epithelial cells, including intestinal epithelial (e.g., the exemplary cell line, HT-29) and lung epithelial cells or epithelial cells derived from other tissues, comprise an exogenous polynucleotide that encodes the cytoplasmic indicator protein (e.g., YFP-H148Q/I152Q). The cells, (e.g., epithelial cells) may be transfected, transformed, or transduced with a recombinant expression vector, which comprises a polynucleotide that is capable of directing expression of the cytoplasmic indicator protein. To direct expression of the cytoplasmic indicator protein, the polynucleotide comprises a nucleotide sequence that encodes the cytoplasmic indicator protein, which nucleotide sequence is operatively linked to at least one expression control sequence (e.g., a promoter, enhancer, transcriptional control element, and the like). Recombinant expression vectors may be prepared according to methods and techniques with which a person skilled in the molecular biology art is familiar and which are described herein.

Cells (e.g., epithelial cells) containing the described recombinant expression constructs may be genetically engineered (transduced, transformed, or transfected) with vectors and/or expression constructs (for example, a cloning vector, a shuttle vector, or an expression construct). The vector or construct may be in the form of a plasmid, viral vector (which includes a viral particle), a phage, etc. The engineered cells can be cultured in conventional nutrient media modified as appropriate for activating promoters, selecting transformants, or amplifying particular genes or encoding-nucleotide sequences. For particular types of cells and particular cell lines, selection and maintenance of culture conditions such as temperature, pH and the like, will be readily apparent to the ordinarily skilled artisan. Preferably the cells, including epithelial cells, can be adapted to sustained propagation in culture to yield a cell line according to art-established methodologies. In certain embodiments, the cell line is an immortal cell line, which refers to a cell line that can be repeatedly passaged in culture (at least ten times while remaining viable) following log-phase growth. In other embodiments the cell that is used to generate a cell line is capable of unregulated growth, such as a cancer cell, or a transformed cell, or a malignant cell.

Useful recombinant expression constructs are prepared by inserting into an expression vector a structural DNA sequence encoding the polypeptide of interest, such as a cytoplasmic indicator protein or a CaCC, together with suitable translation initiation and termination signals in operable reading phase with a functional promoter. The construct may comprise one or more phenotypic selectable markers and an origin of replication to ensure maintenance of the vector construct and, if desirable, to provide amplification within the cell (e.g., an epithelial cell). A particular plasmid or vector may be used as long as it is replicable and viable in the cell. Thus, for example, the polynucleotides that encode a cytoplasmic indicator protein may be included in any one of a variety of expression vector constructs for expressing a polypeptide.

An appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. Numerous standard techniques are described, for example, in Ausubel et al. (*Current Protocols in Molecular Biology* (Greene Publ. Assoc. Inc. & John Wiley & Sons, Inc., 1993)); Sambrook et al. (*Molecular Cloning: A Laboratory Manual,* 3rd Ed., (Cold Spring Harbor Laboratory 2001)); Maniatis et al. (*Molecular Cloning,* (Cold Spring Harbor Laboratory 1982)), and elsewhere.

The nucleotide sequence encoding a protein of interest (e.g., a cytoplasmic indicator protein or a CaCC) in the expression vector is operatively linked to at least one appropriate expression control sequence (e.g., a promoter or a regulated promoter) to direct mRNA synthesis. Representative examples of such expression control sequences include LTR or SV40 promoter, the *E. coli* lac or trp, the phage lambda $P_L$ promoter, and other promoters known to control expression of genes in prokaryotic or eukaryotic cells or their viruses. Promoter regions can be selected from any desired gene using CAT (chloramphenicol transferase) vectors or other vectors with selectable markers. Eukaryotic promoters include CMV immediate early, HSV thymidine kinase, early and late SV40, LTRs from retroviruses, and mouse metallothionein-I. Selection of the appropriate vector and promoter and preparation of certain recombinant expression constructs comprising at least one promoter or regulated promoter operatively linked to a polynucleotide described herein is well within the level of ordinary skill in the art.

In certain embodiments, the recombinant expression construct that encodes the polypeptide of interest (e.g., a cytoplasmic indicator protein or a CaCc) is a retroviral vector, which may be a lentiviral vector. For example, retroviruses from which the retroviral vectors may be derived include, but are not limited to, alpharetroviruses, betaretroviruses, gammaretroviruses, deltaretroviruses, epsilonretroviruses, lentiviruses such as the lentiviral vectors described in U.S. Pat. Nos. 5,981,276 and 6,312,682, in addition to spumavirusus. Specific examples of retroviruses that may be used include, but are not limited to, Rous sarcoma virus, avian leukosis virus, avian myeloblastosis virus, mouse mammary tumor virus, feline sarcoma virus, avian reticuloendotheliosis virus, myeloproliferative sarcoma virus, various murine leukemia viruses, Moloney murine leukemia virus, Harvey murine sarcoma virus, bovine leukemia virus, T-lymphotropic viruses, avian leukosis virus, gibbon ape leukemia virus, feline leukemia virus, human immunodeficiency virus, simian immunodeficiency virus, feline immunodeficiency virus, and bovine immunodeficiency virus.

A viral vector also includes one or more promoters. Suitable promoters that may be employed include, but are not limited to, the retroviral LTR; the SV40 promoter; and the human cytomegalovirus (CMV) promoter described in Miller et al., *Biotechniques* 7:980-990 (1989), or any other promoter (e.g., eukaryotic cellular promoters including, for example, the histone, pol III, and β-actin promoters). Other viral promoters that may be employed include, but are not limited to, adenovirus promoters, ubiquitin promoters, thymidine kinase (TK) promoters, and B19 parvovirus promoters.

A retroviral vector may be used with its native, retroviral envelope protein, or it may be pseudotyped with a different envelope protein to target certain cell types or to increase viral titer. Certain embodiments may employ envelope proteins derived from either retroviral or non-retroviral sources. Examples of envelope proteins derived from non-retroviral sources include, but are not limited to, the Sindbis virus E2 glycoprotein and the vesticular stomatitis virus G-protein, as described in U.S. Pat. Nos. 5,512,421 and 5,817,491.

The retroviral vector may be either replication competent or replication defective. Replication defective retroviruses are capable of infecting target cells in a single round infection, but do not produce infectious virus particles after that single round, and thus will not cause a spreading infection. In certain embodiments, the retroviral vector may contain on a single plasmid comprising the gene of interest in addition to all the necessary retroviral coding sequences, such as the structural and enzymatic coding sequences. In other embodiments, the retroviral vector may contain the gene of interest attached to the minimal packaging sequences required for incorporation into a virion particle. For such minimal retroviral vectors, the vector may be introduced into a producer cell at the same time as one or more viral packaging plasmids containing the structural and enzymatic viral proteins, such as those described in U.S. Pat. No. 6,506,604, or it may be introduced into a packaging cell line (e.g., PE501, PA317, ψ-2, ψ-AM, PA12, T19-14X, VT-19-17-H2, ψCRE, ψCRIP, GP+E-86, GP+envAm12, DAN; see also, e.g., Miller, *Human Gene Therapy,* 1:5-14 (1990)); and U.S. Pat. No. 5,591,634, to form producer cell lines. The vector may introduced into the producer cells through any means known in the art, such as, for example, transfection by electroporation, the use of liposomes, and/or calcium phosphate precipitation. The producer cell line generates infectious retroviral vector particles that include the nucleic acid sequence(s) encoding the polypeptides or proteins of interest as described herein. Such retroviral vector particles then may be employed to transduce eukaryotic cells, either in vitro or in vivo. Eukaryotic cells that may be transduced include, for example, embryonic stem cells, embryonic carcinoma cells, hematopoietic stem cells, hepatocytes, fibroblasts, myoblasts, keratinocytes, endothelial cells, epithelial cells including lung epithelial cells and intestinal epithelial cells, and other culture-adapted cell lines.

Transduced cells may be further selected isolated for positive and stable expression of the polypeptides or proteins of interest, or they may be used immediately as transiently expressing cells. Stable expressing cells may be selected or isolated according to known techniques in the art, such as by flow cytometric cell sorting or by drug selection. Stable cells may be isolated for either clonal expansion or bulk expansion of positive cells.

When transient expression of the cytoplasmic indicator protein, for example, is desired or when cells that stably express the cytoplasmic indicator protein are difficult to obtain, epithelial cells comprising at least one CaCC may be transfected, transformed, or transduced with a recombinant expression vector (including a plasmid or viral vector (e.g., a retroviral vector, including a lentiviral vector) prior to performing a method to determine anion influx or to identify an agent that inhibits a CaCC. For example, epithelial cells (e.g., a plurality of intestinal epithelial cells or lung epithelial cells) may be infected (i.e., transduced) with a retroviral vector such as a lentiviral vector that comprises a polynucleotide encoding a cytoplasmic indicator protein that is capable of binding the halide or nitrate, under conditions and for a time sufficient for the vector to infect the plurality of epithelial cells. The epithelial cells are then cultured under conditions and for a time sufficient that permit expression of the indicator protein in the cytoplasm of the epithelial cell. The epithelial cells expressing the cytoplasmic indicator protein may then be used in the methods as described herein for identifying a CaCC inhibitor or for determining anion influx through a CaCC.

Agents

Agents (which may also be referred to as bioactive agents) may be provided as "libraries" or collections of compounds, compositions, or molecules. For example, agents include low molecular weight, organic molecules, which typically include compounds known in the art as "small molecules." A small molecule may have a molecular weight less than $10^5$ daltons, less than $10^4$ daltons, or less than $10^3$ daltons. Other agents that may be useful for inhibiting or blocking at least one CaCC, thus inhibiting, blocking, or reducing chloride conductance through the CaCC and inhibiting chloride secretion from a cell through a CaCC include peptides. Peptides and small molecules may be synthesized according to methods routinely practiced by person skilled in the synthesis of peptides or small molecules, respectively.

The methods described herein are useful for screening large numbers of agents (e.g., multiple hundreds of agents) quickly. Candidate agents, such as small molecules and peptides, may be obtained from combinatorial libraries. Combinatorial libraries of agents can be purchased from a commercial vendor or can be prepared according to methods with which a skilled artisan is familiar. Examples of methods for the synthesis of molecular libraries can be found in the art, for example in DeWitt et al., *Proc. Natl. Acad. Sci. U.S.A.* 90:6909 (1993); Erb et al., *Proc. Natl. Acad. Sci. USA* 91:11422 (1994); Zuckermann et al., *J. Med. Chem.* 37:2678 (1994); Cho et al., *Science* 261:1303 (1993); Carrell et al., *Angew. Chem. Int. Ed. Engl.* 33:2059 (1994); Carell et al., *Angew. Chem. Int. Ed. Engl.* 33:2061 (1994); and in Gallop et al., *J. Med. Chem.* 37:1233 (1994).

Candidate agents that are provided as members of a combinatorial library, include synthetic agents prepared according to a plurality of predetermined chemical reactions performed in a plurality of reaction vessels. For example, various starting compounds may be prepared according to one or more of solid-phase synthesis, recorded random mix methodologies, and recorded reaction split techniques that permit a given constituent to traceably undergo a plurality of permutations and/or combinations of reaction conditions. The resulting products comprise a library that can be screened followed by iterative selection and synthesis procedures. Such synthetic combinatorial libraries include a library of peptides (see, e.g., International Patent Application Nos. PCT/US91/08694 and PCT/US91/04666) or other compositions that may include small molecules as provided herein (see, e.g., International Patent Application No. PCT/US94/08542, EP Patent No. 0774464, U.S. Pat. Nos. 5,798, 035, 5,789,172, 5,751,629, which are hereby incorporated by reference in their entireties).

Methods for characterizing an agent, including the compounds described herein, such as determining an effective concentration (i.e., a concentration of agent that inhibits activation of a CaCC; inhibits conductance of chloride through a CaCC and/or that inhibits fluid secretion from a cell (i.e., that inhibits efflux of chloride and water); and/or that is a therapeutically effective amount for treating a condition, disease or disorder described herein) may be performed using techniques and procedures described herein and routinely practiced by a person skilled in the art. The capability of an agent to inhibit a CaCC (i.e., inhibit activation of a CaCC or inhibit halide (e.g., chloride or iodide) conductance or current) using the methods described herein include the use of cells, such as epithelial cells, that comprise a cytoplasmic indicator protein. Other methods and techniques practiced in the art may be used that determine whether the agent inhibits CaCC(s). Certain epithelial cells or cell lines that comprise at least one CaCC (e.g., intestinal epithelial cells, T84 and Caco-2), may not exhibit optimum properties and characteristics for use in the methods described herein for identifying an agent or determining anion influx. For example, such cells may not be readily transformed, transfected, or transduced with a recombinant expression vector that expresses the cytoplasmic indicator protein, or if the vector can be introduced, the signal (in the instance in which YFP is the indicator protein, the fluorescent signal) may be too weak. Such cells may not exhibit the requisite growth characteristics (i.e., propagate too slowly or fail to reach an adequate level of confluency), and/or may not sufficiently adhere to a solid surface, particularly a plastic surface sufficiently to withstand multiple washes. These cells expressing at least one CaCC may still be used in other methods practiced in the art and described herein to determine the level of chloride conductance or secretion in the cell (see, e.g., Examples 3 and 4 herein; Hartzell et al., supra; Kidd et al., supra). In addition to use of calcium-elevating agonists described herein that bind to a cognate receptor or ligand on an epithelial cell (e.g., histamine, calcimycin, ATP, carbachol, and forskolin), a calcium-elevating agent such as thapsigargin, which produces calcium elevation without ligand-receptor binding or phosphoinositide signaling may also be used in assays and techniques for characterizing an agent.

Other exemplary methods include short circuit apical chloride ion current measurements and patch-clamp analysis (see, e.g., Muanprasat et al., *J. Gen. Physiol.* 124:125-37 (2004); Ma et al., *J. Clin. Invest.* 110:1651-58 (2002); see also, e.g., Carmeliet, *Verh. K. Acad. Geneeskd. Belg.* 55:5-26 (1993); Hamill et al., *Pflugers Arch.* 391:85-100 (1981)). In patch clamp analysis, for example, ionomycin may be used to elevate the intracellular calcium level. The agents may also be analyzed in animal models, for example, a closed intestinal loop model of cholera, suckling mouse model of cholera, and in vivo imaging of gastrointestinal transit (see, e.g., Takeda et al., *Infect. Immun.* 19:752-54 (1978)).

Aminothiophene Compounds and Aminothiazole Compounds and Related Compositions

Agents identified by the methods described herein include agents that are capable of inhibiting chloride conductance through a CaCC, and thus inhibiting chloride efflux, and consequently water secretion from the cell. Provided herein are compounds that are potent CaCC inhibitors, which were identified using the methods described herein. The exemplary compounds belong to two chemical classes, aminothiophenes (referred to herein also as Class A compounds) and aminothiazoles (referred to herein also as Class B compounds). These compounds, in addition to exhibiting capability to inhibit CaCCs, exhibit high potency, favorable water solubility, drug-like properties, and chemical stability.

Aminothiophene Compounds

In one embodiment, compounds, and compositions comprising these compounds, of the aminothiophene class are provided. In one embodiment, the composition comprises a physiologically acceptable excipient and a compound having the following structure (I):

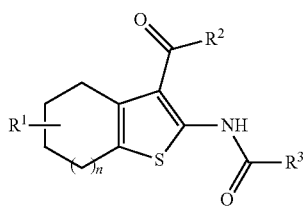

(I)

or a pharmaceutically acceptable salt, prodrug or stereoisomer thereof, wherein $R^1$ is hydrogen or optionally substituted alkyl; $R^2$ is hydroxy, optionally substituted alkoxy, or optionally substituted phenylamino; $R^3$ is optionally substituted alkyl, optionally substituted alkenyl, optionally substituted cycloalkyl, optionally substituted phenyl, or optionally substituted heterocyclyl; and n is 0, 1, or 2, and wherein the compound of structure I comprises at least one —COOH.

In another embodiment, the composition comprises a physiologically acceptable excipient wherein n is 1 or 2 and the compound has the following structure (IA):

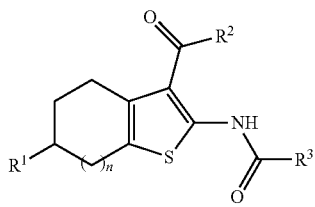

(IA)

or a pharmaceutically acceptable salt, prodrug or stereoisomer thereof, wherein $R^1$ is hydrogen or optionally substituted alkyl;

$R^2$ is hydroxy, optionally substituted alkoxy, or optionally substituted phenylamino;

$R^3$ is optionally substituted alkyl, optionally substituted alkenyl, optionally substituted cycloalkyl, optionally substituted phenyl, or optionally substituted heterocyclyl, and wherein the compound of structure (IA) comprises at least one —COOH.

The compound of structure I and I(A) that has at least one —COOH (i.e., carboxy), in one embodiment, includes, but is not limited to, a compound wherein $R^2$ is hydroxy. In another embodiment, the compound may include $R^3$ that is —(CH$_2$)$_2$C(=O)OH, —CH=CHC(=O)OH, cyclohexyl substituted with —COOH, or phenyl substituted with —COOH.

In a specific embodiment of structure I and I(A), $R^1$ is hydrogen, tert-butyl, or tert-pentyl. In yet another specific embodiment, $R^1$ is tert-butyl or tert-pentyl. In certain embodiments, $R^2$ is —OR$^4$ wherein $R^4$ is hydrogen or optionally substituted $C_{1-6}$ alkyl; or phenylamino optionally substituted with $C_{1-6}$ alkoxy or $C_{1-6}$ alkyl. In certain embodiments, $R^2$ is —OR$^4$ wherein $R^4$ is hydrogen or optionally substituted with methyl or ethyl. In other certain embodiments, $R^2$ is phenylamino optionally substituted with methoxy or methyl. In other specific embodiments, $R^3$ is optionally substituted furanyl; optionally substituted $C_1$-$C_6$ alkyl; optionally substituted $C_1$-$C_6$ alkenyl; optionally substituted cyclohexyl; phenyl; or phenyl substituted with halo, $C_{1-6}$ alkyl, $C_{1-6}$ alkoxy, or —COOH. In yet another specific embodiment, $R^3$ is —(CH$_2$)$_2$C(=O)OH or —CH=CHC(=O)OH. In another specific embodiment, $R^3$ is phenyl substituted with chloro, methyl, or methoxy. In still another specific embodiment, $R^3$ is cyclohexyl substituted with —COOH.

In a specific embodiment, the composition comprises the compound of structure (I) or (IA) wherein n is 1 and $R^1$ is hydrogen, tert-butyl, or tert-pentyl, and the compound has one of the following structures (Ia), (Ib), or (Ic):

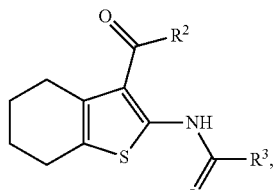

(Ia)

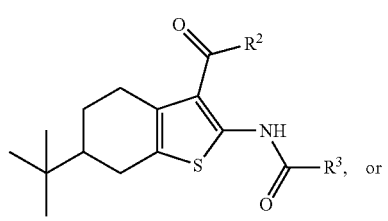

(Ib)

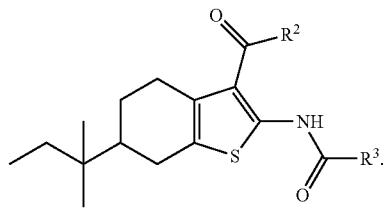

(Ic)

In a specific embodiment of structures (Ia), (Ib), or (Ic), $R^2$ is —OR$^4$ wherein $R^4$ is hydrogen or optionally substituted $C_{1-4}$ alkyl; or phenylamino optionally substituted with $C_{1-4}$ alkoxy or $C_{1-4}$ alkyl. In another specific embodiment, $R^2$ is —OR$^4$ wherein $R^4$ is hydrogen or optionally substituted with methyl or ethyl; or phenylamino optionally substituted with methoxy or methyl. In another certain embodiments, $R^3$ is optionally substituted furanyl; optionally substituted $C_1$-$C_6$ alkyl; optionally substituted $C_1$-$C_6$ alkenyl; optionally substituted cyclohexyl; phenyl; or phenyl substituted with halo, $C_{1-6}$ alkyl, $C_{1-6}$ alkoxy, or —COOH. In still another embodiment, $R^3$ is —(CH$_2$)$_2$C(=O)OH or —CH=CHC(=O)OH. In another specific embodiment, $R^3$ is phenyl substituted with chloro, methyl, or methoxy. In yet another specific embodiment, $R^3$ is cyclohexyl substituted with —COOH.

In another specific embodiment, the composition described above comprises the compound of structure (I) or (IA) wherein n is 1 and $R^2$ is —OR$^4$ wherein $R^4$ is hydrogen or optionally substituted $C_{1-6}$ alkyl, and the compound has the following structure (Id):

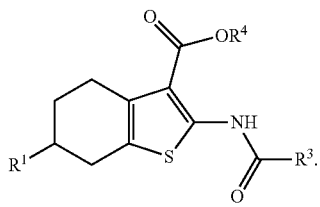
(Id)

In certain specific embodiments, $R^4$ is hydrogen, methyl, or ethyl. In other specific embodiments, $R^1$ is hydrogen, tert-butyl, or tert-pentyl. In other certain embodiments, $R^1$ is tert-butyl, or tert-pentyl. In yet another specific embodiment, $R^3$ is optionally substituted furanyl; optionally substituted $C_1$-$C_6$ alkyl; optionally substituted $C_1$-$C_6$ alkenyl; optionally substituted cyclohexyl; phenyl; or phenyl substituted with halo, $C_{1-6}$ alkyl, $C_{1-6}$ alkoxy, or —COOH. In still another embodiment, $R^3$ is —$(CH_2)_2C(=O)OH$ or —CH=CHC(=O)OH. In another specific embodiment, $R^3$ is phenyl substituted with chloro, methyl, or methoxy. In yet another specific embodiment, $R^3$ is cyclohexyl substituted with —COOH.

In another specific embodiment of the compositions described herein, wherein n is 1, the compound of structure (I) and (IA) has any one of the following structures (Ie), (If), (Ig), or (Ih):

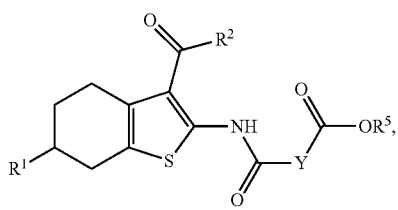
(Ie)

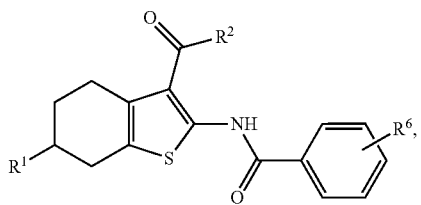
(If)

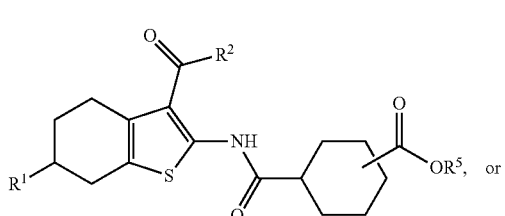
(Ig)

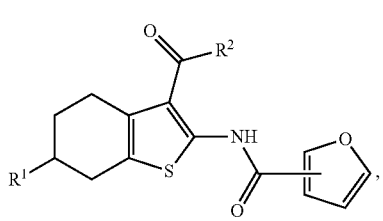
(Ih)

wherein Y is optionally substituted lower alkyl; $R^5$ is hydrogen, optionally substituted $C_{1-6}$ alkylene, or optionally substituted $C_{1-6}$ alkenylene; and $R^6$ is hydrogen, optionally substituted alkyl, optionally substituted alkoxy, —COOH, or halo. In a certain embodiment, $R^6$ is hydrogen, halo, $C_{1-6}$ alkyl, $C_{1-6}$ alkoxy, or —COOH. In another certain embodiment, $R^6$ is hydrogen, chloro, methyl, or methoxy. In still another embodiment, $R^1$ is hydrogen, tert-butyl, or tert-pentyl and $R^2$ is —$OR^4$ wherein $R^4$ is hydrogen or optionally substituted $C_{1-6}$ alkyl. In another specific embodiment, $R^4$ is hydrogen, methyl, or ethyl. In another specific embodiment, $R^2$ is phenylamino optionally substituted with methoxy or methyl.

In yet another specific embodiment, the composition comprises the compound of structure (I) or (IA) wherein n is 2, $R^1$ is hydrogen, $R^2$ is —$OR^4$, and $R^3$ is optionally substituted phenyl, and the compound has the following structure (Ii):

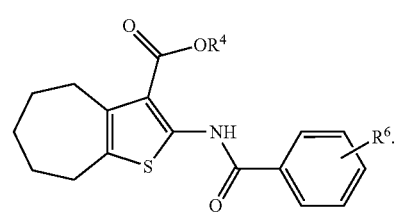
(Ii)

wherein $R^4$ is hydrogen or optionally substituted $C_{1-4}$ alkyl and $R^6$ is hydrogen, optionally substituted alkyl, optionally substituted alkoxy, or halo.

In a specific embodiment, $R^4$ is hydrogen, methyl, or ethyl. In another specific embodiment, $R^6$ is hydrogen, chloro, optionally substituted $C_{1-6}$ alkyl, or optionally substituted $C_{1-6}$ alkoxy. In yet another specific embodiment, $R^6$ is hydrogen, chloro, methyl, or methoxy.

In particular specific embodiments, the compositions comprise the specific aminothiophene compounds having a structure (I), including 6-tert-butyl-2-(furan-2-carboxamido)-4,5,6,7-tetrahydrobenzo[b]thiophene-3-carboxylic acid; 6-tert-butyl-2-(2-methylbenzamido)-4,5,6,7-tetrahydrobenzo[b]thiophene-3-carboxylic acid; 6-tert-butyl-2-(3-chlorobenzamido)-4,5,6,7-tetrahydrobenzo[b]thiophene-3-carboxylic acid; 2-benzamido-6-tert-butyl-4,5,6,7-tetrahydrobenzo[b]thiophene-3-carboxylic acid; 6-tert-butyl-2-(2-chlorobenzamido)-4,5,6,7-tetrahydrobenzo[b]thiophene-3-carboxylic acid; 4-(6-tert-butyl-3-(ethoxycarbonyl)-4,5,6,7-tetrahydrobenzo[b]thiophen-2-ylamino)-4-oxobutanoic acid; (E)-4-(6-tert-butyl-3-(ethoxycarbonyl)-4,5,6,7-tetrahydrobenzo[b]thiophen-2-ylamino)-4-oxobut-2-enoic acid; 2-(6-tert-butyl-3-(ethoxycarbonyl)-4,5,6,7-tetrahydrobenzo[b]thiophen-2-ylcarbamoyl)cyclohexanecarboxylic acid; 5-(6-tert-butyl-3-(methoxycarbonyl)-4,5,6,7-tetrahydrobenzo[b]thiophen-2-ylamino)-5-oxopentanoic acid; 2-(3-(ethoxycarbonyl)-6-tert-pentyl-4,5,6,7-tetrahydrobenzo[b]thiophen-2-ylcarbamoyl)cyclohexanecarboxylic acid; 4-(6-tert-butyl-3-(methoxycarbonyl)-4,5,6,7-tetrahydrobenzo[b]thiophen-2-ylamino)-4-oxobutanoic acid; 2-(4-methylbenzamido)-5,6,7,8-tetrahydro-4H-cyclohepta[b]thiophene-3-carboxylic acid; 2-benzamido-5,6,7,8-tetrahydro-4H-cyclohepta[b]thiophene-3-carboxylic acid; 2-(2-chlorobenzamido)-5,6,7,8-tetrahydro-4H-cyclohepta[b]thiophene-3-carboxylic acid; 2-(3-methoxybenzamido)-5,6,7,8-tetrahydro-4H-cyclohepta[b]thiophene-3-carboxylic acid; 4-(6-tert-butyl-3-(m-tolylcarbamoyl)-4,5,6,7-tetrahydrobenzo[b]thiophen-2-ylamino)-4-oxobutanoic acid; 2-(3-methylbenzamido)-4,5, 6,7-tetrahydrobenzo[b]thiophene-3-carboxylic acid; or 4-(6-tert-butyl-3-(4-methoxyphenylcarbamoyl)-4,5,6,7-tetrahydrobenzo[b]thiophen-2-ylamino)-4-oxobutanoic acid. In a specific embodiment, the compound is 6-tert-butyl-2-(furan-2-carboxamido)-4,5,6,7-tetrahydrobenzo[b]thiophene-3-carboxylic acid. The chemical structures of these compounds (also referred to herein as Class A compounds) are presented in Table 1.

TABLE 1

Aminothiophene Compounds

| Compound | Structure | Chemical Name |
|---|---|---|
| CaCC$_{inh}$-A01 | 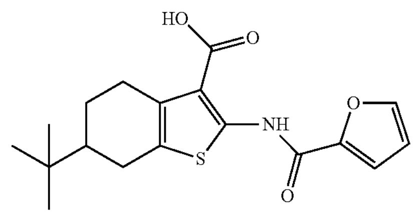 [SMILES: CC(C)(C)C1CCc2c(sc(NC(=O)c3ccco3)c2C(=O)O)C1] | 6-tert-butyl-2-(furan-2-carboxamido)-4,5,6,7-tetrahydrobenzo[b]thiophene-3-carboxylic acid |
| CaCC$_{inh}$-A02 | 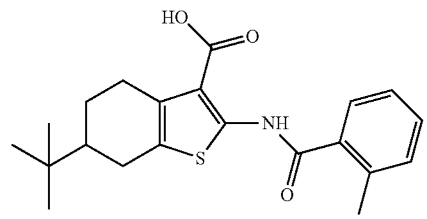 [SMILES: Cc1ccccc1C(=O)Nc1sc2c(c1C(=O)O)CCC(C(C)(C)C)C2] | 6-tert-butyl-2-(2-methylbenzamido)-4,5,6,7-tetrahydrobenzo[b]thiophene-3-carboxylic acid |
| CaCC$_{inh}$-A03 | 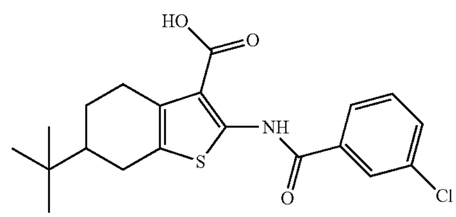 [SMILES: CC(C)(C)C1CCc2c(sc(NC(=O)c3cccc(Cl)c3)c2C(=O)O)C1] | 6-tert-butyl-2-(3-chlorobenzamido)-4,5,6,7-tetrahydrobenzo[b]thiophene-3-carboxylic acid |
| CaCC$_{inh}$-A04 | 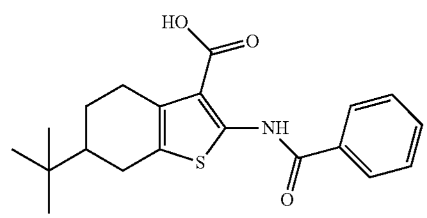 [SMILES: CC(C)(C)C1CCc2c(sc(NC(=O)c3ccccc3)c2C(=O)O)C1] | 2-benzamido-6-tert-butyl-4,5,6,7-tetrahydrobenzo[b]thiophene-3-carboxylic acid |
| CaCC$_{inh}$-A05 | 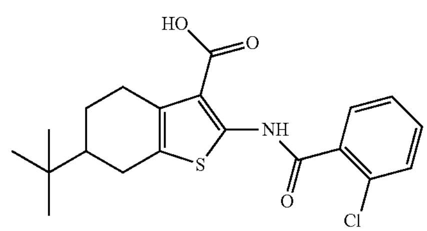 [SMILES: CC(C)(C)C1CCc2c(sc(NC(=O)c3ccccc3Cl)c2C(=O)O)C1] | 6-tert-butyl-2-(2-chlorobenzamido)-4,5,6,7-tetrahydrobenzo[b]thiophene-3-carboxylic acid |
| CaCC$_{inh}$-A06 | 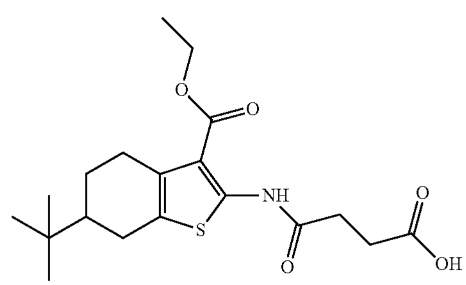 [SMILES: CCOC(=O)c1c(NC(=O)CCC(=O)O)sc2c1CCC(C(C)(C)C)C2] | 4-(6-tert-butyl-3-(ethoxycarbonyl)-4,5,6,7-tetrahydrobenzo[b]thiophen-2-ylamino)-4-oxobutanoic acid |

TABLE 1-continued

Aminothiophene Compounds

| Compound | Structure | Chemical Name |
|---|---|---|
| CaCC$_{inh}$-A07 | 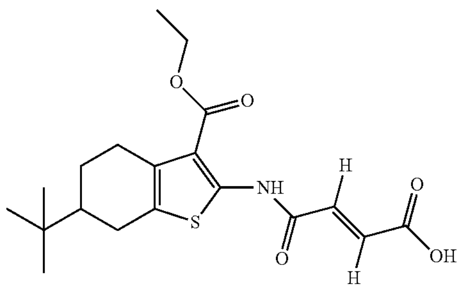 [SMILES: CCOC(=O)c1c(NC(=O)/C=C/C(=O)O)sc2c1CCC(C(C)(C)C)C2] | (E)-4-(6-tert-butyl-3-(ethoxycarbonyl)-4,5,6,7-tetrahydrobenzo[b]thiophen-2-ylamino)-4-oxobut-2-enoic acid |
| CaCC$_{inh}$-A08 | 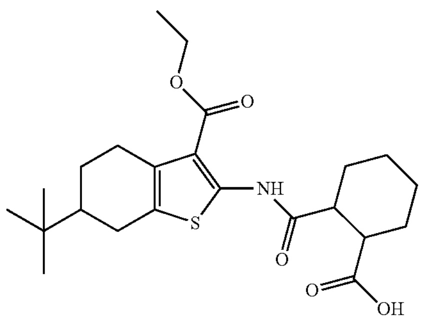 [SMILES: CCOC(=O)c1c(NC(=O)C2CCCCC2C(=O)O)sc2c1CCC(C(C)(C)C)C2] | 2-(6-tert-butyl-3-(ethoxycarbonyl)-4,5,6,7-tetrahydrobenzo[b]thiophen-2-ylcarbamoyl)cyclohexane-carboxylic acid |
| CaCC$_{inh}$-A09 | 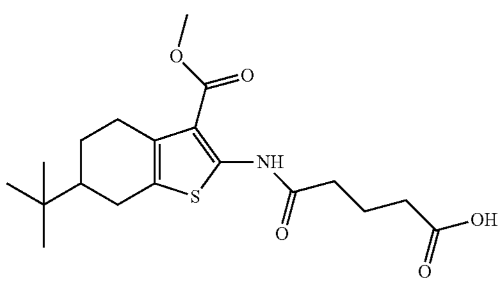 [SMILES: COC(=O)c1c(NC(=O)CCCC(=O)O)sc2c1CCC(C(C)(C)C)C2] | 5-(6-tert-butyl-3-(methoxycarbonyl)-4,5,6,7-tetrahydrobenzo[b]thiophen-2-ylamino)-5-oxopentanoic acid |
| CaCC$_{inh}$-A10 | 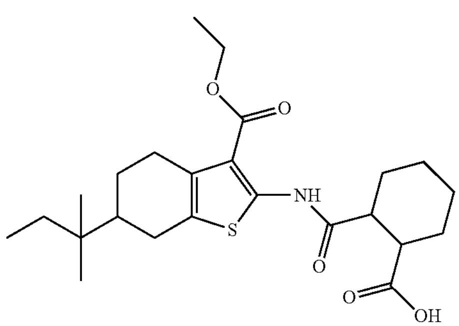 [SMILES: CCOC(=O)c1c(NC(=O)C2CCCCC2C(=O)O)sc2c1CCC(C(C)(C)CC)C2] | 2-(3-(ethoxycarbonyl)-6-tert-pentyl-4,5,6,7-tetrahydrobenzo[b]thiophen-2-ylcarbamoyl)cyclohexane-carboxylic acid |
| CaCC$_{inh}$-A11 | 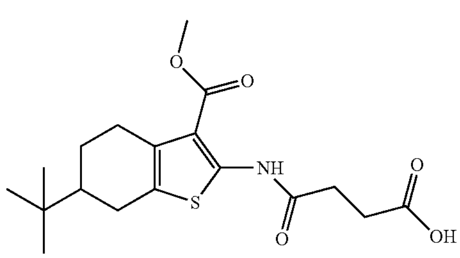 [SMILES: COC(=O)c1c(NC(=O)CCC(=O)O)sc2c1CCC(C(C)(C)C)C2] | 4-(6-tert-butyl-3-(methoxycarbonyl)-4,5,6,7-tetrahydrobenzo[b]thiophen-2-ylamino)-4-oxobutanoic acid |

TABLE 1-continued

| Aminothiophene Compounds | | |
|---|---|---|
| Compound | Structure | Chemical Name |
| CaCC$_{inh}$-A12 | | 2-(4-methylbenzamido)-5,6,7,8-tetrahydro-4H-cyclohepta[b]thiophene-3-carboxylic acid |
| CaCC$_{inh}$-A13 | | 2-benzamido-5,6,7,8-tetrahydro-4H-cyclohepta[b]thiophene-3-carboxylic acid |
| CaCC$_{inh}$-A14 | | 2-(2-chlorobenzamido)-5,6,7,8-tetrahydro-4H-cyclohepta[b]thiophene-3-carboxylic acid |
| CaCC$_{inh}$-A15 | | 2-(3-methoxybenzamido)-5,6,7,8-tetrahydro-4H-cyclohepta[b]thiophene-3-carboxylic acid |
| CaCC$_{inh}$-A16 | | 4-(6-tert-butyl-3-(m-tolylcarbamoyl)-4,5,6,7-tetrahydrobenzo[b]thiophen-2-ylamino)-4-oxobutanoic acid |
| CaCC$_{inh}$-A17 | | 2-(3-methylbenzamido)-4,5,6,7-tetrahydrobenzo[b]thiophene-3-carboxylic acid |

TABLE 1-continued

Aminothiophene Compounds

| Compound | Structure | Chemical Name |
|---|---|---|
| CaCC$_{inh}$-A18 | 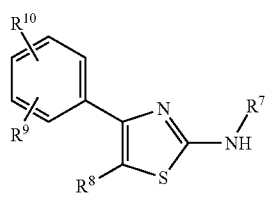 | 4-(6-tert-butyl-3-(4-methoxyphenylcarbamoyl)-4,5,6,7-tetrahydrobenzo[b]thiophen-2-ylamino)-4-oxobutanoic acid |

Aminothiazole Compounds

In one embodiment, compounds, and compositions comprising these compounds, of the aminothiazole class are provided. In one embodiment, the composition comprises a physiologically acceptable excipient and a compound having the following structure (II):

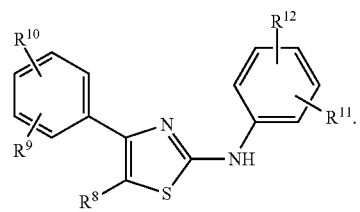

(II)

or a pharmaceutically acceptable salt, prodrug or stereoisomer thereof, wherein $R^7$ is optionally substituted $C_{1-6}$ alkyl, optionally substituted phenyl, or optionally substituted phenylacyl;

$R^8$ is hydrogen or optionally substituted $C_{1-6}$ alkyl or optionally substituted phenyl;

$R^9$ and $R^{10}$ are the same or different and independently hydrogen, optionally substituted alkyl, optionally substituted alkoxy, or optionally substituted phenoxy. In certain embodiments, at least one of $R^9$ and $R^{10}$ is not hydrogen.

In a particular embodiment, $R^7$ is methyl, ethyl, unsubstituted phenylacyl, phenyl, or phenyl substituted with carboxy, $C_{1-6}$ alkyl, halo, optionally substituted cycloalkyl, or $C_{1-6}$ alkoxy. In other specific embodiments, $R^7$ is phenyl substituted with $C_{1-4}$ alkyl, or $C_{1-4}$ alkoxy. In yet another specific embodiment, $R^7$ is phenyl substituted with hydroxy, chloro, bromo, methyl, ethyl, trifluoromethyl, methoxy, ethoxy, or cyclohexyl. In still another specific embodiment, $R^7$ is phenyl substituted with carboxy and hydroxyl; di-halo; or $C_{1-6}$ alkyl and halo. In yet another specific embodiment, $R^7$ is phenyl substituted with di-chloro or with methyl and chloro.

In another specific embodiment, $R^8$ is hydrogen or optionally substituted $C_{1-4}$ alkyl. In a specific embodiment, $R^8$ is hydrogen, n-propyl, —CH$_2$C(═O)OH, or —(CH$_2$)$_2$C(═O)OH.

In a particular embodiment, $R^9$ is hydrogen, optionally substituted $C_{1-4}$ alkyl, or $C_{1-4}$ alkoxy, or phenoxy; and $R^{10}$ is optionally substituted $C_{1-4}$ alkyl, optionally substituted $C_{1-4}$ alkoxy, or phenoxy. In another particular embodiment, $R^9$ is hydrogen, $C_{1-4}$ alkyl, trifluoromethyl, methoxy, ethoxy, or phenoxy; and $R^{10}$ is $C_{1-4}$ alkyl, trifluoromethyl, methoxy, ethoxy, or phenoxy. In a specific embodiment, $R^9$ is hydrogen and $R^{10}$ is methyl, ethyl, isobutyl, methoxy, phenoxy, or trifluoromethyl. In another specific embodiment, $R^9$ is hydrogen and $R^{10}$ is methyl, ethyl, isobutyl, phenoxy, or methoxy, and $R^{10}$ is located at the 4-position. In yet another specific embodiment, $R^9$ is hydrogen and $R^{10}$ is trifluoromethyl and $R^{10}$ is located at the 3-position. In still another specific embodiment, $R^9$ is methyl and located at the 2-position, and $R^{10}$ is methyl and located at the 4-position. In certain embodiments, the compound of substructure IIa comprises at least one —COOH.

In another embodiment, the composition comprises the compound of structure (II) wherein $R^7$ is optionally substituted phenyl and the compound has the following substructure (IIa):

(IIa)

wherein $R^{11}$ and $R^{12}$ are the same or different and independently hydrogen, hydroxy, carboxy, halo, optionally substituted alkyl, optionally substituted alkoxy, or optionally substituted cycloalkyl.

In one specific embodiment of the substructure (IIa), $R^9$ and $R^{10}$ are the same or different and independently hydrogen, optionally substituted $C_{1-4}$ alkyl, or optionally substituted $C_{1-4}$ alkoxy, or phenoxy. In another specific embodiment, $R^9$ and $R^{10}$ are the same or different and independently hydrogen, $C_{1-4}$ alkyl, trifluoromethyl, methoxy, ethoxy, or phenoxy. In still another specific embodiment $R^9$ is hydrogen and $R^{10}$ is methyl, ethyl, isobutyl, methoxy, phenoxy, or trifluoromethyl. In yet another specific embodiment, $R^9$ is hydrogen and $R^{10}$ is methyl, ethyl, isobutyl, phenoxy, or methoxy, and wherein $R^{10}$ is located at the 4-position. In still another specific embodiment, $R^9$ is hydrogen and $R^{10}$ is trifluoromethyl and $R^{10}$ is located at the 3-position. In another specific embodiment, $R^9$ is methyl and located at the 2-position, and wherein $R^{10}$ is methyl and located at the 4-position. In other specific embodiments of the substructure (IIa), $R^8$ is hydrogen or optionally substituted $C_{1-6}$ alkyl. In another specific embodiment, $R^8$ is hydrogen, n-propyl, —CH$_2$C(=O)OH, or —(CH$_2$)$_2$C(=O)OH. In specific embodiments of the substructure (IIa), $R^{11}$ and $R^{12}$ are the same or different and independently hydrogen, hydroxy, carboxy, halo, optionally substituted $C_{1-4}$ alkyl, $C_{1-4}$ alkoxy, or optionally substituted cyclohexyl. In still other embodiments, $R^{11}$ is hydrogen and $R^{12}$ is hydrogen, hydroxy, carboxy, bromo, chloro, trifluoromethyl, methyl, ethyl, isobutyl, methoxy, ethoxy, or cyclohexyl. In certain specific embodiment, $R^{11}$ is hydroxy and $R^{12}$ is carboxy. In other certain specific embodiments, $R^{11}$ is methyl and $R^{12}$ is halo. In still another specific embodiment, $R^{11}$ is hydrogen and $R^{12}$ is chloro or wherein each of $R^{11}$ and $R^{12}$ is chloro. In certain embodiments, the compound of substructure IIa comprises at least one —COOH.

In another embodiment, the composition comprises the compound of structure (II) $R^8$ is hydrogen or Y and the compound has the following structures (IIb) or (IIc):

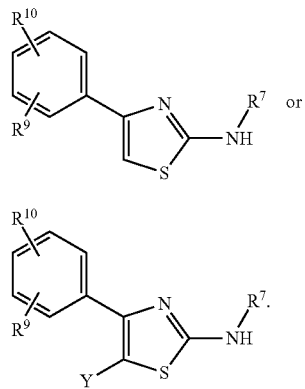

wherein Y is optionally substituted $C_{1-4}$ alkyl.

In specific embodiments of the substructures (IIb) and (IIc), Y is methyl, ethyl, n-propyl, —CH$_2$C(=O)OH, or —(CH$_2$)$_2$C(=O)OH.

In another specific embodiment of the substructures (IIb) and (IIc), $R^7$ is methyl, ethyl, unsubstituted phenylacyl, phenyl, or phenyl substituted with carboxy, $C_{1-6}$ alkyl, halo, optionally substituted cycloalkyl, or $C_{1-6}$ alkoxy. In yet another specific embodiment, $R^7$ is phenyl substituted with hydroxy, chloro, bromo, methyl, ethyl, trifluoromethyl, methoxy, ethoxy, or cyclohexyl. In still another specific embodiment, $R^7$ is phenyl substituted with carboxy and hydroxyl; di-halo; or $C_{1-6}$ alkyl and halo. In yet another specific embodiment, $R^7$ is phenyl substituted with di-chloro or with methyl and chloro.

In other specific embodiments of the substructures (IIb) and (IIc), $R^9$ and $R^{10}$ are the same or different and independently hydrogen, optionally substituted $C_{1-4}$ alkyl, or optionally substituted $C_{1-4}$ alkoxy, or phenoxy. In another specific embodiment, $R^9$ and $R^{10}$ are the same or different and independently hydrogen, $C_{1-4}$ alkyl, trifluoromethyl, methoxy, ethoxy, or phenoxy. In still another specific embodiment $R^9$ is hydrogen and $R^{10}$ is methyl, ethyl, isobutyl, methoxy, phenoxy, or trifluoromethyl. In yet another specific embodiment, $R^9$ is hydrogen and $R^{10}$ is methyl, ethyl, isobutyl, phenoxy, or methoxy, and wherein $R^{10}$ is located at the 4-position. In still another specific embodiment, $R^9$ is hydrogen and $R^{10}$ is trifluoromethyl and $R^{10}$ is located at the 3-position. In another specific embodiment, $R^9$ is methyl and located at the 2-position, and wherein $R^{10}$ is methyl and located at the 4-position.

In another embodiment, the composition comprises the compound of structure (II) wherein $R^9$ is hydrogen and $R^{10}$ is methyl, trifluoromethyl, or —OR$^{14}$; or each of $R^9$ and $R^{10}$ is methyl, and the compound has the following substructure (IIe), (IIf), (IIg), or (IIh):

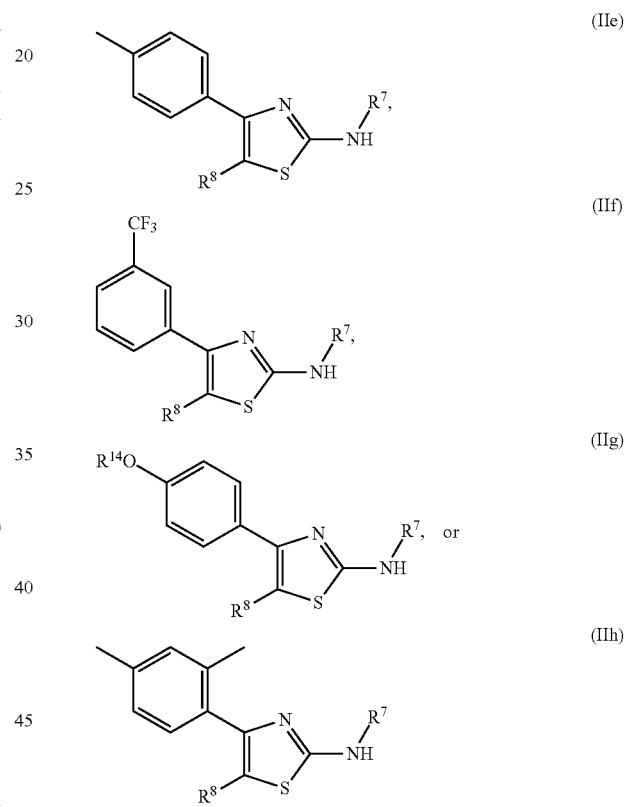

wherein $R^{14}$ is hydrogen, optionally substituted $C_{1-6}$ alkyl, or optionally substituted phenyl.

In specific embodiments of the substructures (IId), (IIe), (IIf), and (IIh), $R^{14}$ is hydrogen, methyl, or unsubstituted phenyl. In other specific embodiments, $R^7$ is methyl, ethyl, unsubstituted phenylacyl, phenyl, or phenyl substituted with carboxy, $C_{1-6}$ alkyl, halo, optionally substituted cycloalkyl, or $C_{1-6}$ alkoxy. In yet another specific embodiment, $R^7$ is substituted phenyl, wherein phenyl is substituted with hydroxy, chloro, bromo, methyl, ethyl, trifluoromethyl, methoxy, ethoxy, or cyclohexyl. In still another specific embodiment, $R^7$ is phenyl substituted with carboxy and hydroxyl; di-halo; or $C_{1-4}$ alkyl and halo. In yet another specific embodiment, $R^7$ is phenyl substituted either with di-chloro or with methyl and chloro. In yet other specific embodiments of the substructures (IId), (IIe), (IIi), and (IIh), $R^8$ is hydrogen or optionally substituted $C_{1-6}$ alkyl. In another specific embodiment, $R^8$ is hydrogen, n-propyl, —$CH_2C(=O)OH$, or —$(CH_2)_2C(=O)OH$.

In particular specific embodiments, the compositions comprise the specific Aminothiazole compounds having a structure (II), including 2-hydroxy-5-(4-p-tolylthiazol-2-ylamino)benzoic acid; 2-(2-(3-chloro-4-methylphenylamino)-4-p-tolylthiazol-5-yl)acetic acid; 2-(2-(3-bromophenylamino)-4-p-tolylthiazol-5-yl)acetic acid; 2-(2-(2,4-dichlorophenylamino)-4-p-tolylthiazol-5-yl)acetic acid; 2-(4-p-tolyl-2-(3-(trifluoromethyl)phenylamino)thiazol-5-yl)acetic acid; 4-(4-(2,4-dimethylphenyl)-5-propylthiazol-2-ylamino)benzoic acid; 2-(2-(4-bromophenylamino)-4-(2,4-dimethylphenyl)thiazol-5-yl)acetic acid; 2-(4-(2,4-dimethylphenyl)-2-(4-(trifluoromethyl)phenylamino)thiazol-5-yl)acetic acid; N-(4-isobutylphenyl)-4-(4-phenoxyphenyl)thiazol-2-amine; N-(4-cyclohexylphenyl)-4-(3-(trifluoromethyl)phenyl)thiazol-2-amine; 2-(2-(4-ethoxyphenylamino)-4-p-tolylthiazol-5-yl)acetic acid; 3-methyl-N-(5-phenyl-4-p-tolylthiazol-2-yl)benzamide; N-ethyl-4-p-tolylthiazol-2-amine; or 3-(4-(4-methoxyphenyl)-2-(4-methoxyphenylamino)thiazol-5-yl)propanoic acid. In a specific embodiment, the compound is 2-hydroxy-5-(4-p-tolylthiazol-2-ylamino)benzoic acid. The chemical structures corresponding to these aminothiazole compounds of structure (II) (also referred to herein as Class B compounds) are presented in Table 2.

TABLE 2

Aminothiazole Compounds

| Compound | Structure | Chemical Name |
|---|---|---|
| $CaCC_{inh}$-B01 | 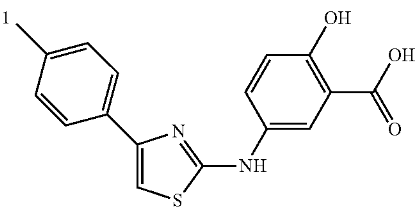 | 2-hydroxy-5-(4-p-tolylthiazol-2-ylamino)benzoic acid |
| $CaCC_{inh}$-B02 | 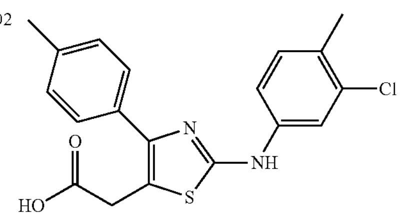 | 2-(2-(3-chloro-4-methylphenylamino)-4-p-tolylthiazol-5-yl)acetic acid |
| $CaCC_{inh}$-B03 | 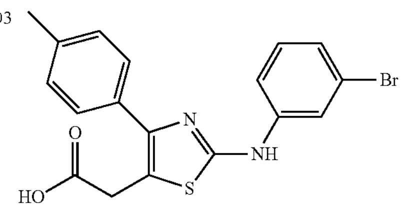 | 2-(2-(3-bromophenylamino)-4-p-tolylthiazol-5-yl)acetic acid |
| $CaCC_{inh}$-B04 | 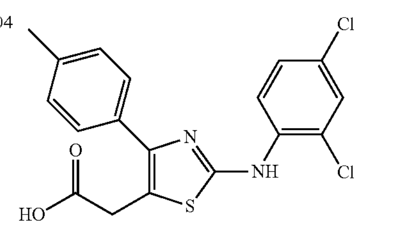 | 2-(2-(2,4-dichlorophenylamino)-4-p-tolylthiazol-5-yl)acetic acid |
| $CaCC_{inh}$-B05 | 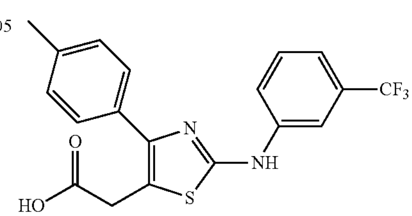 | 2-(4-p-tolyl-2-(3-(trifluoromethyl)phenylamino)thiazol-5-yl)acetic acid |

TABLE 2-continued

Aminothiazole Compounds

| Compound | Structure | Chemical Name |
|---|---|---|
| CaCC$_{inh}$-B06 | 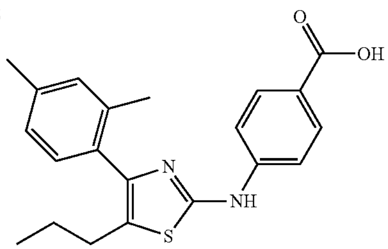 [SMILES: CCCc1sc(Nc2ccc(C(=O)O)cc2)nc1-c1ccc(C)cc1C] | 4-(4-(2,4-dimethylphenyl)-5-propylthiazol-2-ylamino)benzoic acid |
| CaCC$_{inh}$-B07 | 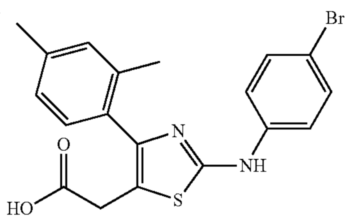 [SMILES: Cc1ccc(-c2nc(Nc3ccc(Br)cc3)sc2CC(=O)O)c(C)c1] | 2-(2-(4-bromophenylamino)-4-(2,4-dimethylphenyl)thiazol-5-yl)acetic acid |
| CaCC$_{inh}$-B08 | 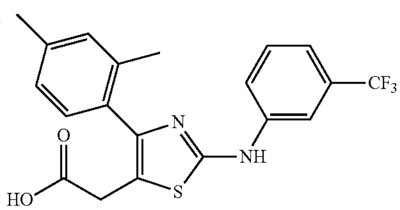 [SMILES: Cc1ccc(-c2nc(Nc3cccc(C(F)(F)F)c3)sc2CC(=O)O)c(C)c1] | 2-(4-(2,4-dimethylphenyl)-2-(3-(trifluoromethyl)phenylamino)thiazol-5-yl)acetic acid |
| CaCC$_{inh}$-B09 | 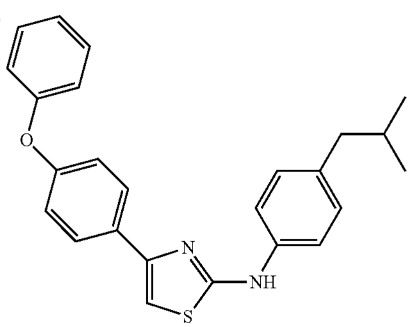 [SMILES: CC(C)Cc1ccc(Nc2nc(-c3ccc(Oc4ccccc4)cc3)cs2)cc1] | N-(4-isobutylphenyl)-4-(4-phenoxyphenyl)thiazol-2-amine |
| CaCC$_{inh}$-B10 | 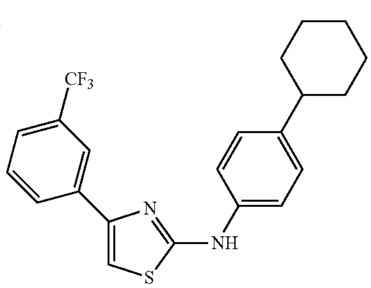 [SMILES: FC(F)(F)c1cccc(-c2csc(Nc3ccc(C4CCCCC4)cc3)n2)c1] | N-(4-cyclohexylphenyl)-4-(3-(trifluoromethyl)phenyl)thiazol-2-amine |

TABLE 2-continued

Aminothiazole Compounds

| Compound | Structure | Chemical Name |
|---|---|---|
| CaCC$_{inh}$-B11 | 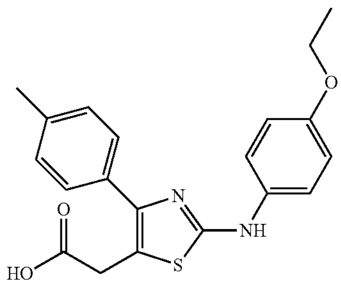 [SMILES: CCOc1ccc(Nc2nc(-c3ccc(C)cc3)c(CC(=O)O)s2)cc1] | 2-(2-(4-ethoxyphenylamino)-4-p-tolylthiazol-5-yl)acetic acid |
| CaCC$_{inh}$-B12 | 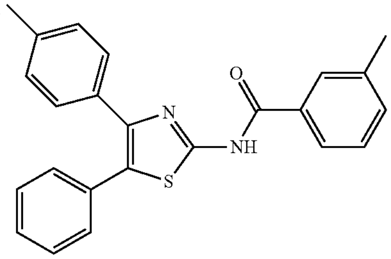 | 3-methyl-N-(5-phenyl-4-p-tolylthiazol-2-yl)benzamide |
| CaCC$_{inh}$-B13 | 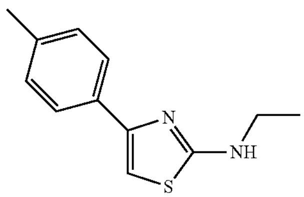 | N-ethyl-4-p-tolylthiazol-2-amine |
| CaCC$_{inh}$-B14 | 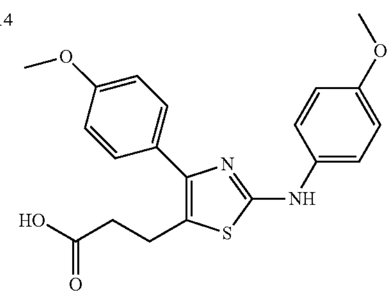 | 3-(4-(4-methoxyphenyl)-2-(4-methoxyphenylamino)thiazol-5-yl)propanoic acid |

The agents, including the aminothiophene compounds having the structure of formula I and substructures of formula IA, Ia-Ii and aminothiazole compounds having the structure of formula II and substructures of formula IIa-IIh as described herein, are capable of inhibiting or blocking a CaCC channel or pore (blocking or impeding activation of a CaCC channel or pore) located in the outer cell membrane of a cell and thus inhibiting CaCC chloride conductance. Also provided herein are methods of inhibiting a calcium-activated chloride channel comprising contacting a cell (e.g., as an epithelial cell, including an intestinal epithelial cell and a lung epithelial cell) that comprises at least one calcium-activated chloride channel with a compound (or composition comprising the compound) (e.g., a aminothiophene compound having the structure of formula I and substructures of formula I(A), Ia-Ii or an aminothiazole compound having the structure of formula II and substructures of formula IIa-IIh), under conditions and for a time sufficient for the cell and the compound to interact, and in an amount effective to inhibit activation of the channel.

The aminothiophene compounds having the structure of formula I and substructures of formula I(A) and Ia-Ii or an aminothiazole compound having the structure of formula II and substructures of formula IIa-IIh and compositions comprising these compounds are useful for treating a condition, disease or disorder in a subject that is characterized by, caused by, or exacerbated by aberrantly increased calcium-activated chloride channel activity. As described in greater detail herein, such diseases and disorders include diseases and disorders related to (or associated with) excess intestinal secretion of fluids, such as secretory diarrhea, and diseases and disorders associated with excess mucus production, such as cystic fibrosis, asthma, chronic obstructive pulmonary disease, and bronchiectasis. The compounds and compositions comprising the compounds may be used to inhibit (i.e., decrease or reduce) fluid secretion from a cell, particularly a cell from which fluid secretion is abnormally increased, which in part, may result from aberrantly increased chloride conductance through a CaCC. These compounds and compositions may be contacted with the cell (or administered to a subject in need thereof) in an amount effective to inhibit (decrease or reduce) chloride conductance through at least one calcium-activated chloride channel, which thereby results in decreased chloride secretion and decreased fluid secretion from the cell. In certain embodiments of the methods described herein, the cell, which comprises at least one calcium-activated chloride channel, may be an epithelial cell, which in certain embodiments is an intestinal epithelial cell or a pulmonary epithelial cell.

Chemistry Definitions

Certain chemical groups named herein are preceded by a shorthand notation indicating the total number of carbon atoms that are to be found in the indicated chemical group. For example, $C_1$-$C_6$ alkyl describes an alkyl group, as defined below, having a total of 1 to 6 carbon atoms, and $C_5$-$C_7$ cycloalkyl describes a cycloalkyl group, as defined below, having a total of 5 to 7 carbon atoms. The total number of carbons in the shorthand notation does not include carbons that may exist in substituents of the group described. In addition to the foregoing, as used herein, unless specified to the contrary, the following terms have the meaning indicated.

"Alkyl" means a straight chain or branched, noncyclic or cyclic, unsaturated or saturated aliphatic hydrocarbon containing from 1 to 10 carbon atoms, while the terms "$C_{1-4}$ alkyl" and "$C_{1-6}$ alkyl" have the same meaning as alkyl but contain from 1 to 4 carbon atoms and 1 to 6 carbon atoms, respectively. A lower alkyl refers to an alkyl that has any number of carbon atoms between 1 and 6. Representative saturated straight chain alkyls include methyl, ethyl, n-propyl, n-butyl, n-pentyl, n-hexyl, and the like, while saturated branched alkyls include isopropyl, sec-butyl, isobutyl, tert-butyl, tert-pentyl, heptyl, n-octyl, isopentyl, 2-ethylhexyl and the like. Representative saturated cyclic alkyls include cyclopropyl, cyclobutyl, cyclopentyl, cyclohexyl, —CH$_2$cyclopropyl, —CH$_2$cyclobutyl, —CH$_2$cyclopentyl, —CH$_2$cyclohexyl, and the like; unsaturated cyclic alkyls include cyclopentenyl and cyclohexenyl, and the like. Cyclic alkyls, also referred to as "homocyclic rings," include di- and poly-homocyclic rings such as decalin and adamantyl.

Unsaturated alkyls contain at least one double or triple bond between adjacent carbon atoms (referred to as an "alkenyl" or "alkynyl," respectively). "Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain may be optionally substituted by one or more of the following substituents: halo, cyano, nitro, aryl, cycloalkyl, heterocyclyl, heteroaryl, oxo, thioxo, trimethylsilanyl, —OR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_p$R$^a$ (where p is 0, 1 or 2), and —S(O)$_t$N(R$^a$)$_2$ (where t is 1 or 2) where each R$^a$ is independently hydrogen, alkyl, haloalkyl, carbocyclyl carbocyclylalkyl, aryl, aralkyl, heterocyclyl, heterocylylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain may be optionally substituted by one or more of the following substituents: halo, cyano, nitro, aryl, cycloalkyl, heterocyclyl, heteroaryl, oxo, thioxo, trimethylsilanyl, —OR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_p$R$^a$ (where p is 0, 1 or 2), and —S(O)$_t$N(R$^a$)$_2$ (where t is 1 or 2) where each R$^a$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl, and where each of the above substituents is unsubstituted unless otherwise indicated.

Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; representative straight chain and branched alkynyls include acetylenyl, propynyl, 1-butynyl, 2-butynyl, 1-pentynyl, 2-pentynyl, 3-methyl-1 butynyl, and the like.

It is understood that within the context of the compounds described herein that the terms alkyl, aryl, arylalkyl, heterocycle, homocycle, and heterocycloalkyl are taken to comprise unsubstituted alkyl and substituted alkyl, unsubstituted aryl and substituted aryl, unsubstituted arylalkyl and substituted arylalkyl, unsubstituted heterocycle and substituted heterocycle, unsubstituted homocycle and substituted homocycle, unsubstituted heterocycloalkyl and substituted heterocyclealkyl, respectively, as defined herein, unless otherwise specified.

As used herein, the term "substituted" in the context of alkyl, alkoxy, aryl, arylalkyl, cycloalkyl, heterocycle, and heterocycloalkyl means that at least one hydrogen atom of the alky, aryl, arylalkyl, heterocycle, or heterocycloalkyl moiety is replaced with a substituent. The term "optionally substituted" as used in the context of an optionally substituted alkyl, alkoxy, aryl, arylalkyl, cycloalkyl, heterocycle, and heterocycloalkyl means that when the alkyl, alkoxy, aryl, arylalkyl, cycloalkyl, heterocycle, and heterocycloalkyl, respectively, is substituted, t least one hydrogen atom of the alky, aryl, arylalkyl, heterocycle, or heterocycloalkyl moiety is replaced with a substituent. In the instance of an oxo substituent ("=O") two hydrogen atoms are replaced. A "substituent" as used within the context of this disclosure includes oxo, halogen, hydroxy, cyano, nitro, amino, alkylamino, dialkylamino, alkyl, alkoxy, thioalkyl, haloalkyl, substituted alkyl, heteroalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocycloalkyl, substituted heterocycloalkyl, —NR$_a$R$_b$, —NR$_a$C(=O)R$_b$, —NR$_a$C(=O)NR$_a$R$_b$, —NR$_a$C(=O)OR$_b$—NR$_a$S(=O)$_2$R$_b$, —OR$_a$, —C(=O)R$_a$—C(=O)OR$_a$, —C(=O)NR$_a$R$_b$, —OCH$_2$C(=O)NR$_a$R$_b$, —OC(=O)NR$_a$R$_b$, —SH, —SR$_a$, —SOR$_a$, —S(=O)$_2$NR$_a$R$_b$, —S(=O)$_2$R$_a$, —SR$_a$C(=O)

$NR_aR_b$, $-OS(=O)_2R_a$ and $-S(=O)_2OR_a$ (also written as $-SO_3R_a$), wherein $R_a$ and $R_b$ are the same or different and independently hydrogen, alkyl, haloalkyl, substituted alkyl, alkoxy, aryl, substituted aryl, arylalkyl, substituted arylalkyl, arylalkoxy, heteroaryl, substituted heteroaryl, heteroarylalkyl, substituted heteroarylalkyl, heterocycle, substituted heterocycle, heterocycloalkyl or substituted heterocycloalkyl. The definitions of $R_a$ and $R_b$ above apply to all uses of these substituents throughout the description.

Representative substituents include (but are not limited to) alkoxy (i.e., alkyl-O—, including $C_{1-6}$ alkoxy and $C_{1-4}$ alkoxy (e.g., methoxy, ethoxy, propoxy, butoxy)), aryloxy (e.g., phenoxy, chlorophenoxy, tolyloxy, methoxyphenoxy, benzyloxy, alkyloxycarbonylphenoxy, alkyloxycarbonyloxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonyl-phenylthio), amino (e.g., amino, mono- and di-$C_1$-$C_3$ alkanylamino, methylphenylamino, methylbenzylamino, $C_1$-$C_3$ alkanylamido, acylamino, carbamamido, ureido, guanidino, nitro and cyano). Moreover, any substituent may have from 1-5 further substituents attached thereto.

"Aryl" means an aromatic carbocyclic moiety such as phenyl or naphthyl (i.e., naphthalenyl) (1- or 2-naphthyl) or anthracenyl (e.g., 2-anthracenyl).

"Arylalkyl" (e.g., phenylalkyl) means an alkyl having at least one alkyl hydrogen atom replaced with an aryl moiety, such as —$CH_2$-phenyl, —CH=CH-phenyl, —$C(CH_3)$=CH-phenyl, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl (including 6-quinolinyl), isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —$CH_2$pyridinyl, —$CH_2$pyrimidinyl, and the like.

"Heterocycle" (also referred to herein as "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined herein. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

Phenylamino refers to —N($R_a$)-phenyl. The phenyl may be optionally substituted as described herein, for example, with $C_1$-$C_6$ alkoxy (such as methoxy or ethyoxy) or $C_1$-$C_6$ alkyl (e.g., methyl or ethyl).

Phenylacyl refers to —C(O)-phenyl. Phenyl may be optionally substituted with substituents $R_a$ described herein.

"Heterocycloalkyl" means an alkyl having at least one alkyl hydrogen atom replaced with a heterocycle, such as —$CH_2$morpholinyl, —$CH_2CH_2$piperidinyl, —$CH_2$azepineyl, —$CH_2$pirazineyl, —$CH_2$pyranyl, —$CH_2$furanyl, —$CH_2$pyrolidinyl, and the like.

"Homocycle" (also referred to herein as "homocyclic ring") means a saturated or unsaturated (but not aromatic) carbocyclic ring containing from 3-7 carbon atoms, such as cyclopropane, cyclobutane, cyclopentane, cyclohexane, cycloheptane, cyclohexene, and the like.

"Halogen" or "halo" means fluoro, chloro, bromo, and iodo.

"Haloalkyl," which is an example of a substituted alkyl, means an alkyl having at least one hydrogen atom replaced with halogen, such as trifluoromethyl and the like.

"Haloaryl," which is an example of a substituted aryl, means an aryl having at least one hydrogen atom replaced with halogen, such as 4-fluorophenyl and the like.

"Alkoxy" means an alkyl moiety attached through an oxygen bridge (i.e., —O-alkyl) such as methoxy, ethoxy, and the like.

"COOH" means a carboxy and may also be set forth as —C(=O)OH.

"Haloalkoxy," which is an example, of a substituted alkoxy, means an alkoxy moiety having at least one hydrogen atom replaced with halogen, such as chloromethoxy and the like.

"Alkoxydiyl" means an alkyl moiety attached through two separate oxygen bridges (i.e., —O-alkyl-O—) such as —O—$CH_2$—O—, —O—$CH_2CH_2$—O—, —O—$CH_2CH_2CH_2$—O—, —O—$CH(CH_3)CH_2CH_2$—O—, —O—$CH_2C(CH_3)_2CH_2$—O—, and the like.

"Alkanediyl" means a divalent alkyl from which two hydrogen atoms are taken from the same carbon atom or from different carbon atoms, such as —$CH_2$—, —$CH_2CH_2$—, —$CH_2CH_2CH_2$—, —$CH(CH_3)CH_2CH_2$—, —$CH_2C(CH_3)_2CH_2$—, and the like.

"Thioalkyl" means an alkyl moiety attached through a sulfur bridge (i.e., —S— alkyl) such as methylthio, ethylthio, and the like.

"Alkylamino" and "dialkylamino" mean one or two alkyl moieties attached through a nitrogen bridge (i.e., —N-alkyl) such as methylamino, ethylamino, dimethylamino, diethylamino, and the like.

"Carbamate" is —$R_aOC(=O)NR_aR_b$.

"Cyclic carbamate" means any carbamate moiety that is part of a ring.

"Amidyl" is —$NR_aR_b$.

"Hydroxyl" or "hydroxy" refers to the —OH radical.

"Sulfhydryl" or "thio" is —SH.

"Amino" refers to the —$NH_2$ radical.

"Nitro" refers to the —$NO_2$ radical.

"Imino" refers to the =NH radical.

"Thioxo" refers to the =S radical.

"Cyano" refers to the —C≡N radical.

"Sulfonamide refers to the radical —$S(=O)_2NH_2$.

"Isocyanate" refers to the —N=C=O radical.

"Isothiocyanate" refers to the —N=C=S radical.

"Azido" refers to the —N=$N^+$=$N^-$ radical.

"Carboxy" refers to the —$CO_2H$ radical (also depicted as —C(=O)OH and —COOH).

"Hydrazide" refers to the —C(=O)$NR_a$—$NR_aR_b$ radical.

"Oxo" refers to the =O radical.

The compounds described herein may generally be used as the free acid or free base. Alternatively, the compounds may be used in the form of acid or base addition salts. Acid addition salts of the free base amino compounds may be prepared according to methods well known in the art, and may be formed from organic and inorganic acids. Suitable organic acids include (but are not limited to) maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include (but are not limited to) hydrochloric, hydrobromic, sulfuric, phosphoric, and nitric acids. Base addition salts of the free acid compounds of the compounds described herein may also be prepared by methods well known in the art, and may be formed from organic and inorganic bases. Suitable inorganic bases included (but are not limited to) the hydroxide or other salt of sodium, potassium, lithium, ammonium, calcium, magnesium, iron, zinc, copper, manganese, aluminum, and the like, and organic bases such as substituted ammonium salts. Thus, the term "pharmaceutically acceptable salt" of structure (I) or of structure (II), as well as any and all substructures described herein, is intended to encompass any and all pharmaceutically suitable salt forms.

Also contemplated are prodrugs of any of the compounds described herein. Prodrugs are any covalently bonded carriers that release a compound of structure (I), as well as any of the substructures herein, in vivo when such prodrug is administered to a subject. Prodrugs are generally prepared by modifying functional groups in a way such that the modification is cleaved, either by routine manipulation or by an in vivo process, yielding the parent compound. Prodrugs include, for example, compounds described herein when, for example, hydroxy or amine groups are bonded to any group that, when administered to a subject, is cleaved to form the hydroxy or amine groups. Thus, representative examples of prodrugs include (but are not limited to) acetate, formate and benzoate derivatives of alcohol and amine functional groups of the compounds of structure (I), as well as any of the substructures herein. Further, in the case of a carboxylic acid (—COOH), esters may be employed, such as methyl esters, ethyl esters, and the like. Prodrug chemistry is conventional to and routinely practiced by a person having ordinary skill in the art.

Prodrugs are typically rapidly transformed in vivo to yield the parent compound (i.e., an aminothiophene compound having a structure I or substructures Ia-Ii; or an aminothiazole compound having a structure II or substructures IIa-Ih), for example, by hydrolysis in blood. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

With regard to stereoisomers, the compounds of structure (I) and structure (II), as well as any substructure herein, may have one or more chiral centers and may occur in any isomeric form, including racemates, racemic mixtures, and as individual enantiomers or diastereomers. In addition, the compounds of structure (I) and structure (II), as well as any substructure thereof, include E and Z isomers of all double bonds. All such isomeric forms of the compounds are included and contemplated, as well as mixtures thereof.

Furthermore, some of the crystalline forms of any compound described herein may exist as polymorphs, which are also included and contemplated by the present disclosure. In addition, some of the compounds may form solvates with water or other organic solvents. Such solvates are similarly included within the scope of compounds and compositions described herein.

In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books and databases. Suitable reference books and treatises that detail the synthesis of reactants useful in the preparation of compounds and bioactive agents described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions," 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds and agents described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G.

"Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the compounds and bioactive agents described herein is P. H. Stahl & C. G. Wermuth "Handbook of Pharmaceutical Salts," Verlag Helvetica Chimica Acta, Zurich, 2002.

Synthesis of Aminothiophene and Aminothiazole Compounds

Synthesis of Aminothiophene Compounds

The compounds described herein may be prepared by known organic synthesis techniques, including the methods described in more detail in the Examples. In general, the compounds of structure (I) above may be made by the following Reaction Scheme 1, wherein all substituents are as defined above unless indicated otherwise.

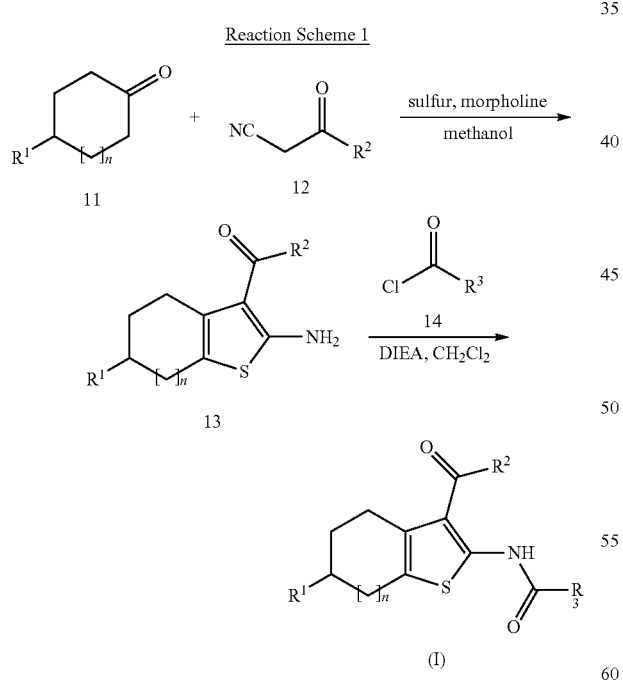

Referring to Reaction Scheme 1, ketones of formula 11 and cyanoacetates of formula 12 can be purchased or prepared according to procedures known to those skilled in the art. Compounds of formula 11 and 12 can be reacted together in the presence of elemental sulfur and morpholine in a solvent, such as methanol, to obtain compounds of formula 13. Acid chlorides of formula 14 can be purchased or prepared according to procedures known to those skilled in the art and reacted with compounds of formula 3 in the presence of an appropriate base, such as diisopropylethylamine (DIEA), in a solvent, such as dichloromethane, to obtain compounds of formula (I) and (I(A)). One skilled in the art will recognize that appropriate protection/deprotection chemistry may be required to obtain the desired compound of formula (I) and (I(A)).

In general, the compounds of structure (II) above may be made by the following Reaction Scheme 2, wherein all substituents are as defined above unless indicated otherwise.

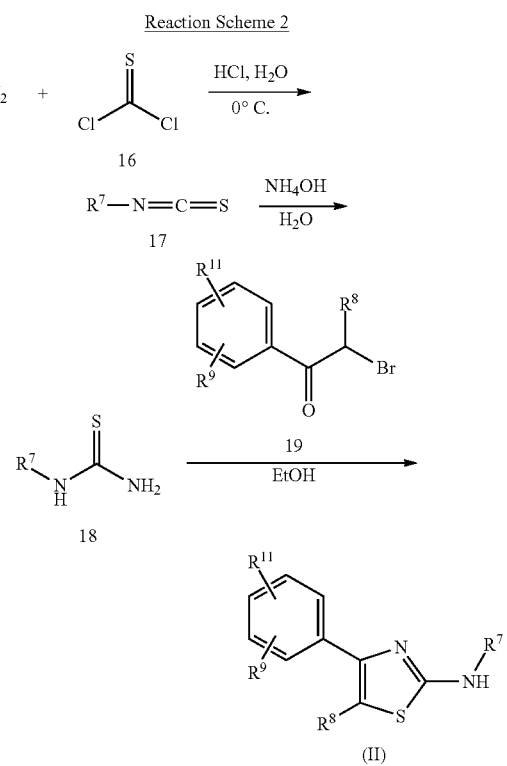

Referring to Reaction Scheme 2, amines of formula 15 can be purchased or prepared according to methods known to those skilled in the art and reacted with thiophosgene (16) in the presence of water and an appropriate acid, such as hydrochloric acid, at 0° C. to obtain thioisocyanates of formula 17. Compounds of formula 17 can then be treated with aqueous ammonium hydroxide to obtain thioamides of formula 18. Bromoketones of formula 19 can be purchased or prepared according to methods known to those skilled in the art and reacted with compounds of formula 18 to obtain compounds of formula (II). One skilled in the art will recognize that appropriate protection/deprotection chemistry may be required to obtain the desired compound of formula (II).

Methods of Using the Compounds and Pharmaceutical Compositions

As described herein, the aminothiophene and aminothiazole compounds are capable of inhibiting CaCC activity (i.e., inhibiting, reducing, decreasing, blocking conductance of chloride ion (i.e., chloride) in the CaCC channel or pore in a statistically significant or biologically significant manner) in a cell and may be used for treating diseases, disorders, and conditions that result from, are associated with, or are related to aberrantly increased CaCC activity and which conditions, diseases, and disorders are thereby treatable by inhibiting CaCC activity (including inhibiting activation of a CaCC), which inhibits (decreases or reduces) chloride conductance through the CaCC and inhibits fluid secretion (or water secretion) from the cell (i.e., efflux of chloride and water). Accordingly, methods of inhibiting chloride conductance or movement through a CaCC are provided herein that comprise contacting a cell (e.g., an epithelial cell including an intestinal epithelial cell and a lung epithelial cell) that comprises at least one CaCC in the outer membrane of the cell (i.e., a cell that expresses a CaCC and has channels or pores formed by the CaCC in the cell membrane) with any one or more of the compounds described herein, under conditions and for a time sufficient for the CaCC and the compound to interact. Inhibiting movement of chloride and water through the at least one CaCC thereby inhibits (or decreases) fluid secretion from the cell. A CaCC that may be inhibited by any one or more of the compounds or compositions described herein includes but is not limited to TMEM16A.

Accordingly, in one embodiment a method is provided for treating a condition, disease, or disorder that is associated with abnormally increased chloride ion conductance by administering to a subject, in need thereof, a composition comprising at least one aminothiophene compound (a compound having structure I or a substructure thereof) and/or at least one aminothiazole compound (a compound having structure II or a substructure thereof), or composition comprising the at least one compound, which are described in detail herein. The compound is administered in an amount effective to inhibit a calcium-activated chloride channel or to inhibit activation of the CaCC, thereby inhibiting chloride ion conductance and consequently inhibiting fluid secretion from the cell.

In certain embodiments, such as for practicing an in vitro assay method described herein, the cell may be obtained from a subject or from a biological sample. A biological sample may be a blood sample (from which serum or plasma may be prepared and cells isolated), biopsy specimen, body fluids (e.g., lung lavage, sputum, ascites, mucosal washings, synovial fluid, peritoneal washing), bone marrow, lymph nodes, tissue explant, organ culture, or any other tissue or cell preparation from a subject or a biological source. A biological sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a biological sample derived from a subject or biological source. The subject or biological source may be a human or non-human animal, a primary cell culture (e.g., epithelial cells isolated from intestinal or lung tissue, or virus infected cells), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

Diseases and disorders that may be treated by administering a composition comprising a compound of structure I and related substructures or a compound of structure II and any related substructure described herein include aberrantly increased intestinal fluid secretion, such as secretory diarrhea. Secretory diarrhea can result from exposure to a variety of enteropathogenic organisms (i.e., enteric pathogen) including, without limitation, bacteria such as cholera (*Vibrio cholera*), *E. coli* (particularly enterotoxigenic (ETEC)), *Shigella, Salmonella, Campylobacter, Clostridium difficile*; parasites (e.g., *Giardia, Entamoeba histolytica, Cryptosporidiosis, Cyclospora*); and diarrheal viruses (e.g., rotavirus, Group A and Group C; norovirus, sapovirus). Secretory diarrhea may also be a disorder or sequelae associated with food poisoning, or exposure to a toxin including an enterotoxin such as cholera toxin, a *E. coli* toxin, a *Salmonella* toxin, a *Campylobacter* toxin, or a *Shigella* toxin.

Other secretory diarrheas that may be treated by administering the compounds and compositions comprising the compounds described herein include diarrhea associated with or that is a sequelae of AIDS, diarrhea that is a condition related to the effects of anti-AIDS medications such as protease inhibitors, diarrhea that is a condition or is related to administration of chemotherapeutic compounds, inflammatory gastrointestinal disorders, such as ulcerative colitis, inflammatory bowel disease (IBD), Crohn's disease, diverticulosis, and the like. Intestinal inflammation modulates the expression of three major mediators of intestinal salt transport and may contribute to diarrhea in ulcerative colitis both by increasing transepithelial Cl$^-$ secretion and by inhibiting the epithelial NaCl absorption (see, e.g., Lohi et al., *Am. J. Physiol. Gastrointest. Liver Physiol.* 283:G567-75 (2002)).

Other diseases or disorders that may be treated by administering to a subject in need thereof, the compounds (aminothiophene compounds having the structure of formula I and substructures of formula I(A), Ia-Ii and aminothiazole compounds having the structure of formula II and substructures of formula IIa-IIh) include diseases and disorders associated with abnormally increased mucus secretion (i.e., abnormally increased mucus secretion is a condition associated with or is a sequelae of the disease or disorder). Accordingly, the compounds and compositions thereof may be used for treating asthma, cystic fibrosis, bronchiectasis, and chronic pulmonary disease (see, e.g., Wang et al., *Cell Biol. Int.* 31(11):1388-95 (2007), Epub 2007 Jun. 29; Yasuo et al., *Respiration* 73:347-359 (2006); Shale et al., *Eur. Respir. J.* 23:797-798 (2004); Wang et al., *Chinese Med. J.* 120:1051-57 (2007); Barnes, *Curr. Drug Targets Inflamm. Allergy.* 4:675-83 (2005); Cuthbert, *J. R. Soc. Med.* 99:30-35 (2006); Hegab et al., *Chest* 131:1149-56 (2007)).

Methods are also provided herein for treating a disease or disorder associated with abnormally or aberrantly increased chloride ion secretion, wherein the methods comprise administering to a subject (in need thereof) any one (or more) of the compounds, or compositions comprising the compounds, described herein, wherein ion movement (particularly chloride ion conductance or current) by CaCC is inhibited. A subject includes a human and non-human animal. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals. In certain embodiments, methods for treating secretory diarrheas are provided herein, comprising administering to a subject any one (or more) aminothiophene or aminothiazole compounds described herein (or compositions comprising the any one or more compounds) in combination with an agent that inhibits CFTR. Exemplary compounds that may be used to inhibit CFTR include, but are not limited to, thiazolidinone compounds and hydrazide compounds (see, e.g., thiazolidinone compounds (e.g., 3-[(3-trifluoromethyl)phenyl]-5-[(4-carboxyphenyl)methylene]-2-thioxo-4-thiazolidinone (referred to herein as CFTRinh-172)) and hydrazide compounds (see, e.g., U.S. Pat. No. 7,235,573; U.S. Patent Application Publication No. 2005-0239740; Muanprasat et al., *J. Gen. Physiol.* 124:125-37 (2004); Ma et al., *J. Clin. Invest.* 110:1651-58 (2002)).

The aminothiophene compounds having the structure of formula I and substructures of formula Ia-Ii and aminothiazole compounds having the structure of formula II and substructures of formula IIa-IIh, as described herein, may be formulated in a pharmaceutical composition for use in treatment, which includes preventive treatment, of a disease or disorder manifested by increased intestinal fluid secretion, such as secretory diarrhea or that is associated with excess (i.e., abnormally increased) mucus secretion (i.e., abnormally increased mucus secretion is a condition associated with or is a sequelae of the disease or disorder). A pharmaceutical composition may be a sterile aqueous or non-aqueous solution, suspension or emulsion, which additionally comprises a physiologically acceptable excipient (also called a pharmaceutically acceptable or suitable excipient or carrier) (i.e., a non-toxic material that does not interfere with the activity of the active ingredient). Such compositions may be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable excipient or carrier known to those of ordinary skill in the art for use in pharmaceutical compositions may be employed in the compositions described herein. Excipients for therapeutic use are well known, and are described, for example, in *Remington: The Science and Practice of Pharmacy* (Gennaro, 21$^{st}$ Ed. Mack Pub. Co., Easton, Pa. (2005)). In general, the type of excipient is selected based on the mode of administration. Pharmaceutical compositions may be formulated for any appropriate manner of administration, including, for example, topical, oral, nasal, intrathecal, rectal, vaginal, intraocular, subconjunctival, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above excipients or a solid excipient or carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

A composition comprising an aminothiophene compound having the structure of formula I and substructures of formula IA, Ia-Ii and aminothiazole compound having the structure of formula II and substructures of formula IIa-IIh may be formulated for sustained or slow release. Such compositions may generally be prepared using well known technology and administered by, for example, oral, rectal or subcutaneous implantation, or by implantation at the desired target site. Sustained-release formulations may contain an agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release, and the nature of the condition to be treated or prevented.

The dose of the composition for treating a disease or disorder associated with aberrant CaCC function, including but not limited to intestinal fluid secretion, secretory diarrhea, such as a toxin-induced diarrhea, or secretory diarrhea associated with or a sequelae of an enteropathogenic infection, Traveler's diarrhea, ulcerative colitis, irritable bowel syndrome (IBS), AIDS, chemotherapy and diseases or conditions described herein associated with overproduction or excess secretion of mucus (e.g., asthma, chronic obstructive pulmonary disorder, bronchiectasis) may be determined according to parameters understood by a person skilled in the medical art. Accordingly, the appropriate dose may depend upon the subject's condition, that is, stage of the disease, general health status, as well as age, gender, and weight, and other factors considered by a person skilled in the medical art.

Pharmaceutical compositions may be administered in a manner appropriate to the disease or disorder (or condition) to be treated as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose (or effective dose) and treatment regimen provides the composition(s) in an amount sufficient to provide therapeutic and/or prophylactic benefit (e.g., an improved clinical outcome, such as more frequent complete or partial remissions, or longer disease-free and/or overall survival, improved quality of life, or a lessening of symptom frequency and/or severity).

Consistent with the understanding in the medical arts, treatment or treating refers to the medical management of a disease or disorder. Clinical assessment of the level of dehydration and/or electrolyte imbalance may be performed to determine the level of effectiveness of a compound and whether dose or other administration parameters (such as frequency of administration or route of administration) should be adjusted. In addition, particularly with respect to chronic diseases such as cystic fibrosis, asthma, COPD, and bronchiectasis, clinical assessment of improvement may be determined by lessening of symptom frequency and/or severity. For example, clinical assessment may include determining the number of hospitalizations, particularly resulting from exacerbations related to bacterial infections. Clinical evaluations patients with such chronic diseases also includes quality of life assessment. Therefore, a patient or subject, particularly a patient that has a chronic disease such as cystic fibrosis, COPD, or bronchiectasis, for example, may be treated by administering to the subject the compounds and compositions described herein, and as such the treatment has a therapeutic or prophylactic benefit.

Optimal doses may generally be determined using experimental models and/or clinical trials. The optimal dose may depend upon the body mass, weight, or blood volume of the subject. In general, the amount of a small molecule compound as described herein, that is present in a dose, ranges from about 0.01 µg to about 1000 µg per kg weight of the host. The use of the minimum dose that is sufficient to provide effective therapy is usually preferred. Subjects may generally be monitored for therapeutic effectiveness using assays suitable for the condition being treated or prevented, which assays will be familiar to those having ordinary skill in the art and are described herein.

Other embodiments and uses will be apparent to one skilled in the art in light of the present disclosures. The following examples are provided merely as illustrative of various embodiments and shall not be construed to limit the invention in any way.

EXAMPLES

Example 1

Cell-Based Assay to Identify Calcium-Activated Chloride Channel Inhibitors

HT-29 cells (ATCC HTB-38) were obtained from the American Type Culture Collection (Manassas, Va.) and grown in DMEM supplemented with 10% fetal bovine serum (FBS), 100 units/ml penicillin, and 100 µg/ml streptomycin. T84 cells were maintained in DMEM/F12 (1:1) medium containing 10% FBS, 100 units/ml penicillin and 100 µg/ml streptomycin. Fisher rat thyroid (FRT) expressing human CFTR and YFP-H148Q/I152L were generated as described (Ma et al., *J. Clin. Invest.* 110:1651-8 (2002)), and grown in F-12 Modified Coon's medium supplemented with 10% FBS, 2 mM glutamine, 100 units/ml penicillin, and 100 µg/ml streptomycin. All cells were grown at 37° C. in 5% $CO_2$/95% air.

Figure 1B:
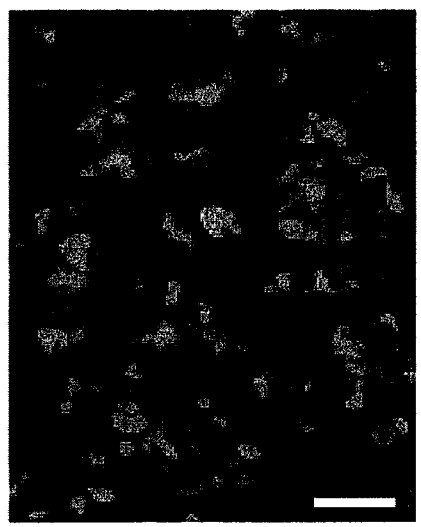

HT-29 cells were infected with a lentivirus encoding YFP-H148Q/I152L according to molecular biology methods routinely practiced by persons skilled in the art. Prior to infection, HT-29 cells were cultured in 90-mm diameter plates until ~80% confluent in McCoy's 5a medium supplemented with 1.5 mM L-glutamine, 10% FBS, and 2.2 g/L sodium bicarbonate. The cells were washed three times with PBS, and then 1 ml of high-titer lentiviral supernatant was added to each well in the presence of 8 µg/ml polybrene. The cells were incubated at 37° C. in 5% $CO_2$/95% air for 6 hours, and medium was then replaced with the regular DMEM growth medium described above. YFP expression was detected 48 h after infection. As depicted in FIG. 1B, HT-29 cells stably expressing YFP-H148Q/I152L were brightly fluorescent, with nearly all cells having fluorescence. This particular YFP indicator (YFP-H148Q/I152L) used for screening was 50% quenched by ~3 mM iodide.

For experiments with thapsigargin or calcimycin, cells in 96-well plates at 100% confluence were washed 3 times with PBS, incubated with test compounds at 32.5 µM for 5 min in PBS in a final volume of 60 µl/well, and then incubated with 2 µM thapsigargin for 7 min or 10 µM calcimycin for 3 min before assay of iodide influx.

Figure 2A:
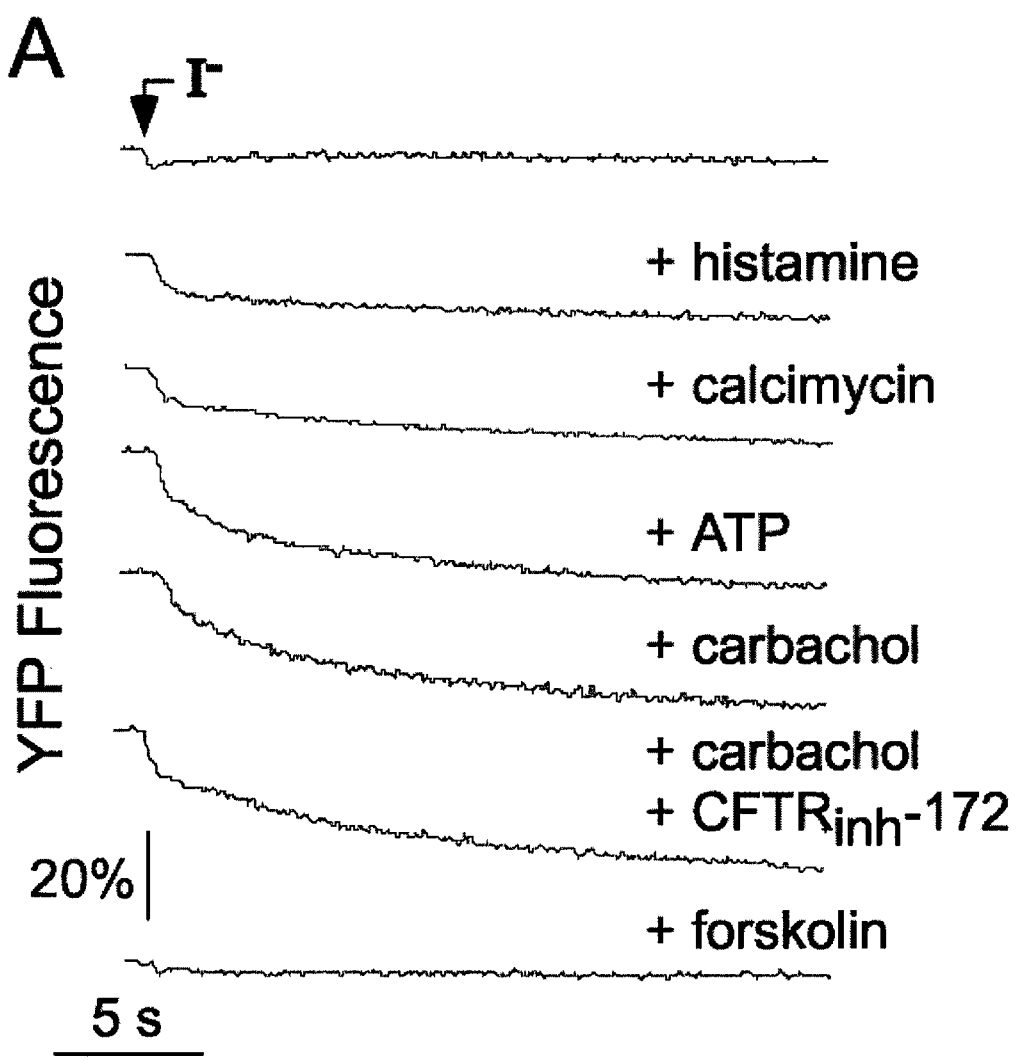
FIG. 2A-2D present data illustrating time course experiments that measure YFP fluorescence after extracellular iodide addition to YFP-expressing HT-29 cells. The scale bar on the y-axis indicates the percentage reduction in fluorescence relative to baseline fluorescence (before iodide addition). As indicated in the figures, the solutions contained histamine (100 µM), calcimycin (10 µM), ATP (100 µM), carbachol (100 µM), carbachol (100 µM)+$CFTR_{inh}$-172 (20 µM), or forskolin (20 µM), either individually as shown in FIG. 2A, or in various combinations (at same concentrations) as shown in FIG. 2B.
Figure 2B:
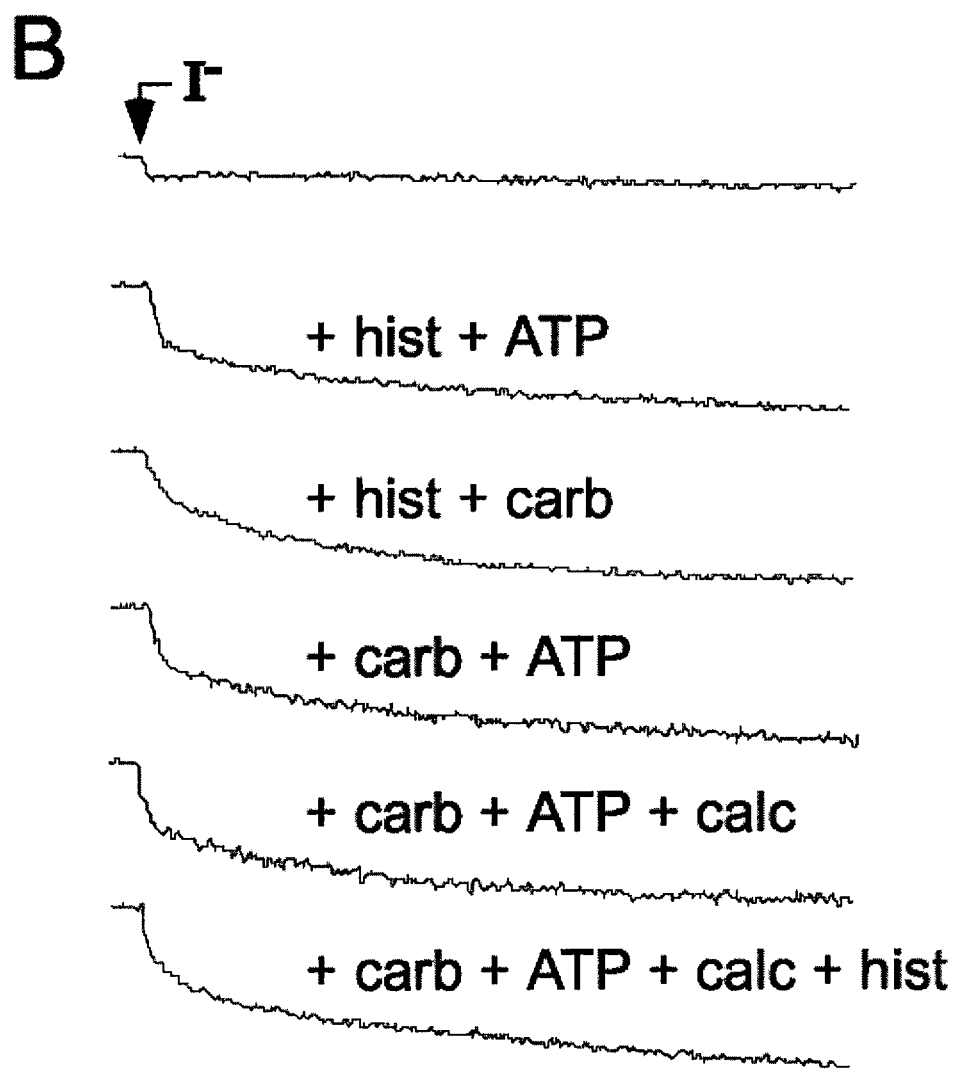

Several CaCC agonists were assayed to establish the cellular model for CaCC inhibitor screening. Histamine (100 µM), calcimycin (10 µM), ATP (100 µM), carbachol (100 µM) and forskolin (10 µM) were tested individually (FIG. 2A) and in combinations (FIG. 2B). The CFTR inhibitor $CFTR_{inh}$-172 (20 µM) was also tested. Of the agonists tested individually, carbachol and ATP produced the strongest responses as indicated by the slopes of the fluorescence decrease following extracellular iodide addition. In combination, carbachol and ATP produced the greatest response observed for the combinations. Increased iodide influx was not observed following forskolin addition, nor did $CFTR_{inh}$-172 inhibit iodide influx in response to calcium agonists, indicating that the cells used in the assay expressed little or no functional CFTR. A combination of carbachol and ATP was selected for compound screening.

Figure 2C:
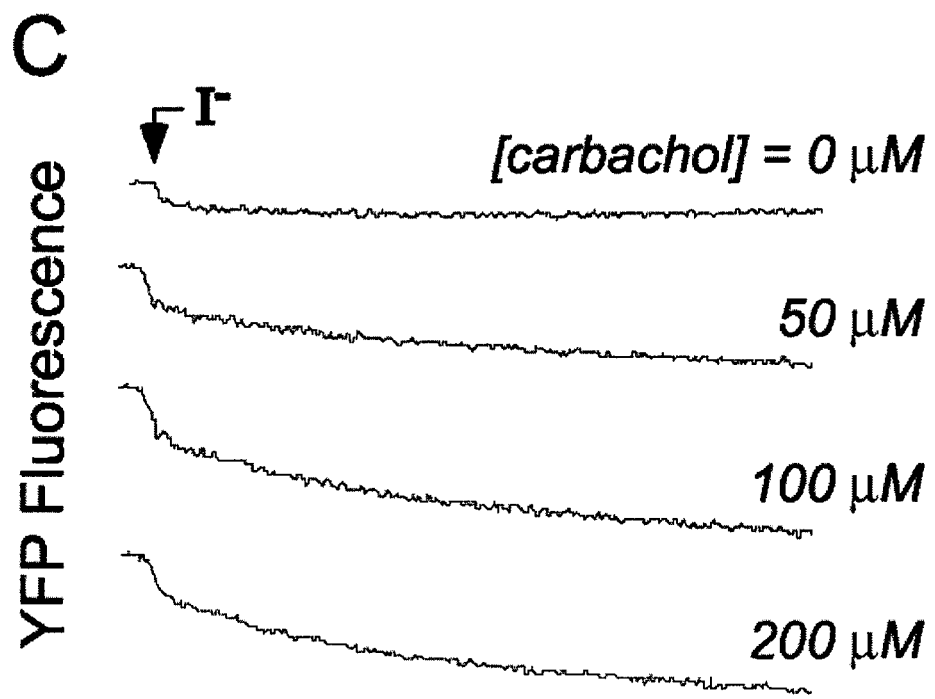
Figure 2D:
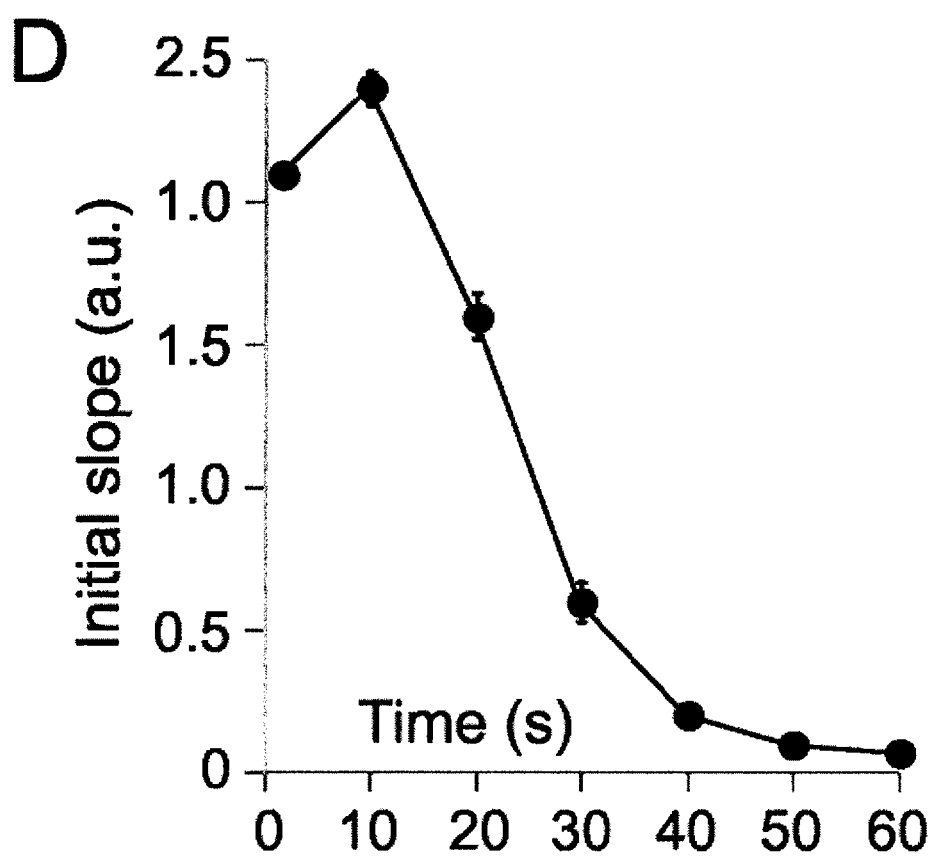

Iodide influx measurements were done to establish agonist concentrations and addition times. Concentration dependence studies for carbachol (FIG. 2C) and ATP indicated maximal responses at 100 µM. FIG. 2D shows reduced iodide influx as a function of time between addition of 100 µM carbachol/ATP and extracellular iodide, which is a consequence of the transient elevation in cytoplasmic calcium produced by these agonists. The greatest iodide influx was observed when agonists were added at ~10 s prior to iodide; however, the influx was not much greater than when agonists were added at the time of iodide addition. Therefore, for high-throughput screening, in part, to simplify assay conditions, agonists (carbachol and ATP, each 100 µM) were added together with iodide.

Compounds for primary screening were purchased from ChemDiv (San Diego, Calif.). The compound collection contained 50,000 diverse, drug-like compounds with >90% of compounds in the molecular size range 200-450 daltons. Compounds for the secondary screening were purchased from ChemDiv and Asinex. Compounds were prepared in 96-well plates (Corning-Costar) as 10 mM solutions in dimethylsulfoxide (DMSO). For the primary screen compounds were tested in groups of 4 compounds per well. The compounds were screened at a concentration 32.5 µM. All chemicals were purchased from SIGMA-ALDRICH (St. Louis, Mo.).

For high-throughput screening, iodide influx was measured in the YFP-expressing HT-29 cells in a 96-well format using an automated workstation capable of assaying more than 10,000 compounds overnight. Screening was performed using a customized screening system (BECKMAN COULTER, Inc., Indianapolis, Ind.) consisting of the SAGIAN Core system integrated with SAMI software, and equipped with an ORCA arm for labware transport, a 96-channel head BIOMEK FX, $CO_2$ incubator, plate washer, bar code reader, delidding station, and two FLUOstar OPTIMA fluorescence plate readers (BMG Labtechnologies, Durham, N.C.), each equipped with syringe pumps and custom excitation/emission filters (500/544 nm; CHROMA, Brattleboro, Vt.).

HT-29 cells expressing YFP-H148Q/I152L were plated in 96-well plates at 70% confluence. Plates were incubated overnight at 37° C., 5% $CO_2$ and then the growth medium was replaced with fresh growth medium. Cells were incubated further until 95% confluence (12-18 h), washed 3 times with PBS, and incubated with the test compounds at 32.5 µM final concentration for 5 min in PBS, in a final volume of 60 μl/well. YFP fluorescence was measured 1 s before and for 30 s after addition of a PBS-iodide solution (PBS that has 100 mM chloride replaced by iodide) containing carbachol and ATP (100 μM each). Each 96-well plate contained 'positive' controls (DMSO vehicle without agonists or test compounds) and 'negative' controls (DMSO vehicle with agonists but without test compounds). In some experiments solutions included (individually or in combination): carbachol, ATP, or histamine (at 50, 100, 150 or 200 μM), calcimycin (10 μM), thapsigargin (2 μM) and $CFTR_{inh}$-172 (20 μM).

Iodide influx (d[I⁻]/dt at t=0) was computed from fluorescence time course data by single exponential regression, as described (Ma et al., *J. Clin. Invest.* 110:1651-8 (2002)). Percentage inhibition was computed as: percentage inhibition=100×($Slope_{negative\ control}$−$Slope_{test\ compound}$)/($Slope_{negative\ control}$−$Slope_{positive\ control}$).

Figure 3A:
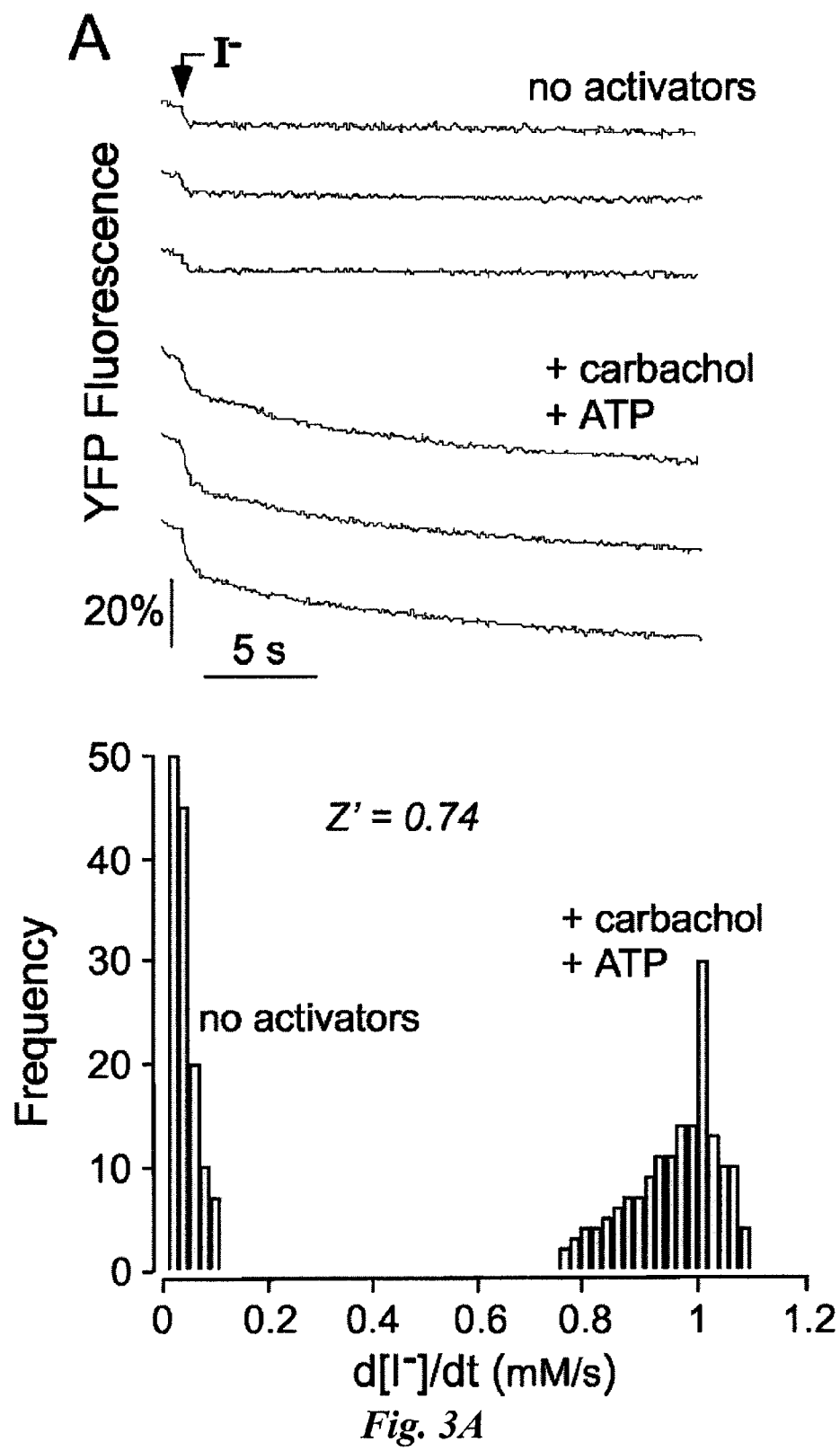
FIG. 3A-3C.

FIG. 3A (left) shows representative YFP fluorescence kinetics measured in single wells of 96-well plates. Each curve consisted of recording of baseline fluorescence for 1 second, followed by 30 seconds of continuous recording of fluorescence after rapid addition of a solution containing iodide and the CaCC agonist combination (carbachol and ATP, each 100 μM). Following a small solution addition artifact, there was little decrease in fluorescence in the absence of activators, compared to a robust reduction in fluorescence with agonists. FIG. 3A (right) shows a frequency histogram of iodide influx rates, d[I⁻]/dt, in individual wells for positive (no agonists) or negative (with agonists) controls. The computed Z'-factor for the assay was very good, 0.74, indicating adequacy of a single compound screening to identify putative CaCC inhibitors.

Figure 3B:
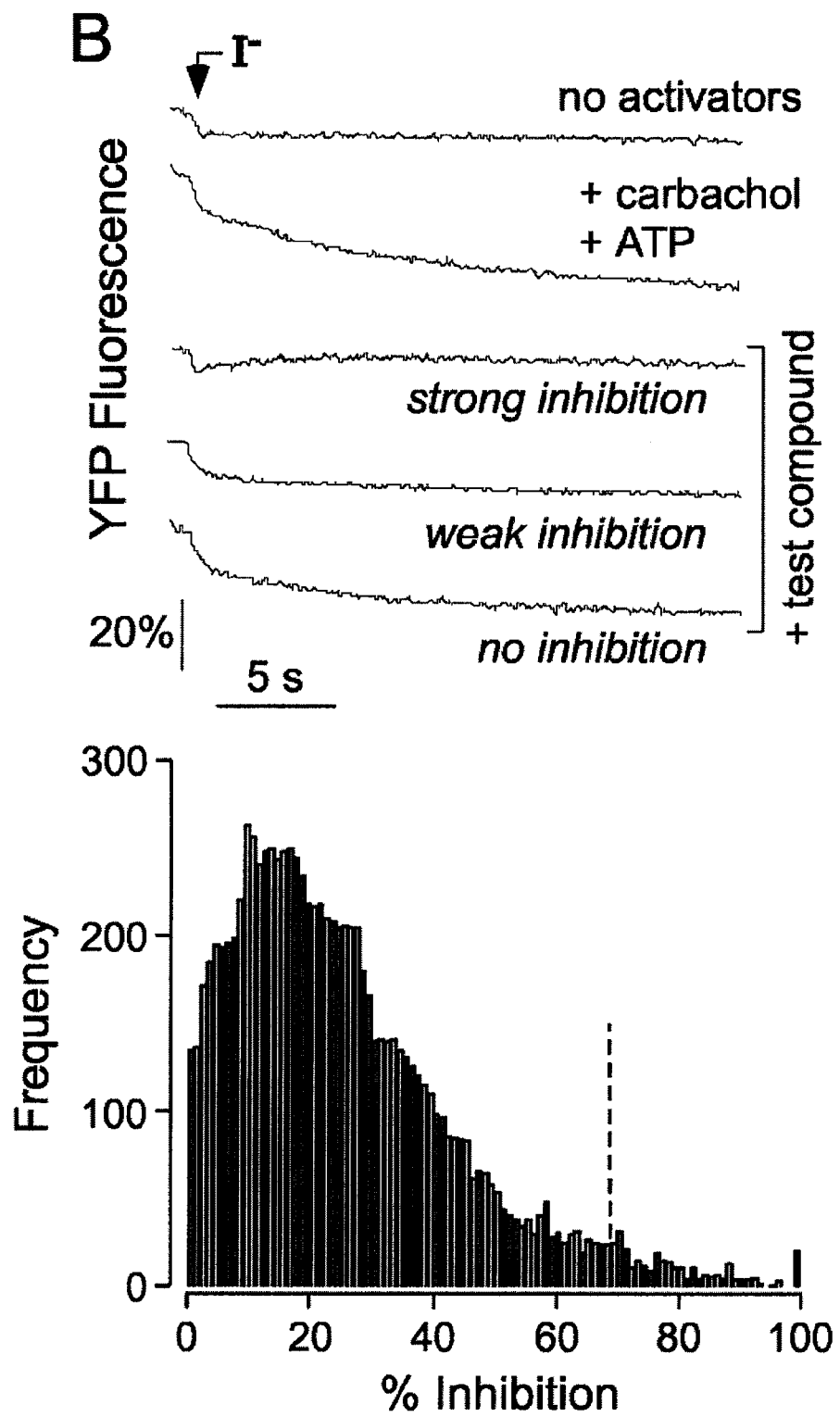

CaCC inhibitors were identified based on inhibition of ATP/carbachol stimulated iodide-influx. Screening yielded six classes of putative CaCC inhibitors, two of which, 3-acyl-2-aminothiophenes and 5-aryl-2-aminothiazoles, inhibited by >95% iodide influx in HT-29 cells in response to multiple calcium-elevating agonists. FIG. 3B (left) shows examples of data from single wells for compounds with 'strong', 'weak' and no inhibition activity. FIG. 3B (right) summarizes percentage inhibition data as a frequency histogram. Of 50,000 small molecules screened (in groups of four), 300 compound groups had CaCC inhibitory activity as defined by a 70% cutoff (vertical dashed line). Retesting of these 300 compound groups indicated a false-positive rate of ~40%.

Figure 3C:
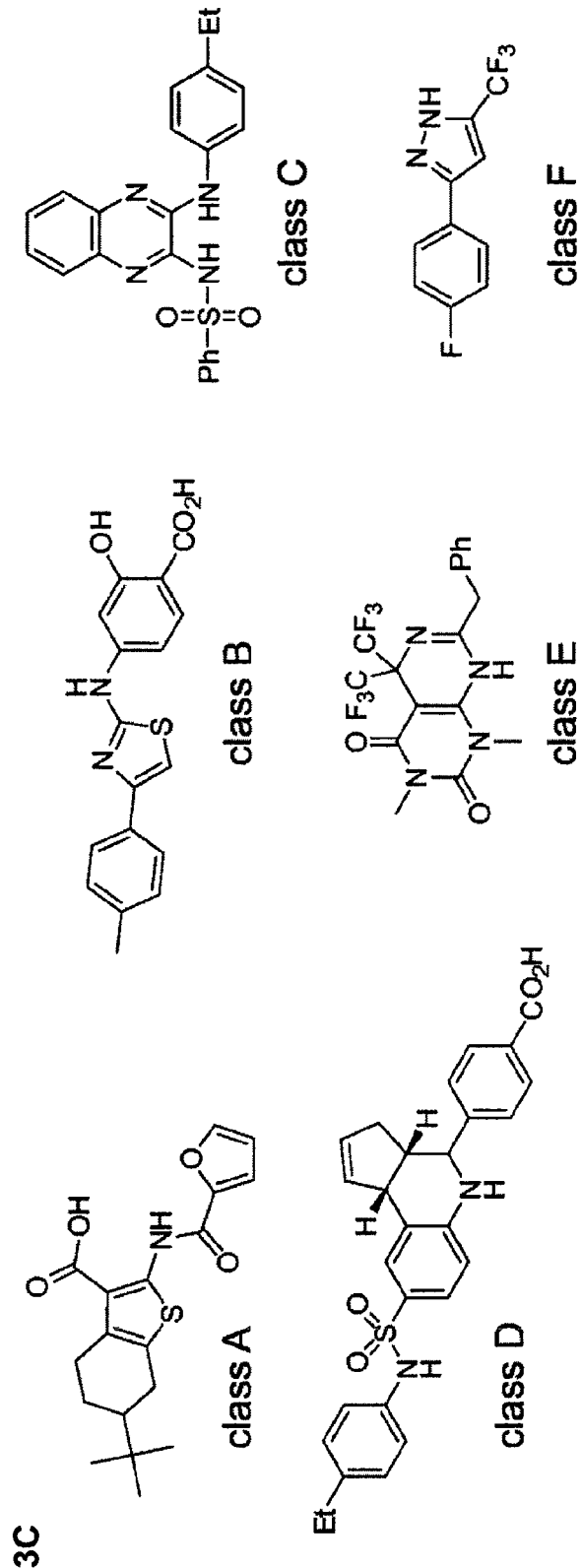

Further analysis was performed on fifteen-compound groups that produced greatest inhibition when retested at 10 and 30 μM concentrations. The compound responsible for activity in each group was determined by testing individual compounds in each group. In each case, a single active compound was identified in the groups of four. FIG. 3C shows structures of the most active of six classes of putative CaCC inhibitors (classes A-F) identified by single compound testing; in some cases, particularly for classes A and B, similar structures were seen several times. Percentage inhibition of these compounds at 30 μM was in the range 60 to >90%. Based on multiple criteria, including potency, water solubility, drug-like properties, identification of active analogs, chemical stability and CaCC targeting, compounds of classes A and B were analyzed further. Class A and B compounds were resynthesized, analyzed for mechanism-of-action, and assessed for 'druggability' by determining structure-activity relationships.

Example 2

Synthesis of Candidate CaCC Inhibitor Compounds

This example describes synthesis of exemplary class A and B compounds to high purity and verified their structures and chemical stability in aqueous solutions.

Figure 4A:
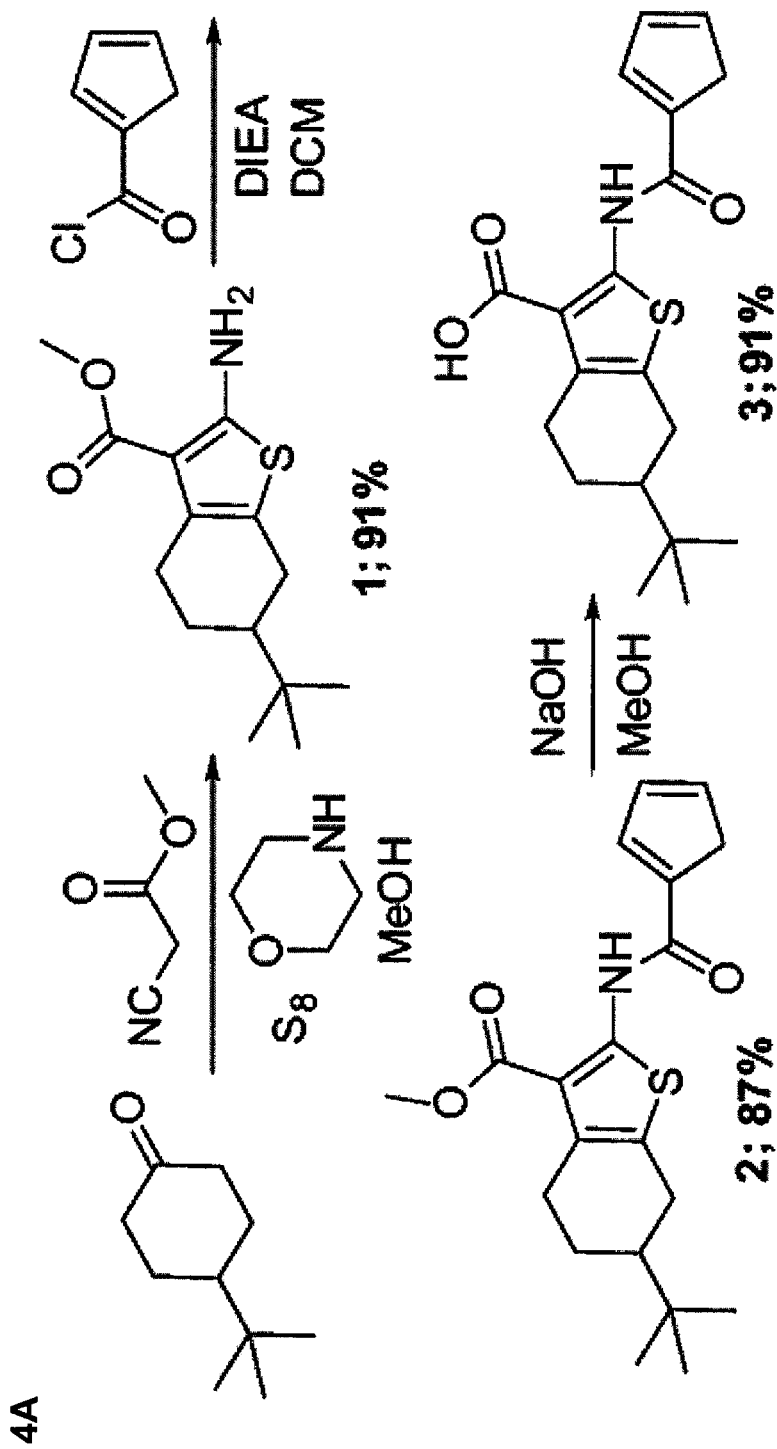
FIG. 4A-4C.

$CaCC_{inh}$-A01: The synthesis of $CaCC_{inh}$-A01 was accomplished in three steps (FIG. 4A), involving Knovenagle condensation of methyl cyanoacetate with t-butylcyclohexanone followed by cyclization on elemental sulfur. Purification by flash chromatography afforded the 2-aminothiophene Gewald product. Acyclation of the aminothiophene gave the N-acyl methyl ester [2] in good yield. Ester [2] was hydrolyzed with NaOH to give $CaCC_{inh}$-A01, which was purified by chromatography and recrystallization.

In greater detail, the synthesis of 6-t-butyl-2-(furan-2-carboxamido)-4,5,6,7-tetrahydrobenzo[b]thiophene-3-carboxylic acid [1] began with a mixture of 4-(t-butyl)cyclohexanone (0.154 g, 1.00 mmol), methyl-2-cyanoacetate (0.109 g, 1.1 mmol), morphiline (0.104 g, 1.2 mmol) and elemental sulfur (0.048 g, 1.5 mmol) in methanol (5 mL), which was microwaved for 10 min at 120° C. using a Biotage microwave reactor. Purification by flash chromatography afforded [1] (0.242 g, 0.91 mmol) in 91% yield (Gewald et al., *J. Prakt. Chem.* 311:402-407 29 (1969); Sridhar et al., *Tetrahedron Lett.* 48:3171-72 (2007)). Acylation of the amine with furfuryl chloride (0.186 mg, 0.70 mmol) gave compound [2] in 87% yield. Ester hydrolysis of [2] (0.179 g, 0.500 mmol) was accomplished with NaOH in methanol affording t-butylbenzothiophene ($CaCC_{inh}$-A01). $CaCC_{inh}$-A01 was purified by column chromatography (160 mg, 93% yield). $^1$H NMR (400 MHz, $CDCl_3$): δ 12.88 (s, 1H),7.59 (s, 1H), 7.30 (d, J=3.2 Hz, 1H), 6.59 (dd, J=7.6 Hz and 2.0 Hz, 1H), 3.18 (d, 2H), 2.72 (m, 2H), 2.43 (t, 1H), 2.05 (m, 1H), 1.51 (m, 1H), 1.35 (m, 1H), 0.95 (s, 9H); $^{13}$C NMR ($CDCl_3$): δ 179.2,170.6, 154.8, 149.1, 146.8, 145.4, 131.8, 128.3, 116.6, 112.9, 94.5, 45.1, 32.6, 27.4, 26.0, 24.5; LC-MS: m/z 346.16 [M+H]⁺ (Nova-Pak $C_{18}$ column, 99%, 200-400 nm).

Figure 4B:
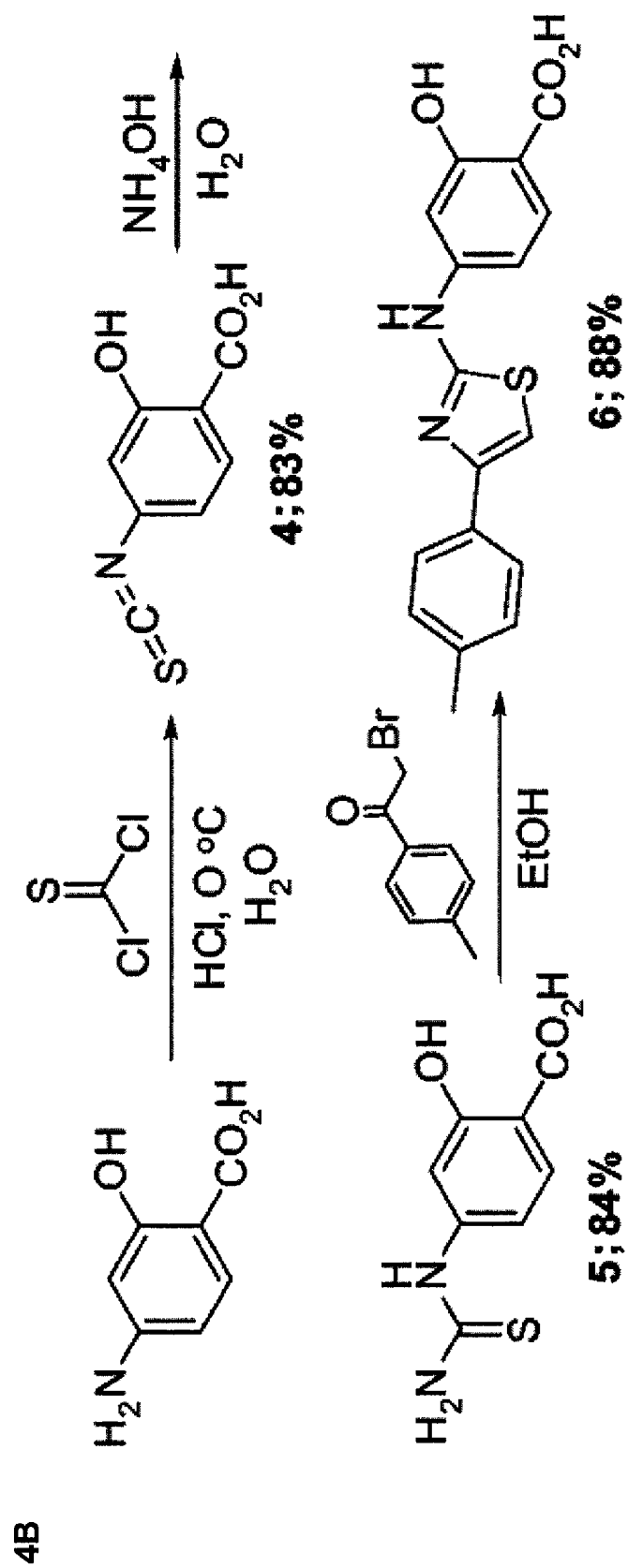

$CaCC_{inh}$-B01: The synthesis of $CaCC_{inh}$-B01 also involved three steps (FIG. 4B). Reaction of 4-amino-2-hydroxybenzoic acid with thiophosgene in HCl gave isothiocyanate in good yield. Treatment of isothiocyanate with ammonium hydroxide gave thiourea, which was then reacted with 2-bromo-1-p-tolylethanone to give $CaCC_{inh}$-B01.

In greater detail, the synthesis of 2-hydroxy-4-(4-p-tolylthiazol-2-ylaminobenzoic acid [4] began with the synthesis of thiourea [5]. Reaction of thiophosgene (2.7 g, 23.890 mmol) with 4-amino-2-hydroxybenzoic acid (3.06 g, 20 mol) in aqueous HCl (41 mL) afforded thioisocyanate by crystallization in 83% yield (Seligman et al., *J. Am. Chem. Soc.* 75:6334-35 (1953)). Treatment of thioisocyanate with ammonium hydroxide gave thiourea in 84% yield. Thiazole cyclization of thiourea [5] (0.300 g, 1.415 mmol) with 2-bromo-1-p-tolylethanone (0.298 g, 1.415 mmol) in EtOH (15 mL) gave aminothiazole. The aminothiazole was purified by column chromatography to afford $CaCC_{inh}$-B01 (406 mg, 88% yield). $^1$H NMR (400 MHz, $CDCl_3$): δ 10.67 (s, 1H), 7.80 (d, J=8.0 Hz, 2H), 7.71 (d, J=8.1 Hz, 1H), 7.58 (d, J=2.0 Hz, 1H), 7.36 (s, 1H), 7.25 (d, J=8.0 Hz, 2H), 7.04 (dd, J=8.1 Hz and 2.0 Hz, 1H), 2.49 (s, 1H), 2.31 (s, 3H); $^{13}$C NMR ($CDCl_3$): δ 171.7, 162.7, 162.0, 150.3, 147.2, 137.2, 131.7, 131.3, 129.3, 125.6, 108.5, 105.4, 103.6, 103.1, 20.8; LC-MS: m/z 327.11 [M+H]⁺ (Nova-Pak $C_{18}$ column, 97%, 200-400 nm).

CaCC$_{inh}$-A01 and CaCC$_{inh}$-B01 were confirmed by $^1$H-NMR, $^{13}$C-NMR, and mass spectrometry. The aqueous solubility of CaCC$_{inh}$-A01 and CaCC$_{inh}$-B01 in PBS was >500 μM, as measured by optical absorbance of a saturated solution after appropriate dilution. The high aqueous solubility is a consequence of their polarity and negative charge at physiological pH. By liquid chromatography compound purity was >97% and 99% for CaCC$_{inh}$-A01 and CaCC$_{inh}$-B01, respectively.

Figure 4C:
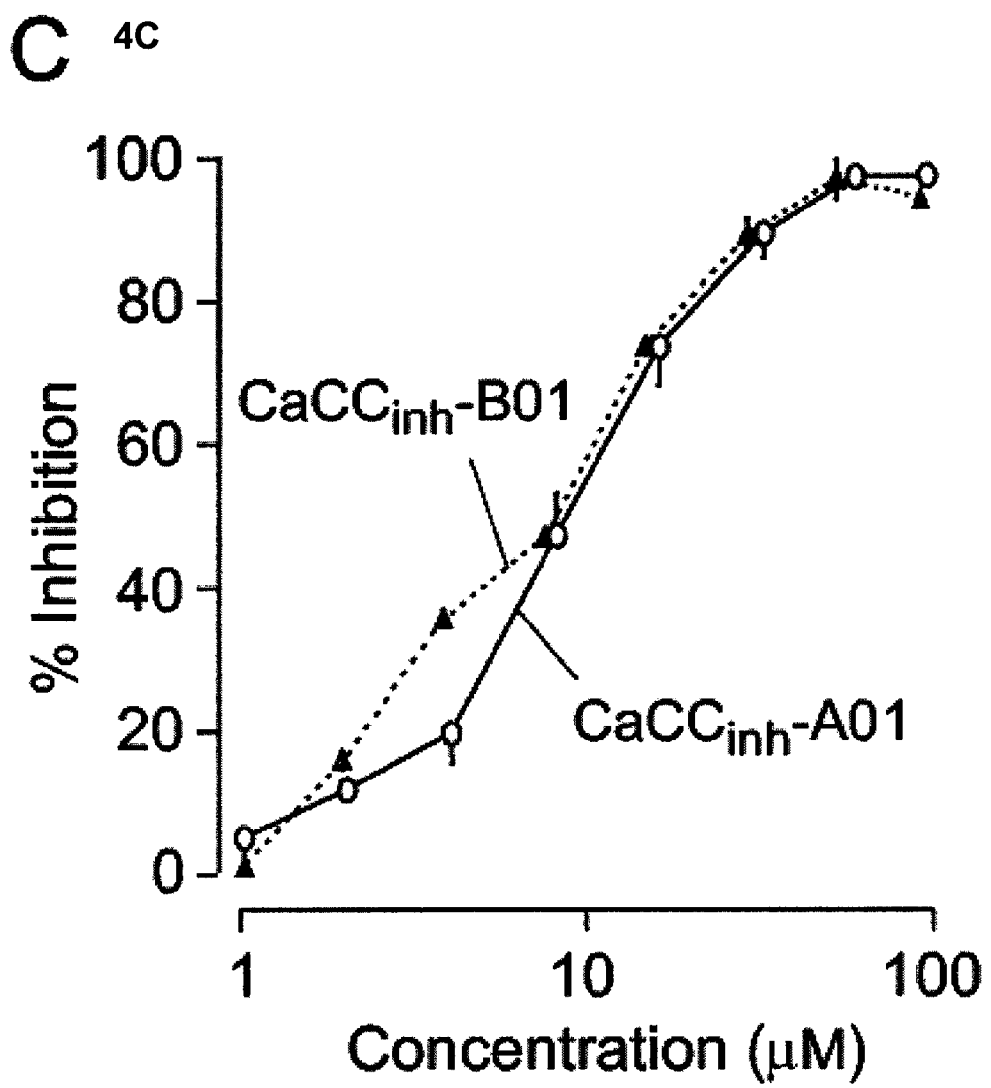

Testing of the purified compounds using the fluorescence plate reader assay verified their activities, with IC50 values ~10 μM (FIG. 4C). These apparent IC50 values are only semi-quantitative because of the multi-step nature of the screening assay and because of the ~3-fold compound dilution at the time of iodide addition during the assay. Accurate IC50s were determined by electrophysiological assays as described herein.

Example 3

Confirmation of CaCC as the Target of Class A and B Compounds

Figure 5A:
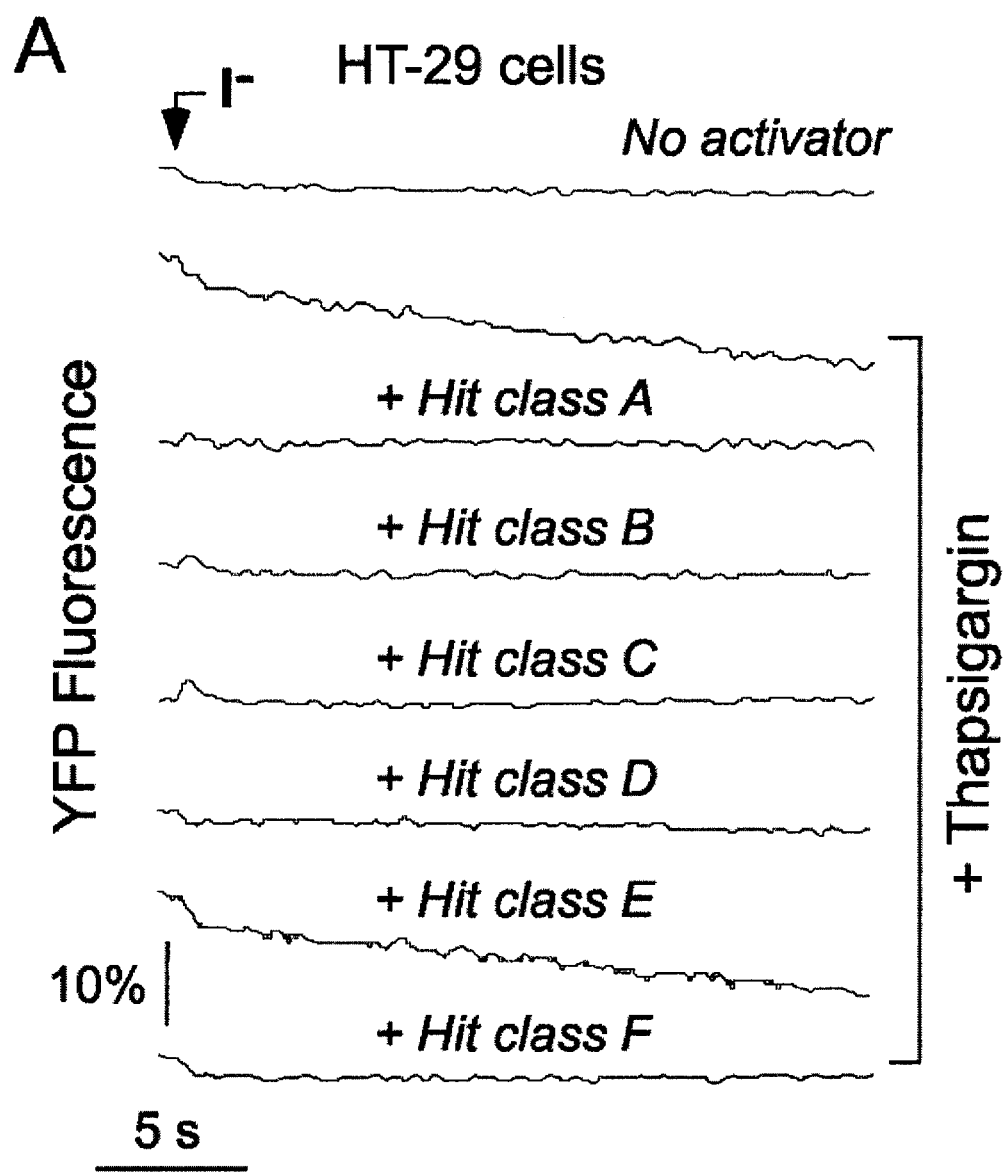
FIG. 5A-5D.

This Example describes analysis of Class A and B compounds to confirm their activity was specific for CaCCs. As shown in the schematic of the screening strategy illustrated in FIG. 1A, the screening assay could identify other target interactions such as ligand-receptor binding, calcium elevation, and calcium-calmodulin CaMKII) signaling. To distinguish between pre- and post-calcium signaling targets, compounds of each class were tested following stimulation of HT-29 cells by thapsigargin, which produces calcium elevation without ligand-receptor binding or phosphoinositide signaling. FIG. 5A shows that each of the compounds inhibited iodide influx following thapsigargin, except for the class E compounds, whose target is thus likely upstream from calcium signaling.

For experiments with thapsigargin or calcimycin, cells in 96-well plates at 100% confluence were washed 3 times with PBS, incubated with test compounds at 32.5 μM for 5 min in PBS in a final volume of 60 μl/well, and then incubated with 2 μM thapsigargin for 7 min or 10 μM calcimycin for 3 min before assay of iodide influx.

Figure 5B:
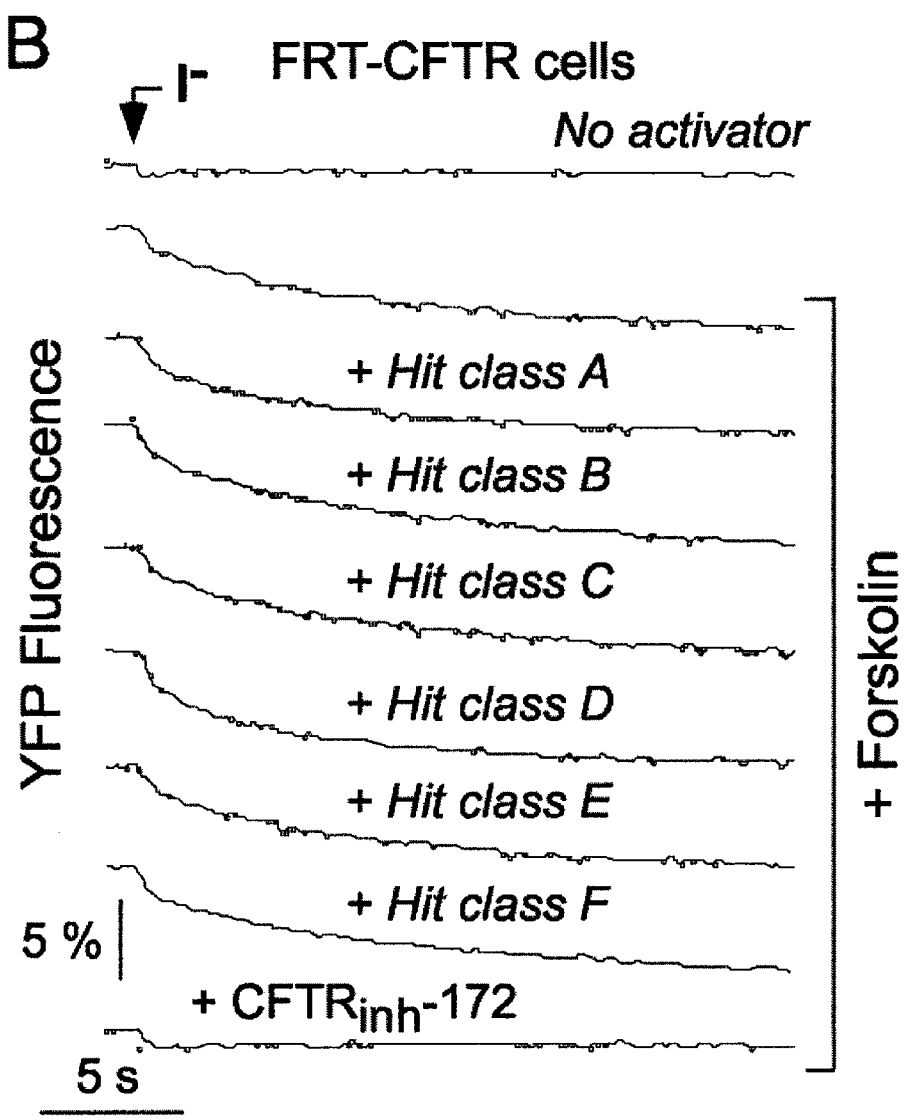

Cystic Fibrosis Transmembrane Conductance Regulator (CFTR) Experiments were performed to determine whether the compounds affected CFTR because CFTR is a major intestinal chloride channel and evidence exists for cross-talk between cAMP and calcium signaling in intestinal cell chloride secretion (Schultheiss et al., *Eur. J. Pharmacol.* 546:161-70 (2006); Takahashi et al., *J. Med. Microbiol.* 49:801-10 (2000); Chao et al., *EMBO J.* 13:1065-72 (1994)). As described (Ma et al., *J. Clin. Invest.* 110:1651-8 (2002)), FRT cells expressing human wildtype CFTR and YFP-H148Q/I152L, at 100% confluence, were washed 3 times with PBS, leaving 60 μL. CFTR was activated by a cocktail containing forskolin (20 μM), genistein (50 μM), and isobutylmethylxanthine (100 μM). Iodide influx as described in Example 1 was measured at 10 min after addition of test compounds by determining YFP fluorescence for 2 s before and 20 s after addition of 165 μl of PBS-iodide. FIG. 5B shows no CFTR was not inhibited by any of the compounds at 30 μM; CFTR$_{inh}$-172 inhibition shown is the positive control.

Example 3

Confirmation of CaCC as the Target of Class A and B Compounds

This Example describes analysis of Class A and B compounds to confirm that their activity was specific for CaCCs. As shown in the schematic of the screening strategy illustrated in FIG. 1A, the screening assay could identify other target interactions such as ligand-receptor binding, calcium elevation, and calcium-calmodulin CaMKII) signaling. To distinguish between pre- and post-calcium signaling targets, compounds of each class were tested following stimulation of HT-29 cells by thapsigargin, which produces calcium elevation without ligand-receptor binding or phosphoinositide signaling. FIG. 5A shows that each of the compounds inhibited iodide influx following thapsigargin, except for the class E compounds, whose target is thus likely upstream from calcium signaling.

For experiments with thapsigargin or calcimycin, cells in 96-well plates at 100% confluence were washed 3 times with PBS, incubated with test compounds at 32.5 μM for 5 min in PBS in a final volume of 60 μl/well, and then incubated with 2 μM thapsigargin for 7 min or 10 μM calcimycin for 3 min before assay of iodide influx.

Cystic Fibrosis Transmembrane Conductance Regulator (CFTR) Experiments were performed to determine whether the compounds affected CFTR because CFTR is a major intestinal chloride channel and evidence exists for cross-talk between cAMP and calcium signaling in intestinal cell chloride secretion (Schultheiss, et al., *Eur. J. Pharmacol.* 546:161-70 (2006); Takahashi, et al., *J. Med. Microbiol.* 49:801-10 (2000); Chao, et al., *EMBO J.* 13:1065-72 (1994)). As described (Ma et al., *J. Clin. Invest.* 110:1651-8 (2002)), FRT cells expressing human wildtype CFTR and YFP-H148Q/I152L, at 100% confluence, were washed 3 times with PBS, leaving 60 μL. CFTR was activated by a cocktail containing forskolin (20 μM), genistein (50 μM), and isobutylmethylxanthine (100 μM). Iodide influx as described in Example 1 was measured at 10 min after addition of test compounds by determining YFP fluorescence for 2 s before and 20 s after addition of 165 μl of PBS-iodide. FIG. 5B shows no CFTR was not inhibited by any of the compounds at 30 μM; CFTR$_{inh}$-172 inhibition shown is the positive control.

Figure 5C:
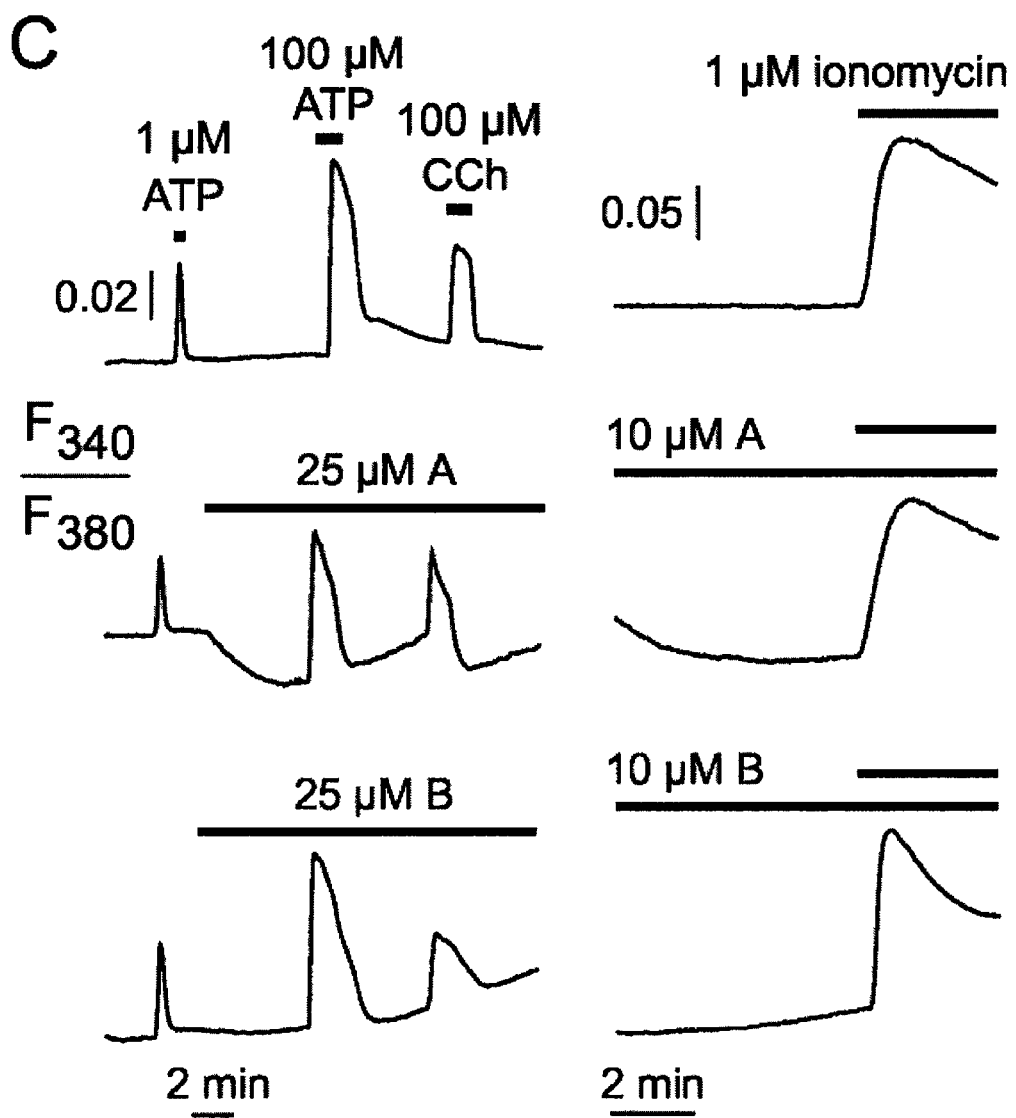

[Ca$^{2+}$]$_i$ measurements Cytoplasmic calcium was measured to determine whether CaCC$_{inh}$-A01 and CaCC$_{inh}$-B01 interfered with agonist-induced calcium signal in HT-29 cells. [Ca$^{2+}$]$_i$ was measured in confluent monolayers of HT-29 cells after loading with Fura-2 (2 μM Fura-2-AM, 30 min, 37° C.). Labeled cells were mounted in a perfusion chamber on the stage of an inverted epifluorescence microscope. Cells were superfused with (in mM): 140 NaCl, 5 KCl, 1 MgCl$_2$, 1 CaCl$_2$, 10 D-glucose, and 10 HEPES (pH 7.4), initially without and then with ATP/carbachol. Test compounds were present in some experiments for 10 min prior to agonist addition. Fura-2 fluorescence was recorded at excitation wavelengths of 340 nm and 380 nm using standard procedures FIG. 5C shows [Ca$^{2+}$]$_i$ elevations in response to 1 μM ATP, 100 μATP, and 100 μM carbachol (left), or 1 μM ionomycin (middle). Pretreatment with CaCC$_{inh}$-A01 or CaCC$_{inh}$-B01 at high concentration prior to agonist addition did not significantly reduce the ATP or carbachol-induced [Ca$^{2+}$]$_i$ elevations (right).

CaMKII Regulation of CaCC activation by CaMKII occurs in a cell type-dependent manner (Hartzell et al., Annu. Rev. Physiol. 67:719-58 (2005)). CaMKII has been reported to regulate calcium-activated chloride current in HT-29 and T84 cells (Worrell et al., Am. J. Physiol. 260: C877-82 (1991); Morris et al., Am. J. Physiol. 264:C977-85 (1993); Chan et al., J. Biol. Chem. 269:32464-8 (1994); Braun et al., J. Physiol. 488:37-55 (1995)). To determine whether the CaCC inhibitors interfered with ATP/carbachol-induced CaMKII activation, CaMKII phosphorylation in HT-29 cells was measured by immunoblot analysis. Calcium/calmodulin-dependent protein kinase II (CaMKII) was activated by 2 min treatment of HT-29 cells with ATP/carbachol (each 100 µM). Cells were then lysed with cell lysis buffer (20 mM Tris-HCl (pH 7.4), 1% Triton X-100, 150 mM NaCl, 2 mM EDTA, 50 mM α-glycerolphosphate, 1 mM Na$_3$VO$_4$, 1 mM DTT, and complete protease inhibitor mixture (Roche Applied Science)). Cell debris was removed by centrifugation, and proteins in the supernatant were resolved by SDS-PAGE and immunoblotted using standard procedures (transfer to PDVF membrane, 1 h blocking in 5% nonfat dry milk, primary/secondary antibody incubations, enhanced chemiluminescence detection). Rabbit polyclonal antibodies for anti-phospho-CaMKII (Thr286) and β-actin were purchased from Cell Signaling Technology (Danvers, Mass.).

Figure 5D:
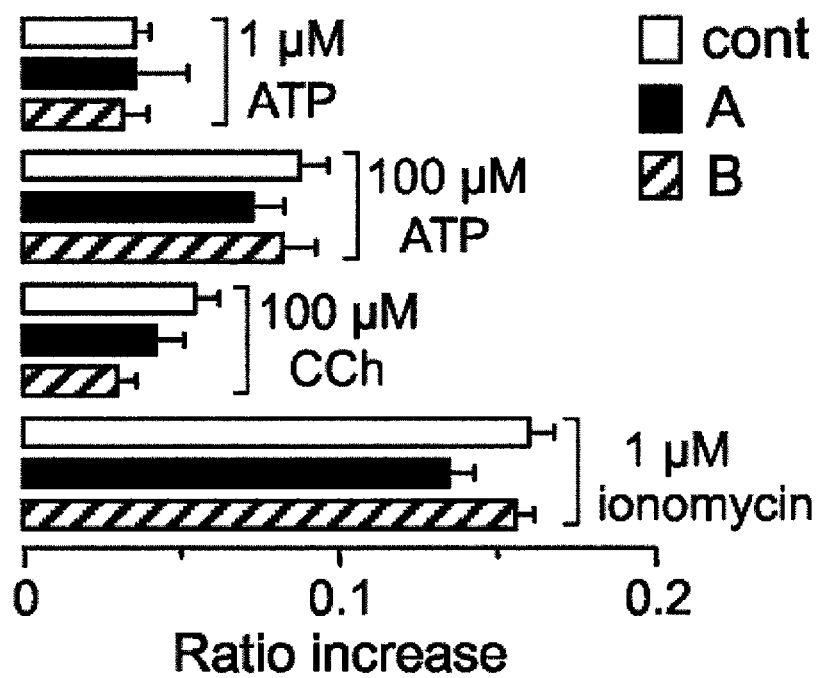
Figure 5D:
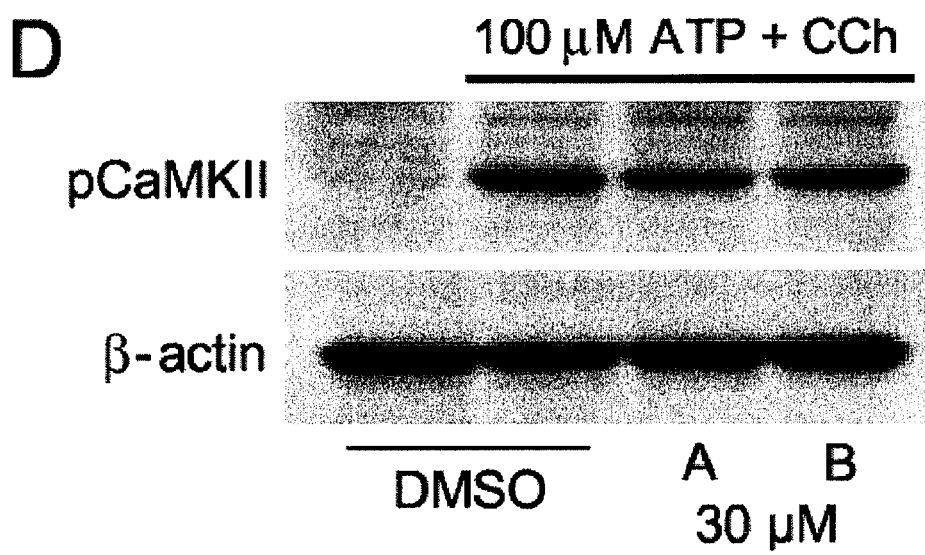

FIG. 5D present an immunoblot demonstrating the presence of pCaMKII immunoreactivity following agonist treatment. Pretreatment with 30 µM CaCC$_{inh}$-A01 or CaCC$_{inh}$-B01 did not significantly affect agonist-induced CaMKII phosphorylation. β-actin is shown as loading control.

Example 4

Effect of Class A and B Compounds on Calcium-Dependent Chloride Current

Patch Clamp—Calcium Dependent Chloride Current Whole-cell patch-clamp was performed to investigate inhibition of calcium-dependent chloride current in HT-29 cells by CaCC$_{inh}$-A01 and CaCC$_{inh}$-B01. Whole cell recordings were accomplished with HT-29 cells at room temperature. The pipette solution contained (in mM): 30 CsCl, 100 Cs-aspartate, 1 MgCl$_2$, 0.5 EGTA, 2 Tris-ATP, and 10 HEPES (pH 7.2 with CsOH), and the bath solution contained (in mM) 140 N-methyl-D-glucamine chloride (NMDG-Cl), 1 CaCl$_2$, 1 MgCl$_2$, 10 glucose, and 10 HEPES (pH 7.2). In one set of studies, symmetric NMDG-Cl solutions contained 140 mM NMDG-Cl, 1 mM MgCl$_2$, 0.5 mM EGTA, 2 mM Tris-ATP, and 10 mM HEPES, pH 7.2. Pipettes were pulled from borosilicate glass and had resistances of 3-5 MΩ after fire polishing. Seal resistances were typically between 3-10 GΩ. After establishing the whole cell configuration, CaCCs were activated by 1 µM ionomycin. Whole cell currents were elicited by applying hyperpolarizing and depolarizing voltage pulses from a holding potential of 0 mV to potentials between −120 mV and +120 mV in steps of 20 mV. Currents were filtered at 5 kHz, and digitized and analyzed using an AxoScope 10.0 system and a Digidata 1440A AC/DC converter (Molecular Devices, Sunnyvale, Calif.). Mean currents were expressed as current densities (picoampere per picofarad (pA/pF)).

Figure 6A:
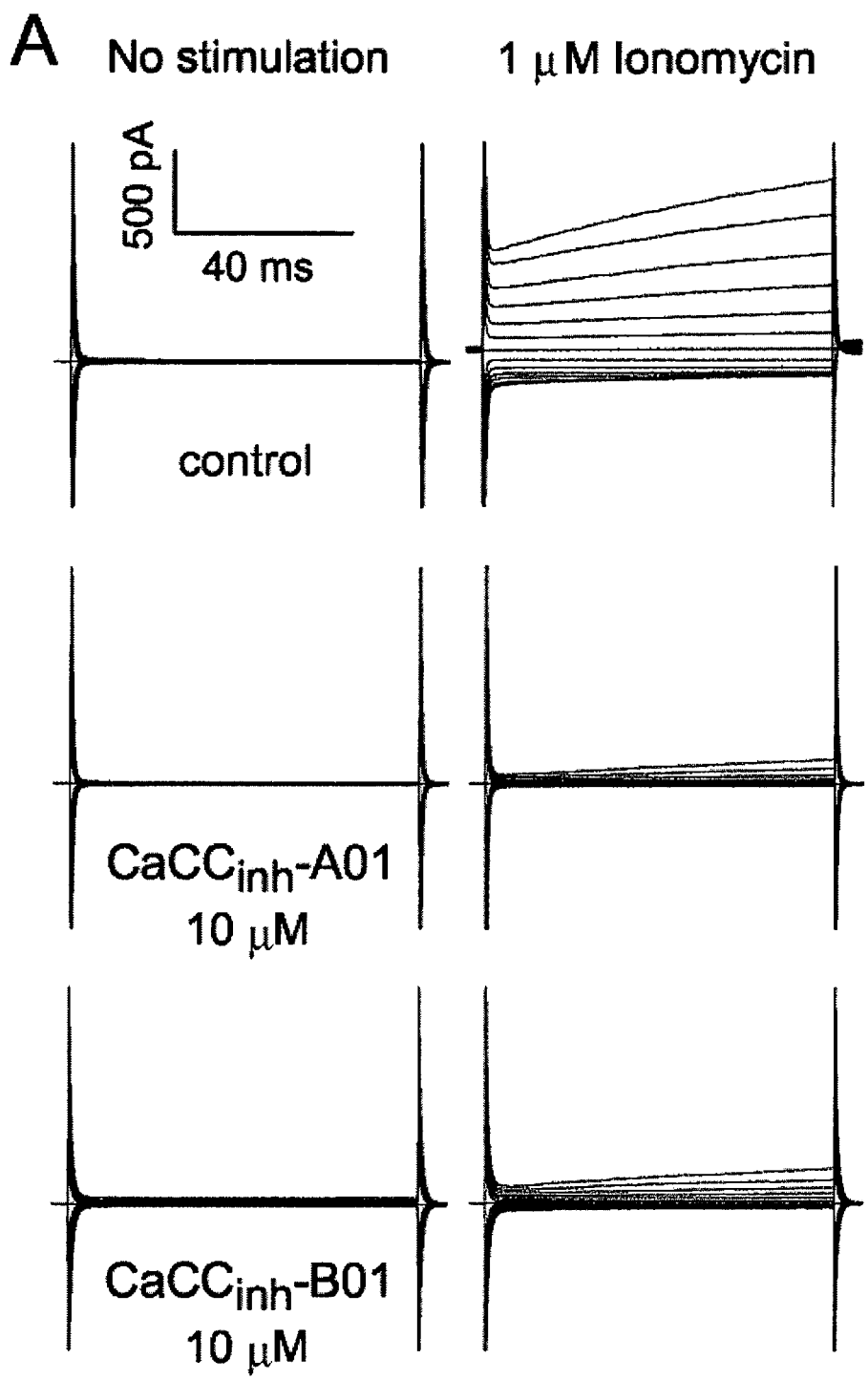
FIG. 6A-6D. CaCC channel activity in the whole-cell configuration was measured in HT-29 cells.
Figure 6B:
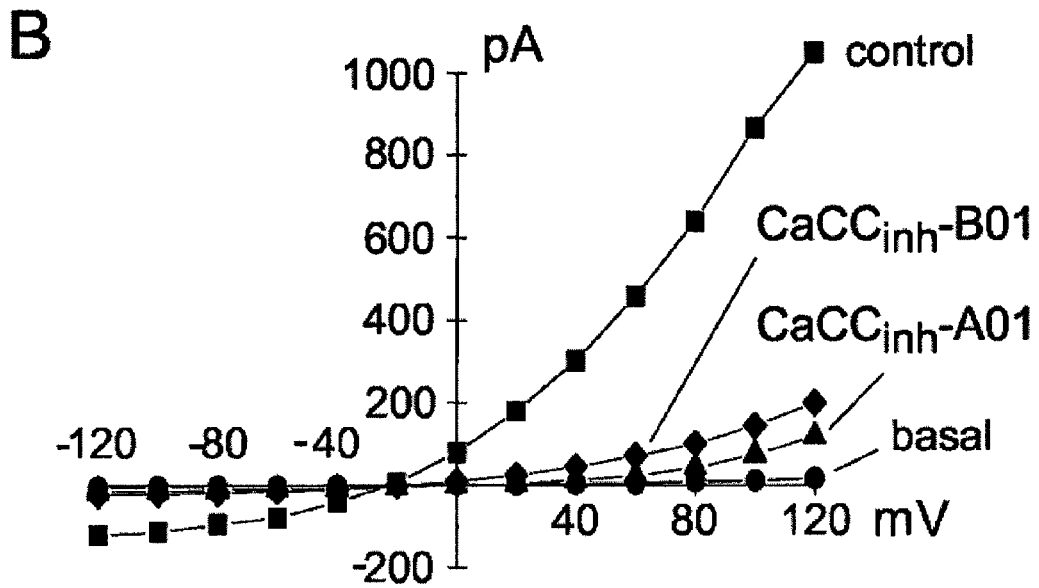
Figure 6C:
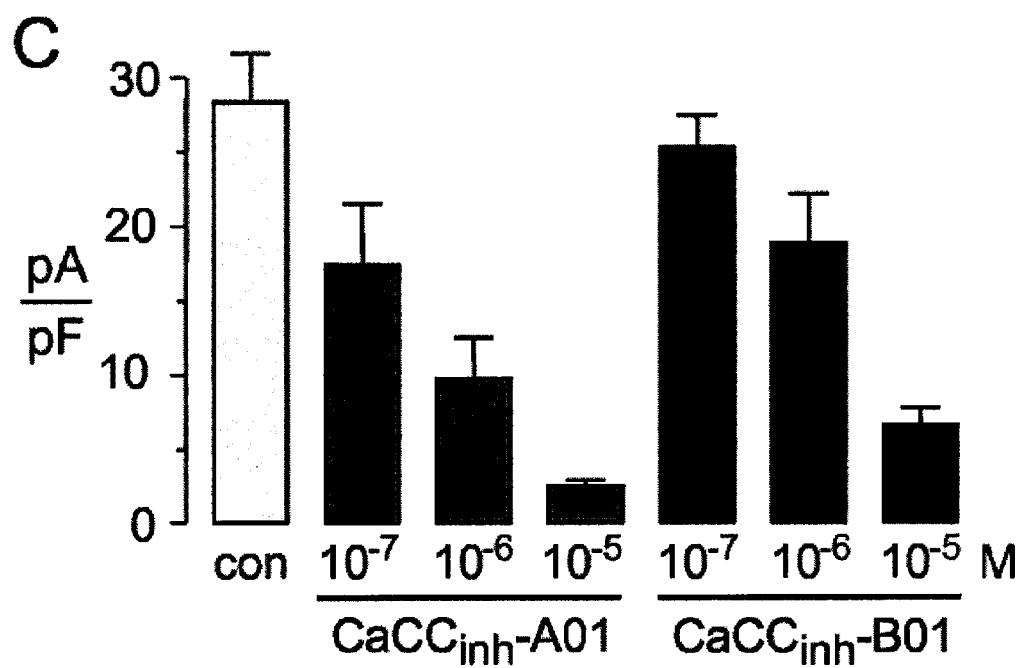
Figure 6D:
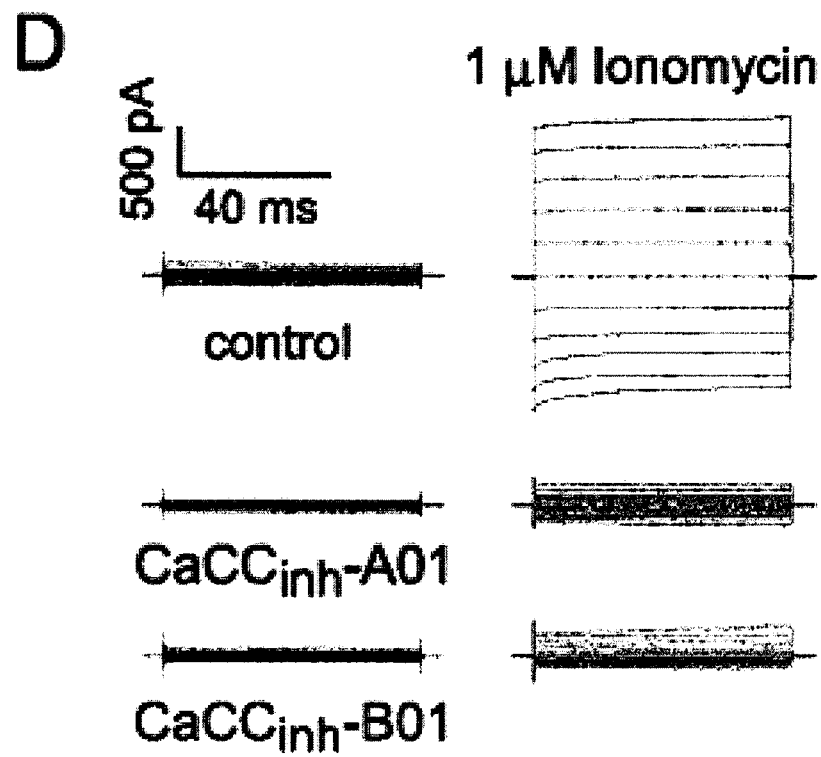
Figure 6D:
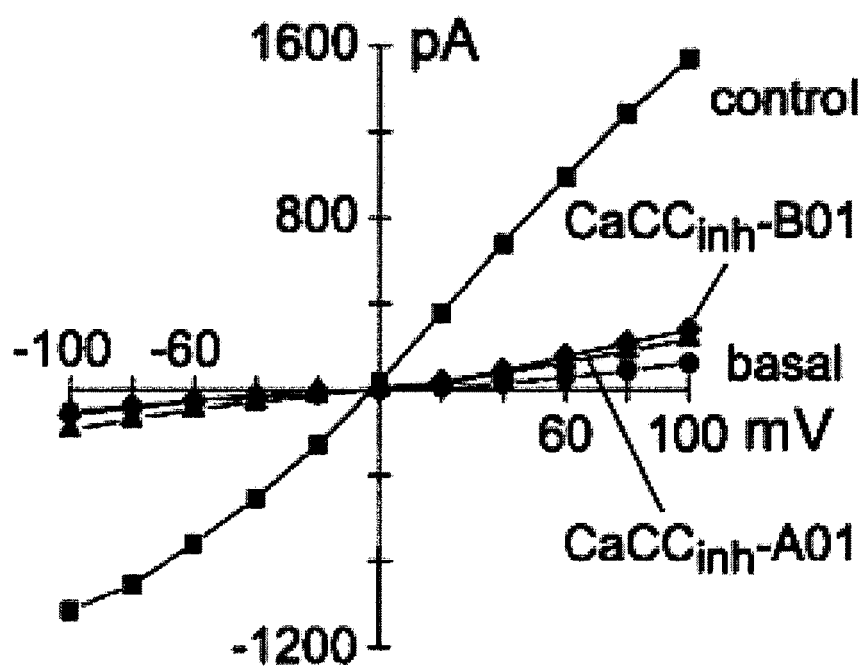

Treatment with 1 µM ionomycin produced large currents of 28±3 pA/pF (Vm+100 mV) in NMDG-Cl solutions, with outwardly rectifying I-V relationship as shown in FIGS. 6A and B). Ionomycin-stimulated currents were measured when the current was maximally activated at a Vm of −40 mV. As summarized in FIG. 6C, calcium-dependent chloride current was reduced by 38±14%, 66±10%, and 91±1% by 0.1, 1 and 10 µM CaCC$_{inh}$-A01, respectively, and by 11±7%, 34±12%, and 77±4% by 0.1, 1 and 10 µM CaCC$_{inh}$-B01. As a control to exclude interference by transient receptor potential and nonselective cation channels, ionomycin-induced chloride currents were also recorded in the whole-cell configuration using symmetric NMDG-Cl solutions. The results are presented in FIG. 6D. As predicted, pretreatment with CaCC$_{inh}$-A01 and CaCC$_{inh}$-B01 reduced ionomycin-induced currents.

Short Circuit Current Measurements (Chloride Secretion) Chloride secretion was measured in T84 cells to investigate whether the CaCC inhibitors identified from screening of HT-29 cells also inhibited the CaCC in a different human intestinal cell line. ATP/carbachol were used to induce calcium-dependent chloride secretion in well-differentiated T84 cell monolayers. T84 cells were seeded at a density of 10$^5$ cm$^{-2}$ on permeable supports (Snapwell, 1.12 cm$^2$ surface area) and grown until confluent. Supports containing confluent cell monolayers were mounted in Snapwell diffusion chambers. Cells were bathed for a 30 min stabilization period in HCO$_3^-$-buffered solution containing (mmol/L): 120 NaCl, 5 KCl, 1 MgCl$_2$, 1 CaCl$_2$, 10 D-glucose, 5 HEPES, and 25 NaHCO$_3$ (pH 7.4), aerated with 95% O$_2$/5% CO$_2$ at 37° C. Monolayers were voltage-clamped at 0 mV (EVC4000 Multi-Channel V/I Clamp, World Precision Instruments), and short-circuit current (Isc) was recorded continuously with agonists/inhibitors added at specified times.

Figure 7A:
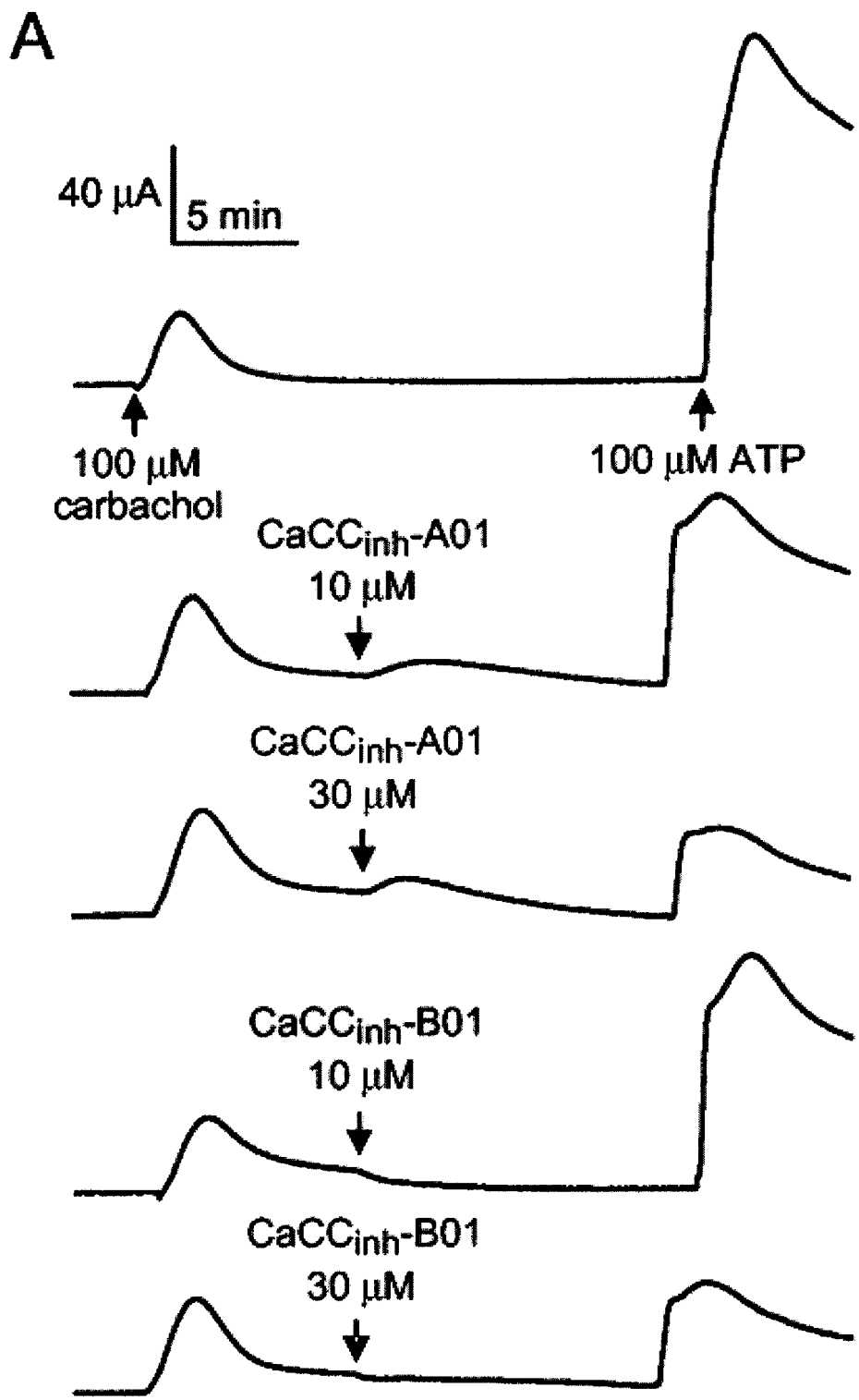
FIG. 7A-7B present data showing inhibition of chloride secretion in T84 cells by short-circuit current analysis.
Figure 7B:
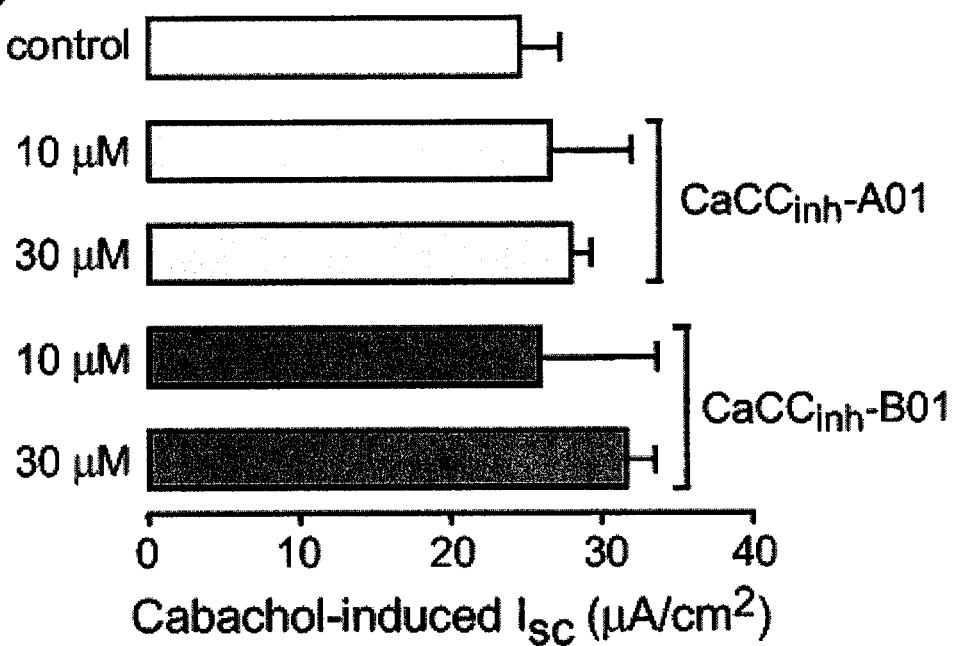
Figure 7B:
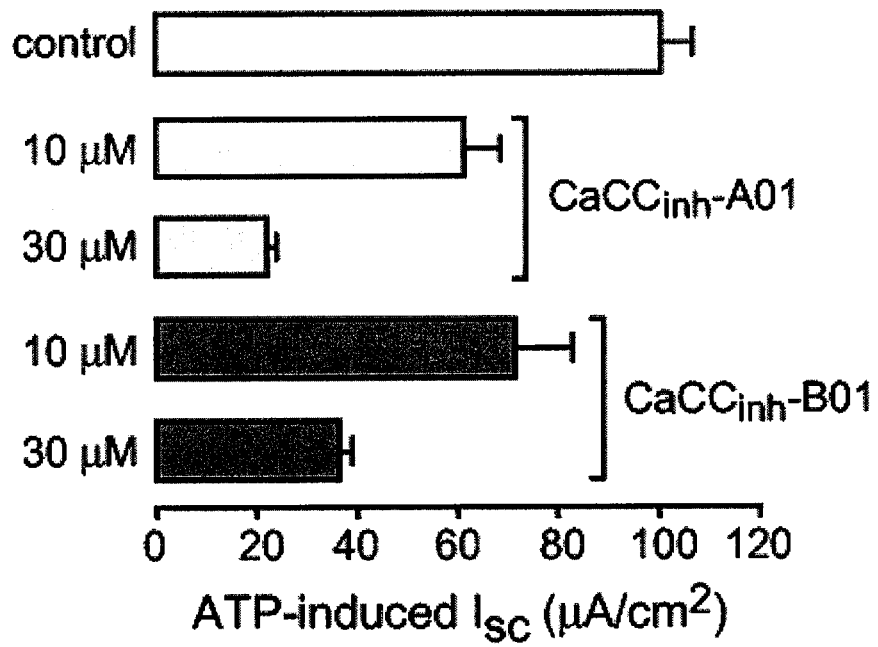

Application of carbachol followed ATP after a recovery period produced large short-circuit current as shown in FIG. 7A. Carbachol and ATP-induced short-circuit currents are summarized in FIG. 7B. Initial carbachol-induced currents were similar, as expected, indicated similar chloride secretory activities of the cultures. ATP-induced short circuit-currents were reduced by 38±7% and 78±3% at 10 and 30 µM CaCC$_{inh}$-A01, respectively, and by 29±11% and 64±3% by 10 and 30 µM CaCC$_{inh}$-B01.

The aminothiophenes and aminothiazoles identified in the screen and analyzed in the experiments described above did not interfere with agonist-induced cytoplasmic calcium elevation or calmodulin (CaMKII) phosphorylation. As indicated by patch-clamp analysis, the compounds that were tested inhibited CaCC gating. These results confirm that the phenotype-based small molecule screen identified novel chemical classes of inhibitors of CaCC chloride conductance that target the CaCC itself rather than upstream signaling mechanisms and/or any of the other mechanisms tested.

Example 4

Effect of Class A and B Compounds on Calcium-Dependent Chloride Current

This Example describes the structure activity relationship of the aminothiophene compounds (i.e., having a structure of formula I or substructures thereof) and aminothiazole compounds (i.e., having a structure of formula II or substructures thereof). SAR analysis was performed on 936 commercially available aminothiophenes (class A analogs) and 944 aminothiazoles (class B analogs). Tables 3 and 4 provide semi-quantitative CaCC inhibition data (from plate reader assay, see Example 1) for 18 active aminothiophenes (class A) and 14 active aminothiazoles (class B).

TABLE 3

Structure-Activity of Aminothiophene (Class A) CaCC Inhibitors

| Compound | R¹ | R² | R³ | n | % inhibition at 25 μM |
|---|---|---|---|---|---|
| CaCC$_{inh}$-A01 | t-butyl | —OH | 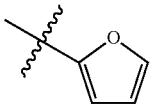 [SMILES: *c1ccco1] | 1 | 100 |
| CaCC$_{inh}$-A02 | t-butyl | —OH | 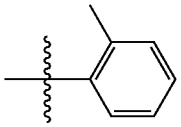 [SMILES: *c1ccccc1C] | 1 | 95 |
| CaCC$_{inh}$-A03 | t-butyl | —OH | 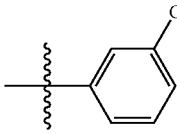 | 1 | 50 |
| CaCC$_{inh}$-A04 | t-butyl | —OH | 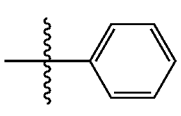 | 1 | 85 |
| CaCC$_{inh}$-A05 | t-butyl | —OH | 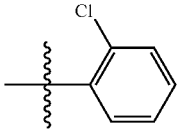 [SMILES: *c1ccccc1Cl] | 1 | 75 |
| CaCC$_{inh}$-A06 | t-butyl | —OCH$_2$CH$_3$ | 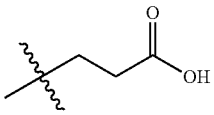 [SMILES: *CCC(=O)O] | 1 | 75 |
| CaCC$_{inh}$-A07 | t-butyl | —OCH$_2$CH$_3$ | 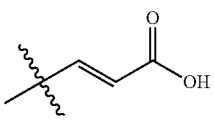 [SMILES: */C=C/C(=O)O] | 1 | 98 |
| CaCC$_{inh}$-A08 | t-butyl | —OCH$_2$CH$_3$ | 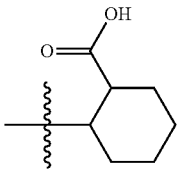 [SMILES: *C1CCCCC1C(=O)O] | 1 | 80 |
| CaCC$_{inh}$-A09 | t-butyl | —OCH$_3$ | 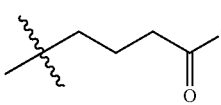 | 1 | 45 |
| CaCC$_{inh}$-A10 | t-pentyl | —OCH$_2$CH$_3$ | 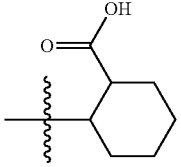 | 1 | 75 |

TABLE 3-continued

Structure-Activity of Aminothiophene (Class A) CaCC Inhibitors

| Compound | R¹ | R² | R³ | n | % inhibition at 25 μM |
|---|---|---|---|---|---|
| CaCC$_{inh}$-A11 | t-butyl | —OCH$_3$ | 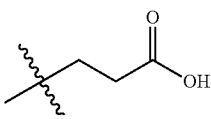 [SMILES: *CCC(=O)O] | 1 | 81 |
| CaCC$_{inh}$-A12 | H | —OH | 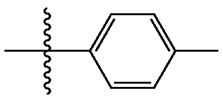 [SMILES: *c1ccc(C)cc1] | 2 | 15 |
| CaCC$_{inh}$-A13 | H | —OH | 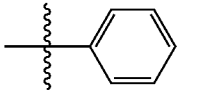 | 2 | 27 |
| CaCC$_{inh}$-A14 | H | —OH | 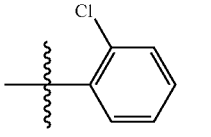 [SMILES: *c1ccccc1Cl] | 2 | 18 |
| CaCC$_{inh}$-A15 | H | —OH | 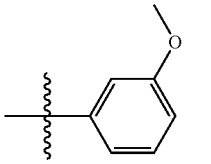 [SMILES: *c1cccc(OC)c1] | 1 | 20 |
| CaCC$_{inh}$-A16 | t-butyl | 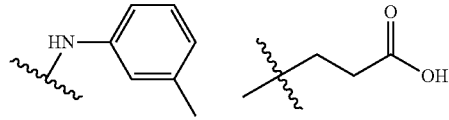 | 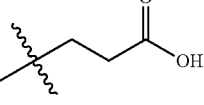 | 1 | 42 |
| CaCC$_{inh}$-A17 | H | —OH | 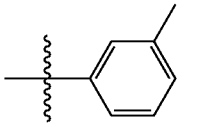 | 1 | 07 |
| CaCC$_{inh}$-A18 | t-butyl | 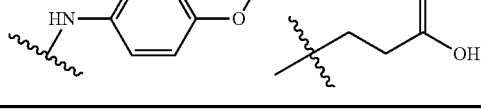 | 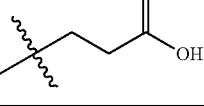 | 1 | 35 |

A common moiety in compounds that exhibited the highest inhibitory activity in each compound class was the presence of a carboxylic acid functional group, which is also present in certain other known chloride channel inhibitors.

Class A compounds (aminothiophene) that had t-butyl at position R¹ conferred the greatest inhibition; inhibition was reduced when R¹ was H (e.g., CaCC$_{inh}$-A12-A15) and reduced when R¹ was methyl. While compounds having a cyclohexyl ring system had greater activity than compounds with cyclopentyl and cycloheptyl (varying n) rings (i.e., the ring to which R¹ is attached), several cycloheptylthiophenes were active. At R², hydroxy, methoxy, ethoxy and substituted phenyl amides were identified. Compounds with a methyl ester or an ethyl ester at R² were active, and certain of these compounds identified also had an alkyl carboxylic acid present at R³ (see, e.g., CaCC$_{inh}$-A06-A11). With respect to the moiety comprising R³ (—NHC(=O)R³), activity was observed for compounds comprising substituted phenyl, substituted heterocycles, and substituted alkyl. The most active compound that had substituted alkyl at R³ was the analog comprising trans-3-carboxyacrylamido (CaCC$_{inh}$-A07). The presence of substituted phenyl at R³ in compounds was observed. A variety of compounds with heterocycles at R³ were screened; active compounds comprising a furyl substituent were identified, and the most potent compound identified was (CaCC$_{inh}$-A01).

TABLE 4

Structure-Activity of Aminothiazole (Class B) CaCC inhibitors

| Compound | $R^7$ | $R^8$ | $R^9$ | $R^{10}$ | % inhibition at 25 μM |
|---|---|---|---|---|---|
| CaCC$_{inh}$-B01 | 3-carboxy-4-hydroxyphenyl | H | H | 4-methyl | 100 |
| CaCC$_{inh}$-B02 | 3-chloro-4-methylphenyl | —CH$_2$CO$_2$H | H | 4-methyl | 40 |
| CaCC$_{inh}$-B03 | 3-bromophenyl | —CH$_2$CO$_2$H | H | 4-methyl | 60 |
| CaCC$_{inh}$-B04 | 2,4-dichlorophenyl | —CH$_2$CO$_2$H | H | 4-methyl | 65 |
| CaCC$_{inh}$-B05 | 3-trifluoromethylphenyl | —CH$_2$CO$_2$H | H | 4-methyl | 60 |
| CaCC$_{inh}$-B06 | 4-carboxyphenyl | n-propyl | 2-methyl | 4-methyl | 100 |
| CaCC$_{inh}$-B07 | 4-bromophenyl | —CH$_2$CO$_2$H | 2-methyl | 4-methyl | 70 |
| CaCC$_{inh}$-B08 | 3-trifluoromethylphenyl | —CH$_2$CO$_2$H | 2-methyl | 4-methyl | 75 |
| CaCC$_{inh}$-B09 | 4-isobutylphenyl | H | H | 4-phenoxy | 65 |
| CaCC$_{inh}$-B10 | 4-cyclohexylphenyl | H | H | 3-CF$_3$ | 55 |
| CaCC$_{inh}$-B11 | 4-ethoxyphenyl | —CH$_2$CO$_2$H | H | 4-methyl | 65 |

TABLE 4-continued

Structure-Activity of Aminothiazole (Class B) CaCC inhibitors

| Compound | $R^7$ | $R^8$ | $R^9$ | $R^{10}$ | % inhibition at 25 μM |
|---|---|---|---|---|---|
| CaCC$_{inh}$-B12 | (3-methylbenzoyl) | phenyl | H | 4-methyl | 03 |
| CaCC$_{inh}$-B13 | —CH$_2$CH$_3$ | H | H | 4-methyl | 20 |
| CaCC$_{inh}$-B14 | (4-methoxyphenyl) | —(CH$_2$)$_2$CO$_2$H | H | 4-methoxy | 18 |

With respect to aminothiazole compounds, the substituent at $R^{10}$ that was observed in a majority of active compounds was a methyl substitution at the 4-position of the aromatic ring (see, e.g., CaCC$_{inh}$-B01-B06). Certain active analogs of such compounds had an additional methyl substitution at the 2-position (see, e.g., CaCC$_{inh}$-B07-B09). As observed with aminothiophene compounds, aminothiazole compounds that had a carboxylic acid functional group were most active. Examples of such aminothiazole compounds had carboxy-substituted alkyl at $R^8$ or a carboxy substituted phenyl at $R^7$. At position $R^8$, active compounds contained hydrogen, propyl, or an acetic acid group (—(CH$_2$)—C(=O)OH). At the position $R^7$, a variety of substituted phenyl groups were tolerated. Electron donating substituents produced inactive compounds.

All the above U.S. patents, U.S. patent application publications, U.S. patent applications, foreign patents, foreign patent applications, and non-patent publications referred to in this specification and/or listed in the Application Data Sheet, are incorporated herein by reference, in their entirety.

From the foregoing, although specific embodiments of the invention have been described herein for purposes of illustration, various modifications may be made without deviating from the spirit and scope of the invention. Those skilled in the art will recognize, or be able to ascertain, using no more than routine experimentation, many equivalents to the specific embodiments of the invention described herein. Such equivalents are intended to be encompassed by the following claims.

We claim the following:

1. A composition comprising a physiologically acceptable excipient and a compound having the following structure (I):

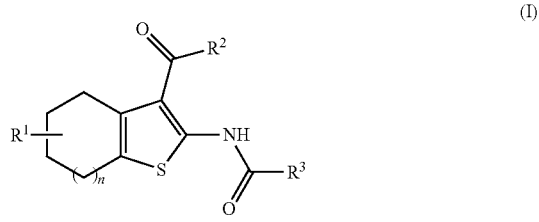

(I)

or a pharmaceutically acceptable salt, prodrug or stereoisomer thereof, wherein $R^1$ is hydrogen or optionally substituted alkyl;

$R^2$ is hydroxy, optionally substituted alkoxy, or optionally substituted phenylamino;

$R^3$ is alkyl substituted with —COOH, alkenyl substituted with —COOH, optionally substituted cycloalkyl, optionally substituted phenyl, or optionally substituted heterocyclyl; and n is 0, 1, or 2, and wherein the compound of structure I comprises at least one —COOH, and provided that when n is 1, $R^1$ is branched alkyl.

2. The composition of claim 1 wherein n is 1 and the compound has the following structure I(A), wherein $R^1$ is branched alkyl:

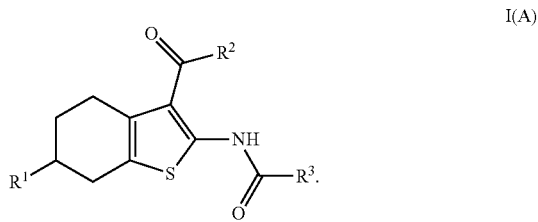

I(A)

3. The composition of claim 2 wherein $R^1$ is tert-butyl, or tert-pentyl, and the compound has the following structure (Ib), or (Ic):

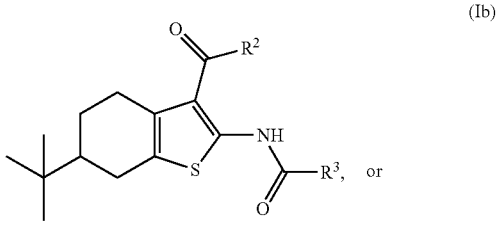

(Ib)

or

-continued

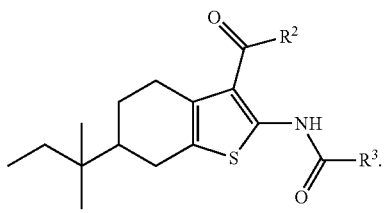

(Ic)

4. The composition of claim 1 wherein $R^2$ is —$OR^4$ wherein $R^4$ is hydrogen or optionally substituted $C_{1-6}$ alkyl; or phenylamino optionally substituted with $C_{1-6}$ alkoxy or $C_{1-6}$ alkyl.

5. The composition of claim 1 wherein $R^3$ is optionally substituted furanyl; $C_1$-$C_6$ alkyl substituted with —COOH; $C_1$-$C_6$ alkenyl substituted with —COOH; optionally substituted cyclohexyl; phenyl; or phenyl substituted with halo, $C_{1-6}$ alkyl, $C_{1-6}$ alkoxy, or —COOH.

6. The composition of claim 1 wherein $R^3$ is —$(CH_2)_2$C(=O)OH or —CH=CHC(=O)OH.

7. The composition of claim 1 wherein $R^3$ is cyclohexyl substituted with —COOH.

8. The composition of claim 2 wherein, wherein $R^1$ is tert-butyl, or tert-pentyl, $R^2$ is —$OR^4$ wherein $R^4$ is hydrogen or optionally substituted $C_{1-6}$ alkyl, and the compound has the following structure (Id):

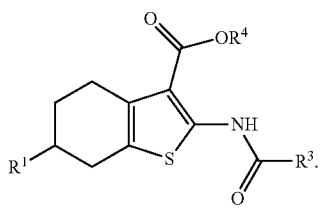

(Id)

9. The composition of claim 8 wherein $R^3$ is optionally substituted furanyl; $C_1$-$C_6$ alkyl substituted with —COOH; $C_1$-$C_6$ alkenyl substituted with —COOH; optionally substituted cyclohexyl; phenyl; or phenyl substituted with halo, $C_{1-6}$ alkyl, $C_{1-6}$ alkoxy, or —COOH.

10. The composition of claim 8 wherein $R^3$ is —$(CH_2)_2$C(=O)OH; —CH=CHC(=O)OH; phenyl substituted with chloro, methyl, or methoxy; or cyclohexyl substituted with —COOH.

11. The composition of claim 2 wherein the compound has any one of the following structures (Ie), (If), (Ig), or (Ih):

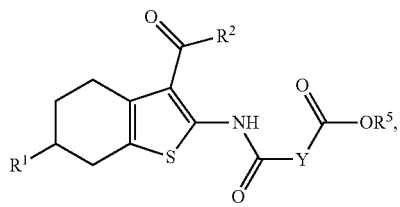

(Ie)

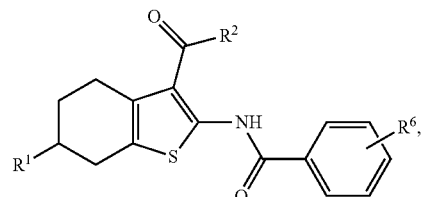

(If)

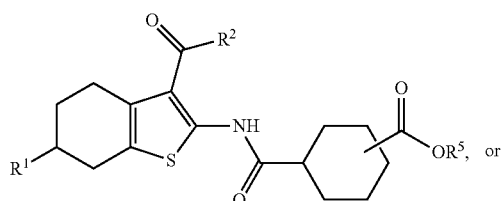

(Ig)

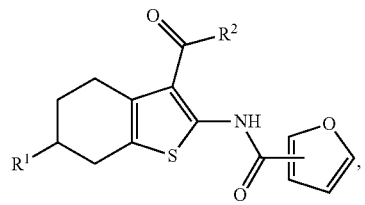

(Ih)

wherein Y is optionally substituted $C_1$-$C_6$ alkylene or optionally substituted $C_1$-$C_6$ alkenylene; $R^5$ is hydrogen or optionally substituted $C_{1-4}$ alkyl; and $R^6$ is hydrogen, optionally substituted alkyl, optionally substituted alkoxy, —COOH, or halo.

12. The composition of claim 11 wherein $R^6$ is hydrogen, halo, $C_{1-6}$ alkyl, $C_{1-6}$ alkoxy, or —COOH.

13. The composition of claim 11 wherein $R^1$ is tert-butyl, or tert-pentyl; and $R^2$ is —$OR^4$ wherein $R^4$ is hydrogen or optionally substituted $C_{1-6}$ alkyl.

14. The composition of claim 13 wherein $R^4$ is hydrogen, methyl, or ethyl.

15. The composition of claim 11 wherein $R^2$ is phenylamino optionally substituted with methoxy or methyl.

16. The composition of claim 1, wherein n is 2; $R^1$ is hydrogen; $R^2$ is —$OR^4$; and $R^3$ is optionally substituted phenyl, and the compound has the following structure (Ii):

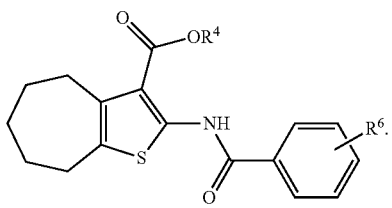

(Ii)

wherein $R^4$ is hydrogen or optionally substituted $C_{1-6}$ alkyl; and $R^6$ is hydrogen, optionally substituted alkyl, optionally substituted alkoxy, or halo.

17. The composition of claim 1 wherein the compound is:
6-tert-butyl-2-(furan-2-carboxamido)-4,5,6,7-tetrahydrobenzo[b]thiophene-3-carboxylic acid;
6-tert-butyl-2-(2-methylbenzamido)-4,5,6,7-tetrahydrobenzo[b]thiophene-3-carboxylic acid;
6-tert-butyl-2-(3-chlorobenzamido)-4,5,6,7-tetrahydrobenzo[b]thiophene-3-carboxylic acid;

2-benzamido-6-tert-butyl-4,5,6,7-tetrahydrobenzo[b]thiophene-3-carboxylic acid;

6-tert-butyl-2-(2-chlorobenzamido)-4,5,6,7-tetrahydrobenzo[b]thiophene-3-carboxylic acid;

4-(6-tert-butyl-3-(ethoxycarbonyl)-4,5,6,7-tetrahydrobenzo[b]thiophen-2-ylamino)-4-oxobutanoic acid;

(E)-4-(6-tert-butyl-3-(ethoxycarbonyl)-4,5,6,7-tetrahydrobenzo[b]thiophen-2-ylamino)-4-oxobut-2-enoic acid;

2-(6-tert-butyl-3-(ethoxycarbonyl)-4,5,6,7-tetrahydrobenzo[b]thiophen-2-ylcarbamoyl)cyclohexanecarboxylic acid;

5-(6-tert-butyl-3-(methoxycarbonyl)-4,5,6,7-tetrahydrobenzo[b]thiophen-2-ylamino)-5-oxopentanoic acid;

2-(3-(ethoxycarbonyl)-6-tert-pentyl-4,5,6,7-tetrahydrobenzo[b]thiophen-2-ylcarbamoyl)cyclohexanecarboxylic acid;

4-(6-tert-butyl-3-(methoxycarbonyl)-4,5,6,7-tetrahydrobenzo[b]thiophen-2-ylamino)-4-oxobutanoic acid;

2-(4-methylbenzamido)-5,6,7,8-tetrahydro-4H-cyclohepta[b]thiophene-3-carboxylic acid;

2-benzamido-5,6,7,8-tetrahydro-4H-cyclohepta[b]thiophene-3-carboxylic acid;

2-(2-chlorobenzamido)-5,6,7,8-tetrahydro-4H-cyclohepta[b]thiophene-3-carboxylic acid;

2-(3-methoxybenzamido)-5,6,7,8-tetrahydro-4H-cyclohepta[b]thiophene-3-carboxylic acid;

4-(6-tert-butyl-3-(m-tolylcarbamoyl)-4,5,6,7-tetrahydrobenzo[b]thiophen-2-ylamino)-4-oxobutanoic acid;

or 4-(6-tert-butyl-3-(4-methoxyphenylcarbamoyl)-4,5,6,7-tetrahydrobenzo[b]thiophen-2-ylamino)-4-oxobutanoic acid.

\* \* \* \* \*

UNITED STATES PATENT AND TRADEMARK OFFICE
CERTIFICATE OF CORRECTION

PATENT NO. : 9,789,095 B2  
APPLICATION NO. : 14/688365  
DATED : October 17, 2017  
INVENTOR(S) : Alan S. Verkman et al.

Page 1 of 1

It is certified that error appears in the above-identified patent and that said Letters Patent is hereby corrected as shown below:

In the Specification

Column 1, Line 21:
Delete "EY13574".

Signed and Sealed this
Third Day of December, 2024

Katherine Kelly Vidal
*Director of the United States Patent and Trademark Office*